United States Patent
Chung et al.

(10) Patent No.: US 11,319,540 B2
(45) Date of Patent: May 3, 2022

(54) HIF 1-ALPHA ANTISENSE OLIGONUCLEOTIDES

(71) Applicant: OliPass Corporation, Yongin-si (KR)

(72) Inventors: Shin Chung, Yongin-si (KR); Daram Jung, Hwaseong-Si (KR); Bongjun Cho, Yongin-Si (KR); Heungsik Yoon, Seongnam-Si (KR); Kangwon Jang, Yongin-Si (KR)

(73) Assignee: OliPass Corporation, Yongin-si (KR)

( * ) Notice: Subject to any disclaimer, the term of this patent is extended or adjusted under 35 U.S.C. 154(b) by 393 days.

(21) Appl. No.: 16/341,272

(22) PCT Filed: Oct. 11, 2017

(86) PCT No.: PCT/IB2017/001385
§ 371 (c)(1),
(2) Date: Apr. 11, 2019

(87) PCT Pub. No.: WO2018/069764
PCT Pub. Date: Apr. 19, 2018

(65) Prior Publication Data
US 2021/0292767 A1    Sep. 23, 2021

Related U.S. Application Data

(60) Provisional application No. 62/406,577, filed on Oct. 11, 2016.

(51) Int. Cl.
*C07H 21/02* (2006.01)
*C07H 21/04* (2006.01)
*C12N 15/113* (2010.01)
*A61P 35/00* (2006.01)

(52) U.S. Cl.
CPC .......... *C12N 15/1138* (2013.01); *A61P 35/00* (2018.01); *C12N 15/113* (2013.01); *C12N 2310/11* (2013.01); *C12N 2310/3181* (2013.01); *C12N 2310/333* (2013.01); *C12N 2310/336* (2013.01); *C12N 2320/30* (2013.01)

(58) Field of Classification Search
CPC ................................................... C12N 15/113
See application file for complete search history.

(56) References Cited

U.S. PATENT DOCUMENTS

2004/0101858 A1*  5/2004  Ward ................. C07F 9/65616
                                                    435/6.13
2006/0204502 A1    9/2006  Borea et al.

FOREIGN PATENT DOCUMENTS

KR    2011/0010691 A      2/2011
WO    WO-2009/113828 A2   9/2009

OTHER PUBLICATIONS

Date et al. (Am J Physiol Cell Physiol, 288, C314-320, 2005).*
Schubert et al. (European Journal of Neuroscience, 29, 1323-1334, 2009).*
Extended European Search Report for EP Application No. 17860878.2 dated Jun. 26, 2020.
Zhang et al., "Treatment with siRNA and antisense oligonucleotides targeted to HIF-1alpha induced apoptosis in human tongue squamous cell carcinomas," International Journal of Cancer, 111(6):849-857 (2004).
Haaima et al., "Increased DNA binding and sequence discrimination of PNA oligomers containing 2,6-diaminopurine," Nucleic Acids Res, 25(22):4639-4643 (1997).
International Search Report and Written Opinion for International Application No. PCT/IB2017/001385 dated Mar. 12, 2018.
Lee et al., "Antihepatoma activity of chaetocin due to deregulated splicing of hypoxia-inducible factor 1α pre-mRNA in mice and in vitro," Hepatology, 53(1):171-180 (2011).
Rajeev et al., "High-Affinity Peptide Nucleic Acid Oligomers Containing Tricyclic Cytosine Analogues," Org Lett, 4(25):4395-4398 (2002).

* cited by examiner

*Primary Examiner* — Amy H Bowman
(74) *Attorney, Agent, or Firm* — Foley Hoag LLP; David P. Halstead; Mi Cai

(57) ABSTRACT

Provided are peptide nucleic acid derivatives targeting a part of the human HIF-1α pre-mRNA. The peptide nucleic acid derivatives potently induce exon skipping to yield splice variants of HIF-1α mRNA in cells, and are useful to treat indications or conditions involving the overexpression of HIF-1α.

23 Claims, 18 Drawing Sheets

Specification includes a Sequence Listing.

Figure 3C

Exon 1 | Exon 3

SEQUENCE LISTING

<160> NUMBER OF SEQ ID NOS: 23

<210> SEQ ID NO 1
<211> LENGTH: 20
<212> TYPE: RNA
<213> ORGANISM: Homo sapiens

<400> SEQUENCE: 1
uguuaaguag gauaaguucu                                                  20

<210> SEQ ID NO 2
<211> LENGTH: 14
<212> TYPE: RNA
<213> ORGANISM: Homo sapiens

<400> SEQUENCE: 2
uaaguaggau aagu                                                        14

<210> SEQ ID NO 3
<211> LENGTH: 14
<212> TYPE: RNA
<213> ORGANISM: Homo sapiens

<400> SEQUENCE: 3
aaguaggaua aguu                                                        14

<210> SEQ ID NO 4
<211> LENGTH: 14
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 4
cagaacttat ccta                                                      14

<210> SEQ ID NO 5
<211> LENGTH: 30
<212> TYPE: RNA
<213> ORGANISM: Homo sapiens

<400> SEQUENCE: 5
guuguuguua aguaggauaa guucugaacg                                     30

<210> SEQ ID NO 6
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 6
caattcatcc tactc                                                     15

<210> SEQ ID NO 7
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 7
attcatccta ttcaa                                                     15

<210> SEQ ID NO 8
<211> LENGTH: 17
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 8
agaactcatc ctactta                                                   17

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
cttgcctttc cttctcttct                                                20

<210> SEQ ID NO 10
<211> LENGTH: 18
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 10
aacccagaca tatccacc                                                18

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
tgaagacatc gcggggac                                                18

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
tttttcacaa ggccatttct                                              20

<210> SEQ ID NO 13
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cttgctcatc agttgccact tc                                           22

<210> SEQ ID NO 14
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
aagtttcctc acacgcaaat ag                                           22

<210> SEQ ID NO 15
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gaaagcacag atgaattgc                                               19

<210> SEQ ID NO 16
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
```
tcatgtcacc atcatctgt                                                    19

<210> SEQ ID NO 17
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
ctaactggac acagtgtgtt tg                                                22

<210> SEQ ID NO 18
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
tctgtgtgta agcatttctc tc                                                22

<210> SEQ ID NO 19
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
gccttgtgaa aagggtaaa g                                                  21

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ccatgttgca gactttatgt                                                   20

<210> SEQ ID NO 21
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
cgcgaacgac aagaaaaa                                                     18

<210> SEQ ID NO 22
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22

```
ctgtggtgac ttgtcctttt                                              19

<210> SEQ ID NO 23
<211> LENGTH: 70
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 23
gagggcgccg gcggcgcgaa cgacaagaaa aagtgatttg gatattgaag atgacatgaa    60
agcacagatg                                                          70
```

HIF 1-ALPHA ANTISENSE OLIGONUCLEOTIDES

RELATED APPLICATIONS

This application is a national-stage filing under 35 U.S.C. § 371 of International Application No. PCT/IB2017/001385, filed Oct. 11, 2017, which claims the benefit of priority to U.S. Provisional Application No. 62/406,577, filed Oct. 11, 2016, each of which is incorporated by reference herein in its entirety.

SEQUENCE LISTING

The instant application contains a Sequence Listing which has been submitted electronically in ASCII format and is hereby incorporated by reference in its entirety. Said ASCII copy, created on Apr. 8, 2019, is named OSH-00201_(32567-00201)_SL.txt and is 5,278 bytes in size.

BACKGROUND

Hypoxia-inducible factor 1-alpha (HIF-1α) is induced under hypoxia (oxygen deficiency) conditions in mammalian cells. [*Proc. Natl. Acad. Sci. USA* vol 92(12), 5510-5514 (1995)] HIF-1α plays an important role in regulating oxygen homeostasis in cells as well as systemically. [*Ann. Rev. Cell. Dev. Biol.* vol 15, 551-578 (1999)] HIF-1α has been known to induce the transcription of more than 60 gene products including erythropoietin (EPO), vascular endothelial growth factor (VEGF), cyclooxygenase 2 (COX-2), glucose transporters (GLUTs), and so on. [*Trends Mol. Med.* vol 8, S62-67 (2002); *Nature Rev. Cancer* vol 3, 721-732 (2003); *J. Biol. Chem.* vol 276, 9519-9525 (2001)] Thus HIF-1α may be taken as a master switch being turned on in response to hypoxia.

HIF-1α has been known to be involved in diverse physiological or pathological situations. For example, HIF-1α induces VEGF which is a well-known factor of angiogenesis. HIF-1α promotes erythropoiesis via EPO expression. HIF-1α induces the transcription of genes involved in cell proliferation and survival. [*Exp. Mol. Med.* vol 36(1), 1-12 (2004)]

HIF-1α is encoded by the HIF-1α (or HIF1A) gene and is a subunit of a heterodimeric transcription factor HIF-1. Under normoxia (normal oxygen level), the HIF-1α protein level is regulated through hydroxylation at a prolyl residue by prolylhydroxylase 2 (PHD2). [*EMBO J.* vol 22(16), 4082-4090 (2003)] The hydroxylated product of HIF-1α is recognized by von Hippel-Lindau (VHL) tumor suppressor protein. Binding of HIF-1α to VHL predisposes HIF-1α to ubiquitination and therefore proteasomal degradation. Under hypoxic conditions, PHD2 is inactivated, the proteasomal degradation of HIF-1α is suppressed, and resultantly the HIF-1α level increases. [*Endocrine-Related Cancer* vol 13, S61-S75 (2006)]

HIF-1α Expression in Tumors: Hypoxia is a hallmark of the tumor microenvironment. As tumor grows, portions of the tumor mass become poorly vascularized, creating hypoxic microenvironments within the tumor. Intra-tumoral hypoxia induces adaptive changes in cancer cells that can result in increased chemotherapy resistance and a predisposition to metastasis. One mechanism behind these adaptive responses to a low-oxygen environment is an increase in the level of HIF-1α protein in cancer cells.

According to literatures, HIF-1α has been found overexpressed in primary and metastatic tumors. The expression level of HIF-1α in human cancers correlated with intratumoral angiogenesis and mortality. [*Cancer Res.* vol 61, 2911-2916 (2001); *Clin. Cancer Res.* vol 7, 1661-1668 (2001); *Cancer Res.* vol 60, 4693-4696 (2000); *Am. J. Pathol.* vol 157, 411-421 (2000); *Cancer Res.* vol 59, 5830-5835 (1999)]

Breast cancer (T1/T2) patients with a high HIF-α level tended to show a shorter duration of disease-free survival (DFS) and a shorter distant metastasis-free survival (DMFS), suggesting that the intratumoral HIF-1α level would be a good prognostic marker in high risk breast patients. [*Breast Cancer Res.* vol 6(3), R191-R198 (2004)] Hypoxia or HIF-1α over-expression in HCT116 human colon carcinoma cells stimulated the invasion of the colon carcinoma cells into Matrigel. The metastatic invasion was inhibited by a HIF-1α siRNA. [*Cancer Res.* vol 63, 1138-1143 (2003)] HIF-1α inhibitors would be useful to inhibit tumor metastasis.

Small Molecule Inhibitors of HIF-1α: HIF-1α is a transcription factor. There are small molecules that inhibit the functional activity or expression of HIF-1α. Such small molecule inhibitors indirectly affect the functional activity or level of HIF-1α. There are abundant examples of such HIF-1α inhibitors as follows. [*Endocrine-Related Cancer* vol 13, S61-S75 (2006); *Oncotarget* vol 7(7), 8172-8183 (2016)]

Microtubule inhibitor taxol, topoisomerase I inhibitor topotecan, and histone deacetylase inhibitor FK228 inhibit HIF-1α protein expression via unknown mechanism. Topoisomerase II inhibitor anthracycline inhibits HIF-1α by reducing the HIF-1α mRNA level. HSP90 inhibitor geldanamycin destabilizes HIF-1α protein or inhibits the binding of HIF-1α to DNA. P300 CH1 inhibitor chetomin inhibits HIF-1 trans-activating activity. Proteasome inhibitor bortezomib inhibits HIF-1α activity through unidentified mechanism. PI3K inhibitor wortmanin, mTOR inhibitor rapamycin, COX-2 inhibitor celecoxib, tyrosine kinase inhibitor genistein, and erbB2 monoclonal antibody trastuzumab (herceptin) block the translation of HIF-1α mRNA. However, such inhibitors do not selectively react with the HIF-1α pathway, and therefore it would be difficult to assess their therapeutic contribution due to HIF-1α inhibition.

Ribosomal Protein Synthesis: Proteins are encoded by 2-deoxyribose nucleic acid (DNA). DNA is transcribed to produce pre-mRNA (pre-messenger ribonucleic acid) in the nucleus. The introns of pre-mRNA are enzymatically spliced out to yield mRNA (messenger ribonucleic acid), which is then translocated into the cytosolic compartment. In the cytosol, a complex of translational machinery called ribosome binds to mRNA and carries out the protein synthesis as it scans the genetic information encoded along the mRNA. [*Biochemistry* vol 41, 4503-4510 (2002); *Cancer Res.* vol 48, 2659-2668 (1988)]

Antisense Oligonucleotide: An oligonucleotide binding to RNA in a sequence specific manner (i.e. complementarily) is called antisense oligonucleotide (ASO). ASO may tightly bind to an mRNA or a pre-mRNA.

An ASO tightly binding to an mRNA can inhibit the protein synthesis by ribosome along the mRNA in the cytosol. The ASO needs to be present within the cytosol in order to inhibit the ribosomal protein synthesis of its target protein.

In order for an ASO tightly binding to a pre-mRNA to interfere with the splicing process of the pre-mRNA, the ASO needs to be present in the nucleus to alter the splicing process.

Unnatural Oligonucleotides: DNA or RNA oligonucleotide is susceptible to degradation by endogenous nucleases, limiting their therapeutic utility. To date, many types of unnatural (i.e. naturally non-occurring) oligonucleotides have been developed and studied intensively. [*Clip. Exp. Pharmacol. Physiol.* vol 33, 533-540 (2006)] Many of them show extended metabolic stability compared to DNA and RNA. Provided below are the chemical structures for a few of representative unnatural oligonucleotides. Such oligonucleotides predictably bind to a complementary nucleic acid as DNA or RNA does.

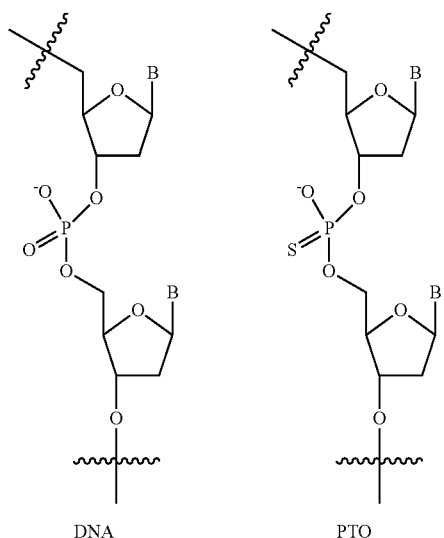

DNA            PTO

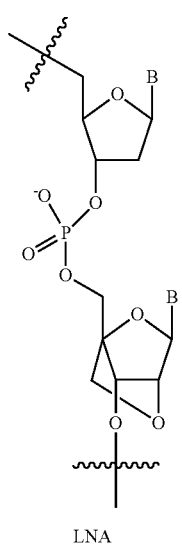

LNA

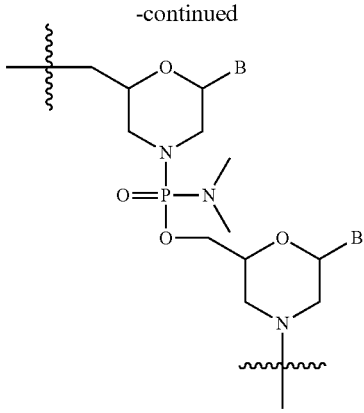

PMO

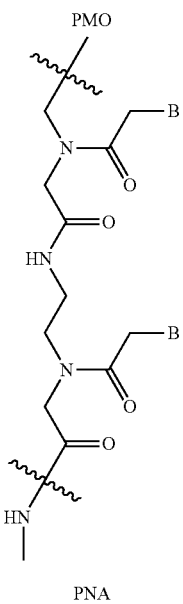

PNA

B : Nucleobase

Phosphorothioate Oligonucleotide: Phosphorothioate oligonucleotide (PTO) is a DNA analog with one of the backbone phosphate oxygen atoms replaced with a sulfur atom per monomer. Such a small structural change made PTO resistant to degradation by nucleases. [*Ann. Rev. Biochem.* vol 54, 367-402 (1985)]

Reflecting the structural similarity of the backbone between PTO and DNA, they both poorly penetrate cell membrane in most mammalian cell types. For some types of cells abundantly expressing transporter(s) for DNA, however, DNA and PTO show good cell penetration. Systemically administered PTOs are known to readily distribute to the liver and kidney. [*Nucleic Acids Res.* vol 25, 3290-3296 (1997)] In order to improve PTO's cell penetration in vitro, lipofection has been widely used. However, lipofection physically alters cell membrane, causes cytotoxicity, and therefore would not be ideal for chronic therapeutic use.

Over the past 30 years, antisense PTOs and variants of PTOs have been clinically evaluated to treat cancers, immunological disorders, metabolic diseases, and so on. [*Biochemistry* vol 41, 4503-4510 (2002); *Clin. Exp. Pharmacol. Physiol.* vol 33, 533-540 (2006)] Most of such antisense drug candidates have not been successfully developed partly due to PTO's poor cell penetration. In order to overcome the poor cell penetration, PTO needs to be administered at high dose for therapeutic activity. However, PTOs are known to induce dose-limiting toxicity including increased coagulation time, complement activation, tubular nephropathy, Kupffer cell activation, and immune stimulation including splenomegaly, lymphoid hyperplasia, mononuclear cell infiltration. [*Clip. Exp. Pharmacol. Physiol.* vol 33, 533-540 (2006)]

Many antisense PTOs have been found to show clinical activity for diseases with a significant contribution from the liver or kidney. Mipomersen is a PTO analog which inhibits the synthesis of apoB-100, a protein involved in LDL cholesterol transport. Mipomersen manifested therapeutic activity in a certain population of atherosclerosis patients most likely due to its preferential distribution to the liver. [*Circulation* vol 118(7), 743-753 (2008)] ISIS-113715 is a PTO antisense analog inhibiting the synthesis of protein tyrosine phosphatase 1B (PTP1B), and was found to show therapeutic activity in type II diabetes patients. [*Curr. Opin. Mol. Ther.* vol 6, 331-336 (2004)]

Locked Nucleic Acid: In locked nucleic acid (LNA), the backbone ribose ring of RNA is structurally constrained to increase the binding affinity for RNA or DNA. Thus, LNA may be regarded as a high affinity DNA or RNA analog. [*Biochemistry* vol 45, 7347-7355 (2006)]

Phosphorodiamidate Morpholino Oligonucleotide: In phosphorodiamidate morpholino oligonucleotide (PMO), the backbone phosphate and 2-deoxyribose of DNA are replaced with phosphoamidate and morpholine, respectively. [*Appl. Microbiol. Biotechnol.* vol 71, 575-586 (2006)] Whilst the DNA backbone is negatively charged, the PMO backbone is not charged. Thus the binding between PMO and mRNA is free of electrostatic repulsion between the backbones, and tends to be stronger than that between DNA and mRNA. Since PMO is structurally very different from DNA, PMO wouldn't be recognized by the hepatic transporter(s) recognizing DNA or RNA. However, PMO doesn't readily penetrate cell membrane.

Peptide Nucleic Acid: Peptide nucleic acid (PNA) is a polypeptide having N-(2-aminoethyl)glycine as the unit backbone, and was discovered by Dr. Nielsen and colleagues. [*Science* vol 254, 1497-1500 (1991)] The chemical structure and abbreviated nomenclature of PNA are illustrated with the drawing provided below. Like DNA and RNA, PNA also selectively binds to complementary nucleic acid. [*Nature (London)* vol 365, 566-568 (1992)] In binding to complementary nucleic acid, the N-terminus of PNA is regarded as equivalent to the "5'-end" of DNA or RNA, and the C-terminus of PNA as equivalent to the "3'-end" of DNA or RNA.

Like PMO, the PNA backbone is not charged. Thus the binding between PNA and RNA tends to be stronger than that between DNA and RNA. Since PNA is markedly different from DNA in the chemical structure, PNA wouldn't be recognized by the hepatic transporter(s) recognizing DNA, and would show a tissue distribution profile different from that of DNA or PTO. Nevertheless PNA also poorly penetrates mammalian cell membrane. (*Adv. Drug Delivery Rev.* vol 55, 267-280, 2003)

Modified Nucleobases to Improve Membrane Permeability of PNA: PNA was made highly permeable to mammalian cell membrane by introducing modified nucleobases with a cationic lipid or its equivalent covalently attached thereto. The chemical structures of such modified nucleobases are provided below. Such modified nucleobases of cytosine, adenine, and guanine were found to predictably and complementarily hybridize with guanine, thymine, and cytosine, respectively. [PCT Appl. No. PCT/KR2009/001256; EP2268607; US8680253]

Incorporation of such modified nucleobases onto PNA simulates situations of lipofection. During lipofection, oligonucleotide molecules are wrapped or doped with cationic lipid molecules such as lipofectamine, and such lipofectamine/oligonucleotide complexes penetrate membrane rather easily as compared to naked oligonucleotide molecules.

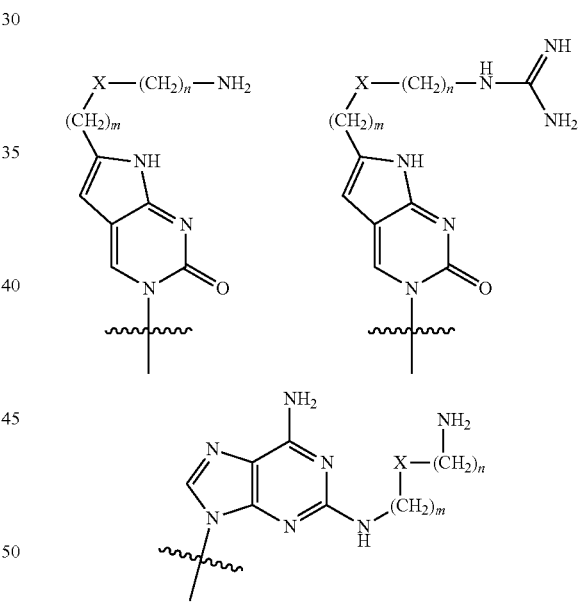

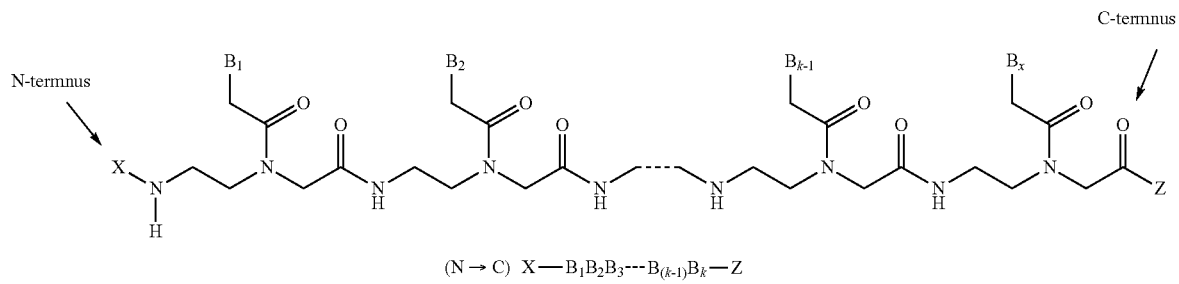

$(N \rightarrow C)\ X\text{---}B_1B_2B_3\text{---}B_{(k-1)}B_k\text{---}Z$

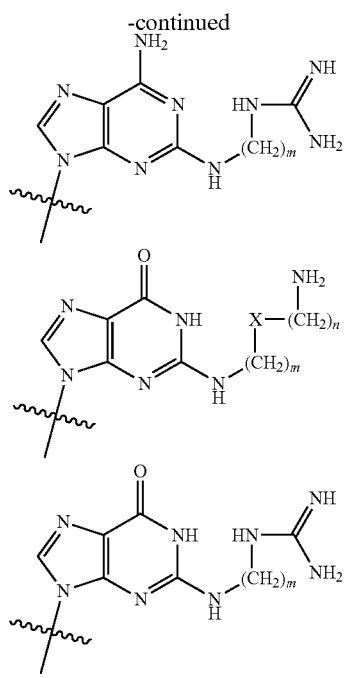

X = CH$_2$, O, S, or NH
m = integer
n = integer

In addition to good membrane permeability, those PNA derivatives were found to possess extremely strong affinity for complementary nucleic acid. For example, introduction of 4 to 5 modified nucleobases onto 11- to 13-mer PNA derivatives easily yielded a T$_m$ gain of 20° C. or higher in duplex formation with complementary DNA. Such PNA derivatives are highly sensitive to a single base mismatch. A single base mismatch resulted in a T$_m$ loss of 11 to 22° C. depending on the type of modified base as well as PNA sequence.

HIF-1α ASO: In contrast to small molecule inhibitors of HIF-1α, ASOs complementarily targeting the HIF-1α mRNA may selectively inhibit the ribosomal synthesis of the HIF-1α protein in a sequence specific manner A couple of 25-mer morpholino (PMO) HIF-1α ASOs were evaluated for their ability to inhibit the translation of an artificially constructed human HIF-1α mRNA in *Xenopus*. 40 ng of each morpholino ASO was microinjected into a *Xenopus* embryo, and was found to inhibit the HIF-1α expression. [*J. Biol. Chem.* vol 283(17), 11841-11849 (2008)]

RX-0047 is a potent HIF-1α PTO ASO. RX-0047 was evaluated for its HIF-1α inhibitory activity in various cell lines. Upon lipofection into cells such as MDA-MB-231, PC3, and A549, RX-0047 inhibited the expression of the HIF-1α protein with an in vitro IC$_{50}$'s of 1.9~4 nM. Also RX-0047 inhibited the expression of HIF-1α mRNA in UMRC2 cells in a sequence specific manner Intra-peritoneal injections of RX-0047 at 30 mg/Kg inhibited the lung metastasis of A549 cells in mice. Also RX-0047 at 30 mg/Kg inhibited tumor growth in a xenograft model in nude mice. [*J. Cell. Biochem.* vol 104, 985-994 (2008)]

EZN-2968 is a locked nucleic acid (LNA) derivative complementarily targeting a coding region of the human HIF-1α mRNA. EZN-2968 induces cleavage of the HIF-1α mRNA by RNAse H and consequently inhibits the expression of HIF-1α protein in vivo as well as in cells. Tumor growth (DU145 xenograft) was significantly inhibited in nude mice intra-peritoneally receiving EZN-2968 at 50 mg/Kg, two times per week. [*Mol. Cancer Ther.* vol 7(11), 3598-3608 (2008)]

EZN-2968 was evaluated in a small number of cancer patients with refractory advanced solid tumors. EZN-2968 was administered once per week by intravenous infusion at 18 mg/Kg. The HIF-1α mRNA level decreased in 4 out of 6 patients evaluated by tumor biopsy, although the clinical trial was terminated prematurely by the sponsor. [*Cancer Chemother. Pharmacol.* vol 73(2), 343-348 (2014)]

EZN-2968 is a very rare example of HIF-1α ASO that was evaluated in human cancer patients. Like other oligonucleotide therapeutics, the therapeutic dose of EZN-2968 is considered to be still high due to its limited cell permeability. There is a strong necessity to improve the cell permeability of oligonucleotide therapeutics targeting HIF-1α in order to overcome the dose limiting toxicity of oligonucleotide therapeutics with DNA or RNA backbone.

Small Interfering RNA (siRNA): Small interfering RNA (siRNA) refers to a double stranded RNA of 20-25 base pairs. [*Microbiol. Mol. Biol. Rev.* vol 67(4), 657-685 (2003)] The antisense strand of siRNA somehow interacts with proteins to form a RNA-induced silencing complex (RISC). Then the RISC binds to a certain portion of mRNA complementary to the antisense strand of siRNA. The mRNA complexed with RISC undergoes cleavage. Thus siRNA catalytically induces the cleavage of its target mRNA, and consequently inhibits the protein expression by the mRNA. The RISC does not always bind to the full complementary sequence within its target mRNA, which raises concerns relating to off-target effects of a siRNA therapy. Like other classes of oligonucleotide with DNA or RNA backbone, siRNA possesses poor cell permeability and therefore tends to show poor in vitro or in vivo therapeutic activity unless properly formulated or chemically modified to show good membrane permeability.

HIF-1α siRNA: There are abundant examples of HIF-1α siRNAs down-regulating HIF-1α expression in cells. However, the in vitro inhibitory activity was usually observed in cases siRNA molecules were effectively delivered into cell. For instance, a HIF-1α siRNA was transfected at 100 nM into HCT116 cells by lipofection, and found to induce a marked decrease in the HIF-1α mRNA as well as the HIF-1α protein under hypoxia. The siRNA also induced changes in the expression level of HIF-1 target proteins or mRNAs such as VEGF, TGF-α, and so on. [*Cancer Res.* vol 63, 1138-1143 (2003)]

U251MG and U343MG glioma cells were transfected with 75 nM HIF-1α siRNA by lipofection. HIF-1α expression significantly decreased in cells treated with the HIF-1α siRNA, regardless of hypoxia or nomoxia. [*BMC Cancer* 10:605 (2010)]

Cationic micellar nanoparticles of an siRNA targeting the human HIF-1α mRNA markedly inhibited tumor growth in mice with PC3 xenograft. Also, co-treatment of the nanoparticles of the HIF-1α siRNA with doxorubicin induced additional antitumor activity in the PC3 xenograft model. [*Mol. Pharmaceutics* vol 9(10), 2863-2874 (2012)]

Nanoparticles of a HIF-1α siRNA and RGD-targeted multifunctional lipid ECO were evaluated for the antitumor and anti-angiogenic activity in mice with HT-29 colon cancer xenograft. The formulated HIF-1α siRNA was intravenously administered at 2 mg/Kg, every 3 days for 3 weeks, and was found to inhibit tumor growth by 50%. MRI evaluation suggested a significant decline in the vascularity in tumor, and a 70% decrease in the intra-tumoral blood flow. There was a significant reduction in the HIF-1α expression, and also in related proteins such as VEGF, GLUT-1, and CA9 (carbonic anhydrase 9). [*Mol. Pharmaceutics* vol 13(7), 2497-2506 (2016)]

Splicing of Pre-mRNA: DNA is transcribed to produce pre-mRNA (pre-messenger ribonucleic acid) in the nucleus. Pre-mRNA is then processed into mRNA following deletion of introns by a series of complex reactions collectively called "splicing" as schematically summarized in the diagram shown in FIG. 13. [*Ann. Rev. Biochem.* 72(1), 291-336 (2003); *Nature Rev. Mol. Cell Biol.* 6(5), 386-398 (2005); *Nature Rev. Mol. Cell Biol.* 15(2), 108-121 (2014)]

Splicing is initiated by forming "splicesome E complex" (i.e. early splicesome complex) between pre-mRNA and splicing adapter factors. In "splicesome E complex", U1 binds to the junction of exon N and intron N, and U2AF$^{35}$ binds to the junction of intron N and exon (N+1). Thus the junctions of exon/intron or intron/exon are critical to the formation of the early splicesome complex. "Splicesome E complex" evolves into "splicesome A complex" upon additional complexation with U2. The "splicesome A complex" undergoes a series of complex reactions to delete or splice out the intron to adjoin the neighboring exons.

Antisense Inhibition of Splicing: In the nucleus, ASO may tightly bind to a certain position within a pre-mRNA, and can interfere with the splicing process of the pre-mRNA into the mRNA, producing an mRNA or mRNAs lacking the target exon. Such mRNA(s) is called "splice variant(s)", and encodes protein(s) of different structure than the protein encoded by the full-length mRNA.

In principle, splicing can be interrupted by inhibiting the formation of "splicesome E complex". If an ASO tightly binds to a junction of (5'→3') exon-intron, i.e., "5' splice site", the ASO blocks the complex formation between pre-mRNA and factor U1, and therefore the formation of "splicesome E complex". Likewise, "splicesome E complex" cannot be formed if an ASO tightly binds to a junction of (5'→3') intron-exon, i.e. "3' splice site".

Antisense Exon Skipping of HIF-1α Pre-mRNA: To date, there are no reported cases of antisense oligonucleotides inhibiting a splicing process of HIF-1α pre-mRNA to induce exon skipping.

SUMMARY

The present invention provides a peptide nucleic acid derivative represented by Formula I, or a pharmaceutically acceptable salt thereof:

the 14-mer RNA sequence of [(5'→3') UAAGUAG-GAUAAGU (SEQ ID NO: 2)] in the human HIF-1α pre-mRNA;

$S_1, S_2, \ldots, S_{n-1}, S_n, T_1, T_2, \ldots, T_{n-1},$ and $T_n$, independently represent deuterido, hydrido, substituted or non-substituted alkyl, or substituted or non-substituted aryl radical;

X and Y independently represent hydrido [H], formyl [H—C(=O)—], aminocarbonyl [NH$_2$—C(=O)—], substituted or non-substituted alkyl, substituted or non-substituted acyl, substituted or non-substituted sulfonyl, substituted or non-substituted aryl, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylsulfonyl, or substituted or non-substituted arylsulfonyl radical;

Z represents hydrido, hydroxy, substituted or non-substituted alkyloxy, substituted or non-substituted aryloxy, substituted or non-substituted amino, substituted or non-substituted alkylamino, substituted or non-substituted arylamino, substituted or non-substituted alkyl, or substituted or non-substituted aryl radical;

$B_1, B_2, \ldots, B_{n-1},$ and $B_n$ are independently selected from natural nucleobases including adenine, thymine, guanine, cytosine and uracil, and unnatural nucleobases; and at least three (preferably at least four) of $B_1, B_2, \ldots, B_{n-1}$, and $B_n$ are independently selected from unnatural nucleobases with a substituted or non-substituted amino radical covalently linked to the nucleobase moiety.

In some embodiments, $S_1, S_2, \ldots, S_{n-1}, S_n, T_1, T_2, \ldots, T_{n-1},$ and $T_n$ independently represent hydrido, substituted or non-substituted alkyl, or substituted or non-substituted aryl radical.

In some embodiments, X and Y independently represent hydrido [H], substituted or non-substituted alkyl, substituted or non-substituted acyl, substituted or non-substituted sulfonyl, or substituted or non-substituted aryl radical. In other embodiments, X and Y independently represent hydrido [H], formyl [H—C(=O)—], aminocarbonyl [NH$_2$—C(=O)—], substituted or non-substituted alkyl, substituted or non-substituted aryl, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbo-

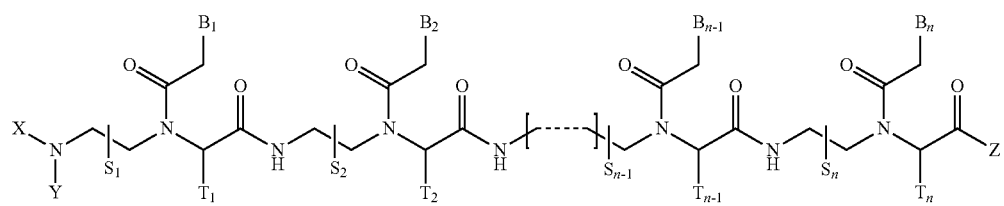

Formula I wherein, n is an integer between 10 and 26;

the compound of Formula I possesses at least a 10-mer complementary overlap with a 20-mer RNA sequence [(5'→3') UGUUAAGUAGGAUAAGUUCU (SEQ ID NO: 1)], a part of the human HIF-1α pre-mRNA, preferably with nyl, substituted or non-substituted alkylsulfonyl, or substituted or non-substituted arylsulfonyl radical.

In some embodiments, Z represents hydrido, hydroxy, substituted or non-substituted alkyloxy, substituted or non-substituted aryloxy, substituted or non-substituted amino, substituted or non-substituted alkyl, or substituted or non-substituted aryl radical. In other embodiments, Z represents hydroxy, substituted or non-substituted alkyloxy, substituted or non-substituted aryloxy, amino, substituted or non-substituted alkylamino, or substituted or non-substituted arylamino, substituted or non-substituted alkyl, or substituted or non-substituted aryl radical.

In some embodiments, the compound of Formula I is fully complementary to the target HIF-1α pre-mRNA sequence. In other embodiments, the compound of Formula I is partially complementary to the target HIF-1α pre-mRNA sequence, e.g., having one or two mismatches with the target HIF-1α pre-mRNA sequence.

The compound of Formula I induces alternative splicing of the human HIF-1α pre-mRNA, yields HIF-1α mRNA splice variant(s) lacking "exon 2", and is useful to treat solid tumors or conditions involving HIF-1α activity.

BRIEF DESCRIPTION OF FIGURES

FIG. 3C. Sanger sequencing data for the PCR product band assigned to the skipping of exon 2. FIG. 3C discloses from top to bottom three nucleic acid sequences which are identical and set forth in SEQ ID NO: 23.

DETAILED DESCRIPTION

Figure 1A:
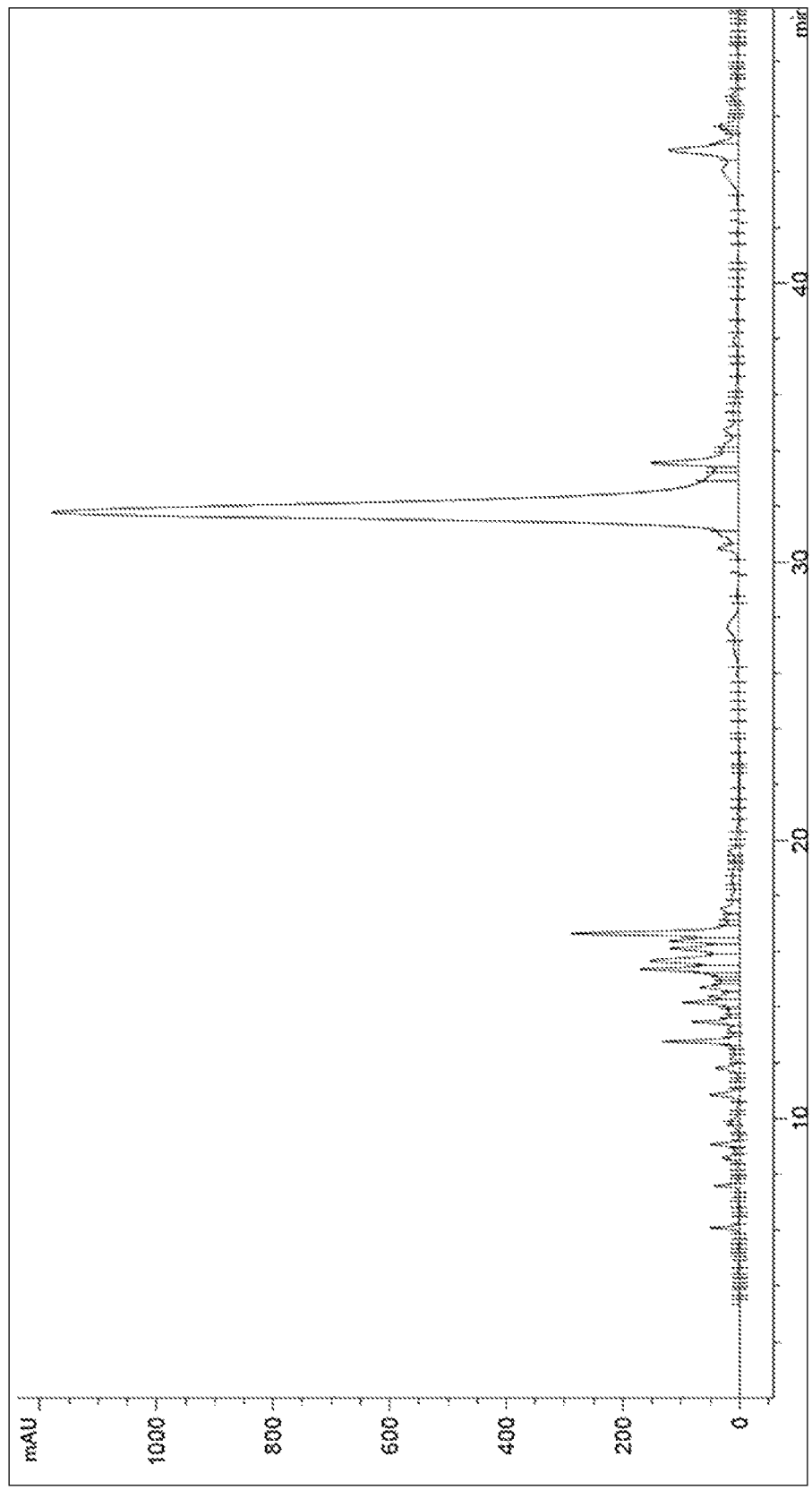
FIG. 1A. $C_{18}$-reverse phase HPLC chromatogram of "ASO 1" before preparatory HPLC purification.

The present invention provides a peptide nucleic acid derivative represented by Formula I, or a pharmaceutically acceptable salt thereof:

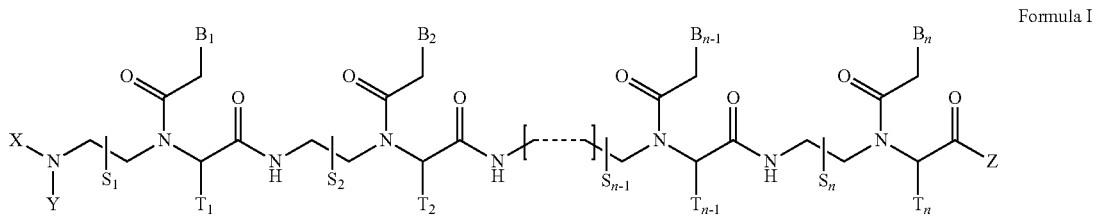

Formula I wherein, n is an integer between 10 and 26;

the compound of Formula I possesses at least a 10-mer complementary overlap with a 20-mer RNA sequence [(5'→3') UGUUAAGUAGGAUAAGUUCU (SEQ ID NO: 1)], a part of the human HIF-1α pre-mRNA, preferably with the 14-mer RNA sequence of [(5'→3') UAAGUAGGAUAAGU (SEQ ID NO: 2)] in the human HIF-1α pre-mRNA;

$S_1, S_2, \ldots, S_{n-1}, S_n, T_1, T_2, \ldots, T_{n-1},$ and $T_n$ independently represent deuterido, hydrido, substituted or non-substituted alkyl, or substituted or non-substituted aryl radical;

X and Y independently represent hydrido [H], formyl [H—C(=O)—], aminocarbonyl [NH$_2$—C(=O)—], substituted or non-substituted alkyl, substituted or non-substituted acyl, substituted or non-substituted sulfonyl, substituted or non-substituted aryl, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylsulfonyl, or substituted or non-substituted arylsulfonyl radical;

Z represents hydrido, hydroxy, substituted or non-substituted alkyloxy, substituted or non-substituted aryloxy, substituted or non-substituted amino, substituted or non-substituted alkylamino, substituted or non-substituted arylamino, substituted or non-substituted alkyl, or substituted or non-substituted aryl radical;

$B_1, B_2, \ldots, B_{n-1},$ and $B_n$ are independently selected from natural nucleobases including adenine, thymine, guanine, cytosine and uracil, and unnatural nucleobases; and at least three (preferably at least four) of $B_1, B_2, \ldots, B_{n-1},$ and $B_n$ are independently selected from unnatural nucleobases with a substituted or non-substituted amino radical covalently linked to the nucleobase moiety.

In some embodiments, $S_1, S_2, \ldots, S_{n-1}, S_n, T_1, T_2, \ldots, T_{n-1},$ and $T_n$ independently represent hydrido, substituted or non-substituted alkyl, or substituted or non-substituted aryl radical.

In some embodiments, X and Y independently represent hydrido [H], substituted or non-substituted alkyl, substituted or non-substituted acyl, substituted or non-substituted sulfonyl, or substituted or non-substituted aryl radical. In other embodiments, X and Y independently represent hydrido [H], formyl [H—C(=O)—], aminocarbonyl [NH$_2$—C(=O)—], substituted or non-substituted alkyl, substituted or non-substituted aryl, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylsulfonyl, or substituted or non-substituted arylsulfonyl radical.

In some embodiments, Z represents hydrido, hydroxy, substituted or non-substituted alkyloxy, substituted or non-substituted aryloxy, substituted or non-substituted amino, substituted or non-substituted alkyl, or substituted or non-substituted aryl radical. In other embodiments, Z represents hydroxy, substituted or non-substituted alkyloxy, substituted or non-substituted aryloxy, amino, substituted or non-substituted alkylamino, or substituted or non-substituted arylamino, substituted or non-substituted alkyl, or substituted or non-substituted aryl radical.

In some embodiments, the compound of Formula I is fully complementary to the target HIF-1α pre-mRNA sequence.

In other embodiments, the compound of Formula I is partially complementary to the target HIF-1α pre-mRNA sequence, e.g., having one or two mismatches with the target HIF-1α pre-mRNA sequence.

The compound of Formula I induces alternative splicing of the human HIF-1α pre-mRNA, yields HIF-1a mRNA splice variant(s) lacking "exon 2", and is useful to treat solid tumors or conditions involving HIF-1α activity.

The description that "n is an integer between 10 and 26" literally states that n is an integer selectable from a group of integers of 11, 12, 13, 14, 15, 16, 17, 18, 19, 20, 21, 22, 23, 24, and 25.

The compound of Formula I tightly binds to the 3' splice site of "exon 2" of the human HIF-1α pre-mRNA accessed from the human HIF-1α gene (NCBI Reference Sequence: NG_029606.1). A 20-mer HIF-1α pre-mRNA sequence consisting of a 10-mer from "intron 1" and a 10-mer from "exon 2" reads [(5'→3') UGUUAAGUAGGAUAAGUUCU (SEQ ID NO: 1)], although the numbering of exons and introns may vary depending on reported HIF-1α mRNA transcripts. Provision of the 20-mer pre-mRNA sequence is to unequivocally identify the target 3' splice site within the human HIF-1α pre-mRNA.

The 20-mer pre-mRNA sequence may be alternatively expressed as [(5'→3') uguuaaguag|GAUAAGUUCU (SEQ ID NO: 1)], wherein the intron and exon sequences are denoted with "small" and "capital" letters, respectively, and the junction between the intron and exon is marked with "|". Thus the 14-mer pre-mRNA sequence of [(5'→3') UAAGUAGGAUAAGU (SEQ ID NO: 2)] adopted to describe the compound of Formula I in this invention may be alternatively expressed as [(5'→3') uaaguag|GAUAAGU (SEQ ID NO: 2)].

The compound of Formula I tightly binds to the target 3' splice site of "exon 2" within the human HIF-1α pre-mRNA, and interferes with the formation of the "splicesome early complex" involving the compound's target splice site. Since the said compound sterically inhibits the formation of the "splicesome early complex" involving the target splice site, the HIF-1α "exon 2" is spliced out or deleted to yield a HIF-1α mRNA splice variant or variants lacking "exon 2". Consequently the compound of this invention is said to induce the skipping of the HIF-1α "exon 2". The resulting HIF-1α mRNA splice variant(s) encodes HIF-1α variant protein(s) lacking the HIF-1α functional activity expressed by the full-length HIF-1α protein.

The compound of Formula I tightly binds to the complementary DNA as exemplified in the prior art [PCT/KR2009/001256]. The duplex between the PNA derivative of Formula I and its full-length complementary DNA or RNA shows a $T_m$ value too high to be reliably determined in aqueous buffer. The buffer solution tends to boil off during a $T_m$ measurement. The PNA compound of Formula I still yields high $T_m$ values with complementary DNAs of shorter length, for example, 10-mer. Owing to the high binding affinity, the PNA derivative of this invention potently induces the skipping of HIF-1α "exon 2" in cells even with a complementary overlap of as small as 10-mer with the 3' splice site of "exon 2".

The said compound possesses a very strong affinity for the target HIF-1α pre-mRNA sequence with full complementarity. Even in case the compound of Formula I has one or two mismatches with the target HIF-1α pre-mRNA sequence, the PNA compound may still tightly bind to the target pre-mRNA sequence and interrupts the splicing process since the affinity between the said compound and the target HIF-1α pre-mRNA sequence is strong enough despite the mismatch(es). Even if a 14-mer PNA derivative of Formula I possesses only a 12-mer complementary overlap with a 14-mer HIF-1α pre-mRNA sequence of, for example, [(5'→3') aaguag|GAUAAGUU (SEQ ID NO: 3)], and the 14-mer compound is still able to induce the skipping of the HIF-1α "exon 2" despite the two mismatches with the target pre-mRNA 14-mer sequence. Nevertheless, it would not be desired to have too many mismatches with the target pre-mRNA sequence in order to avoid off-target engagement with other pre-mRNAs.

The chemical structures of natural or unnatural nucleobases useful in the PNA derivative of Formula I are exemplified below.

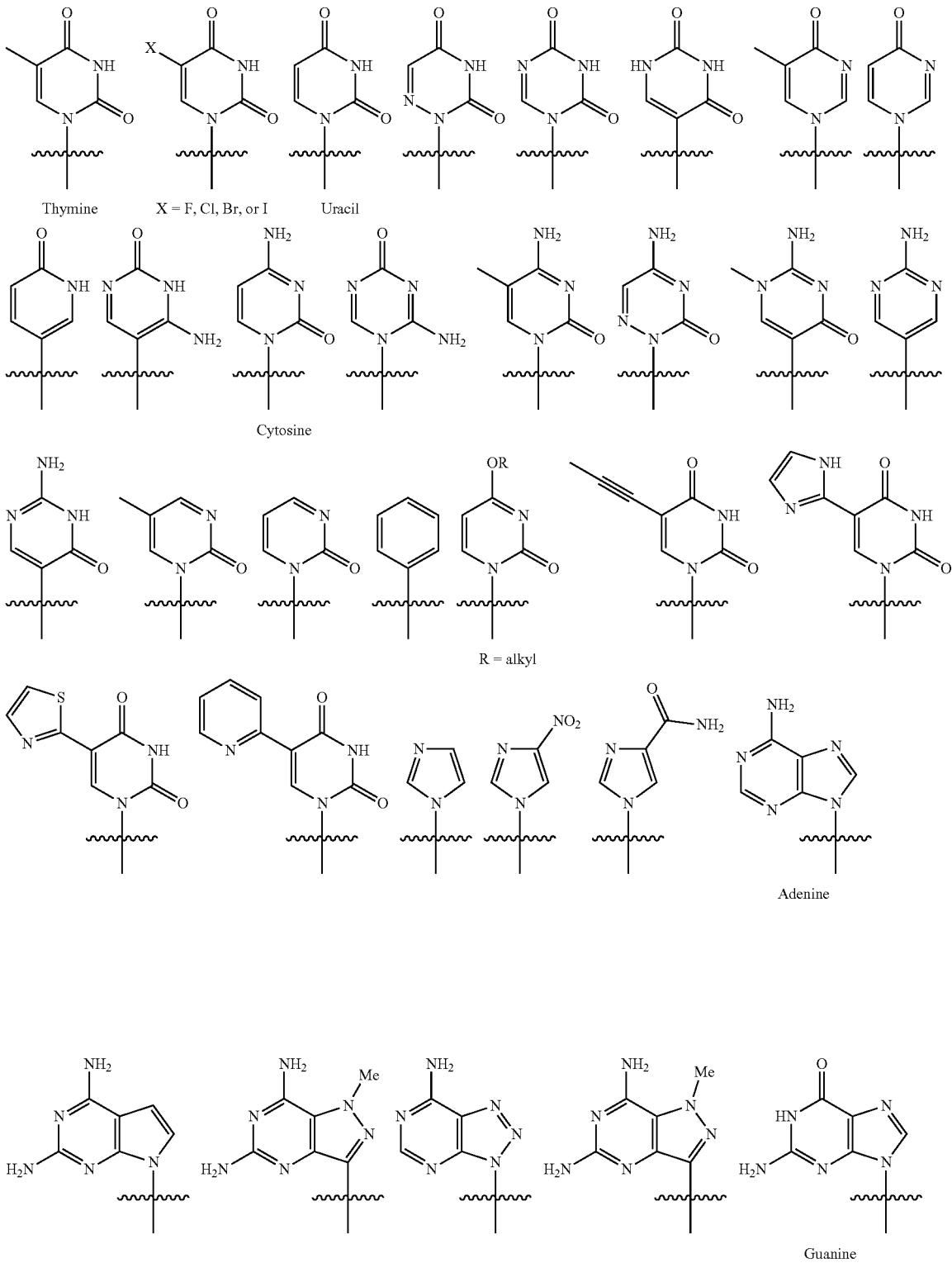

-continued
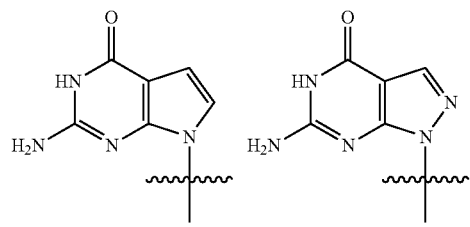 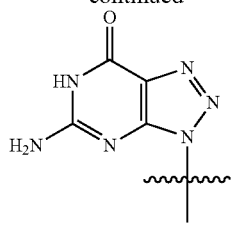 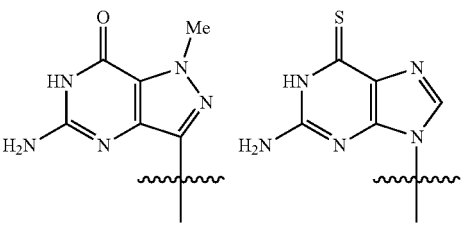
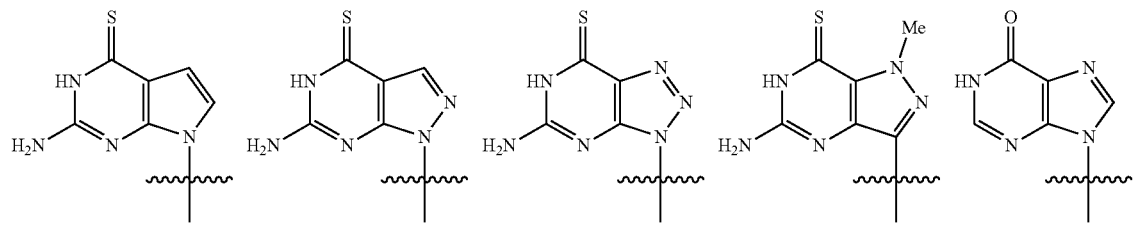
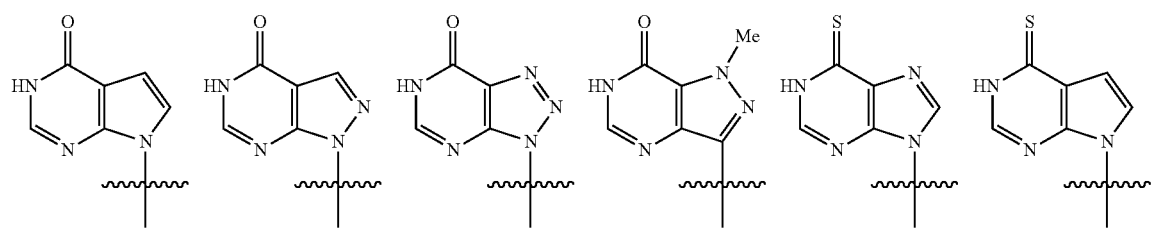
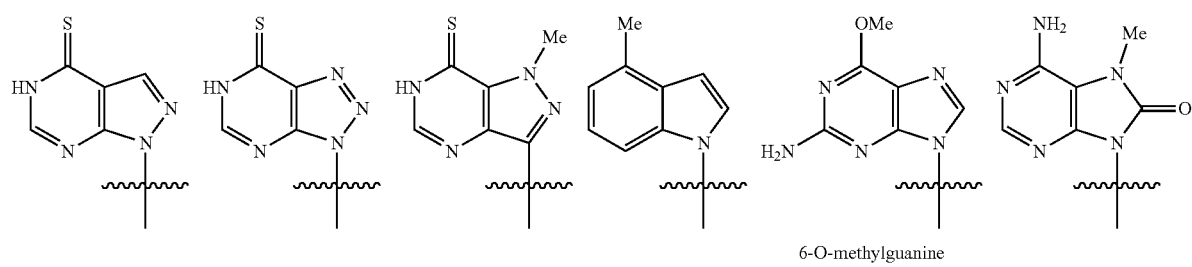
6-O-methylguanine
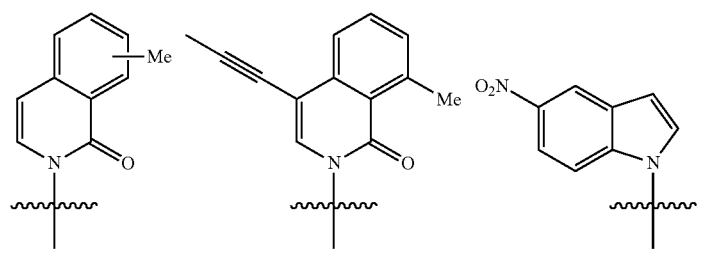

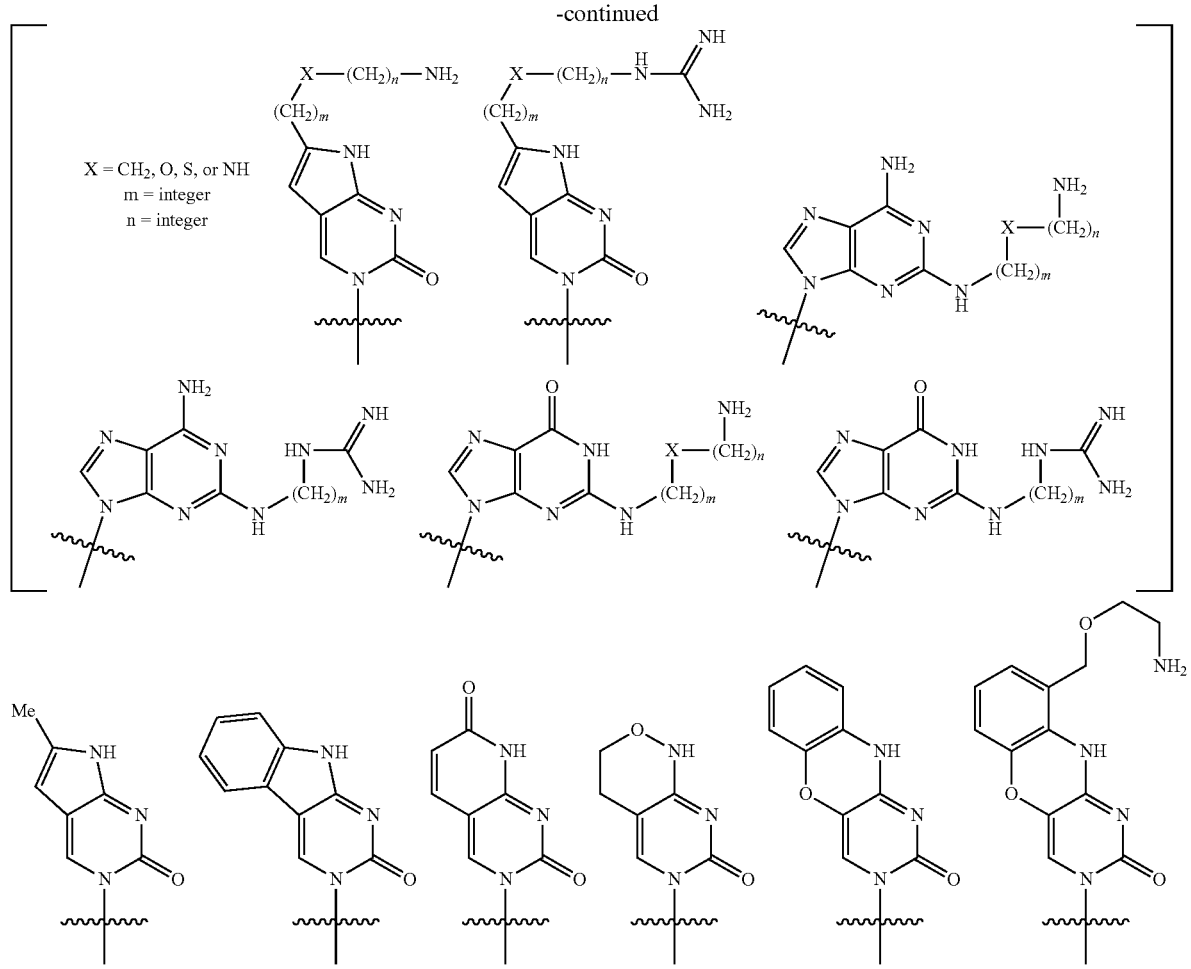

Natural (conventionally expressed as "naturally occurring") or unnatural (conventionally expressed as "naturally non-occurring") nucleobases of this invention comprise but are not limited to the nucleobases provided above. Provision of such natural or unnatural nucleobases is to illustrate the diversity of nucleobases allowable for the compound of Formula I, and therefore should not be interpreted to limit the scope of the present invention. A skilled person in the field may easily figure out that variations of natural or unnatural nucleobases are possible for specific positions within the PNA compound of Formula I as long as such variations meet the conditions of complementarity with the target pre-mRNA sequence of this invention.

The substituents adopted to describe the PNA derivative of Formula I are exemplified herein. Examples for substituted or non-substituted alkyl radicals are provided below.

Examples of Non-substituted Alkyl Radical

Examples of Substituted Alkyl Radical

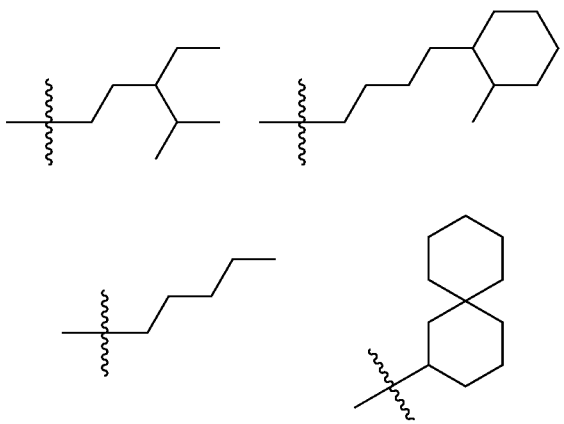

-continued

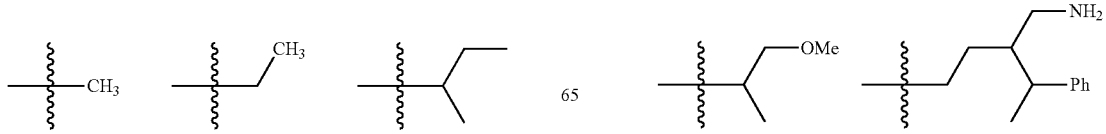

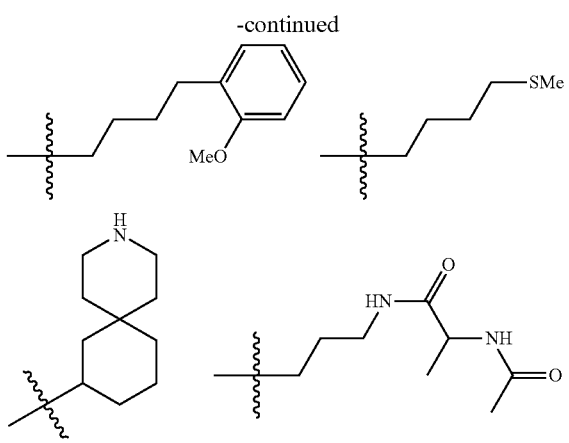
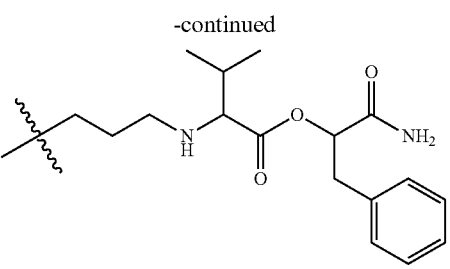
Substituted or non-substituted alkylacyl and substituted or non-substituted arylacyl radicals are exemplified below.
Examples of Non-substituted Alkylacyl Radical
Examples of Substituted Alkylacyl Radical
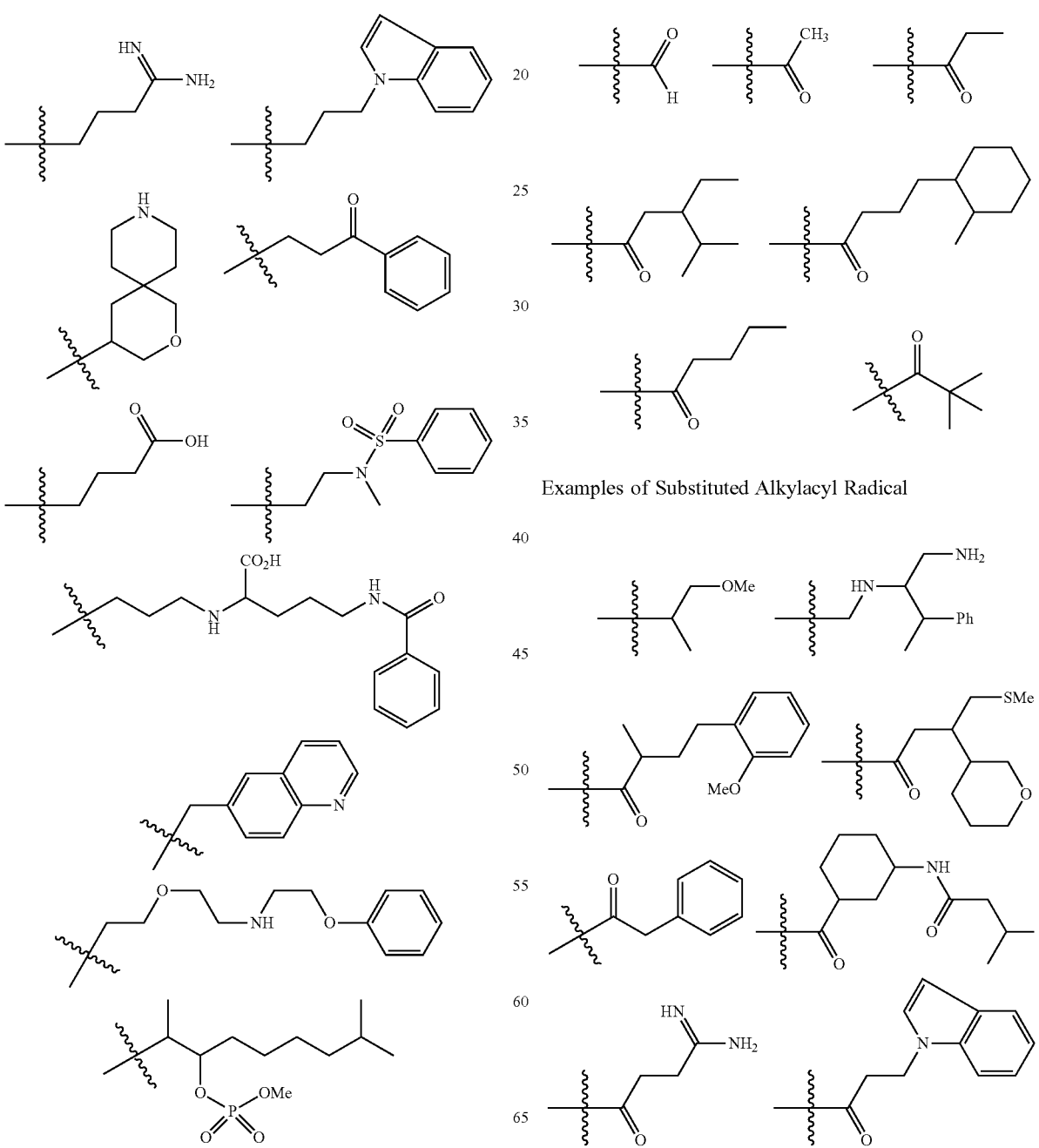

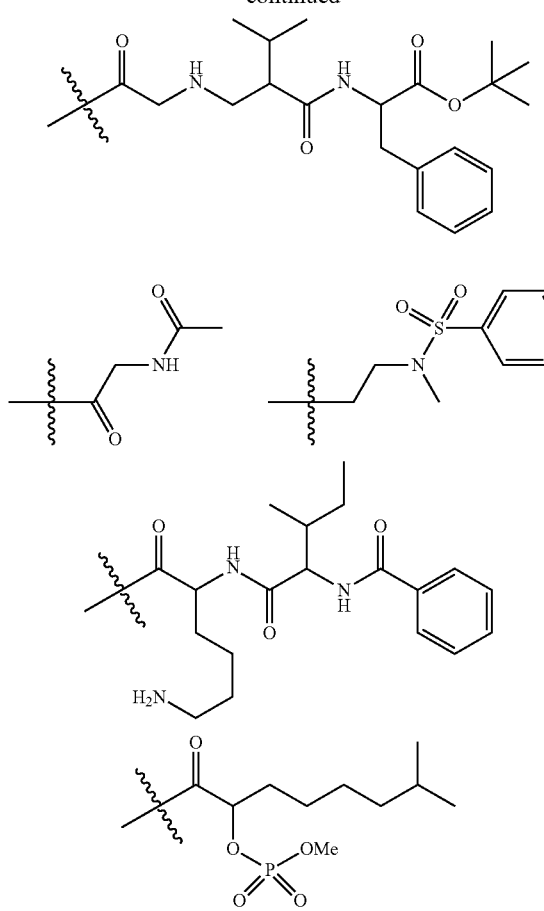

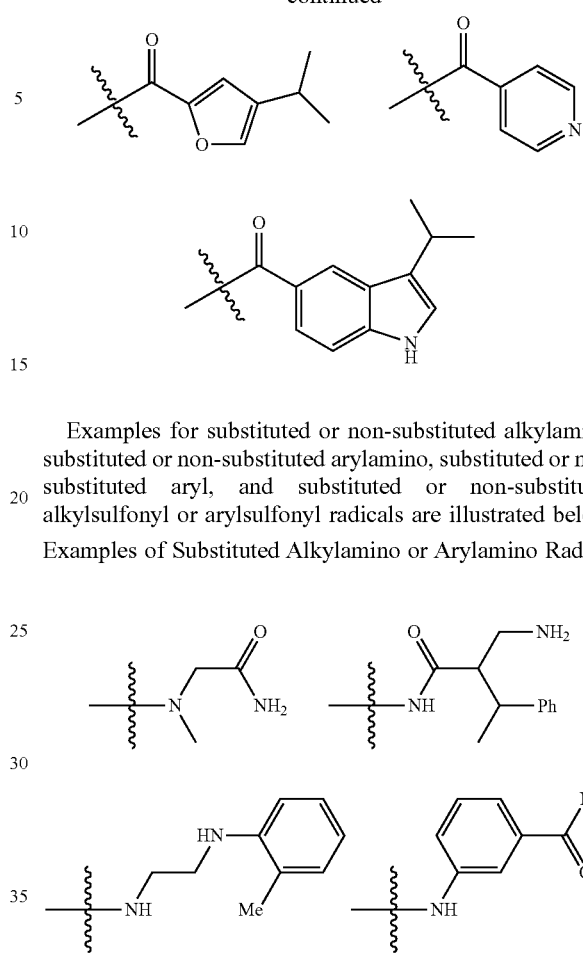

Examples for substituted or non-substituted alkylamino, substituted or non-substituted arylamino, substituted or non-substituted aryl, and substituted or non-substituted alkylsulfonyl or arylsulfonyl radicals are illustrated below.

Examples of Substituted Alkylamino or Arylamino Radical

Examples of Substituted or Non-substituted Arylacyl Radical

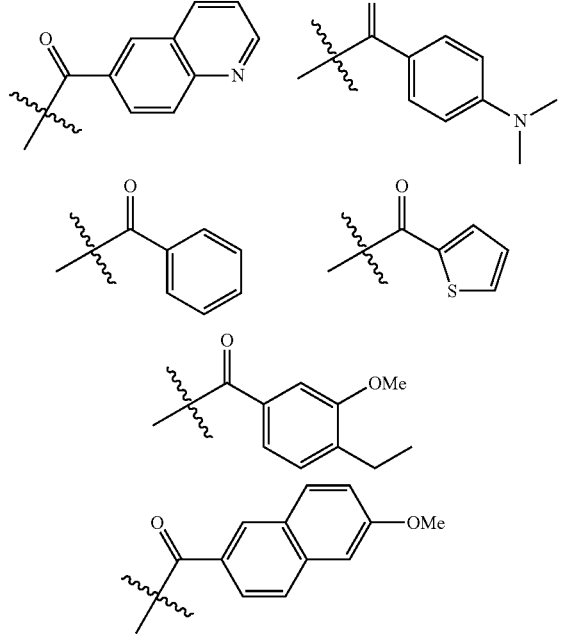

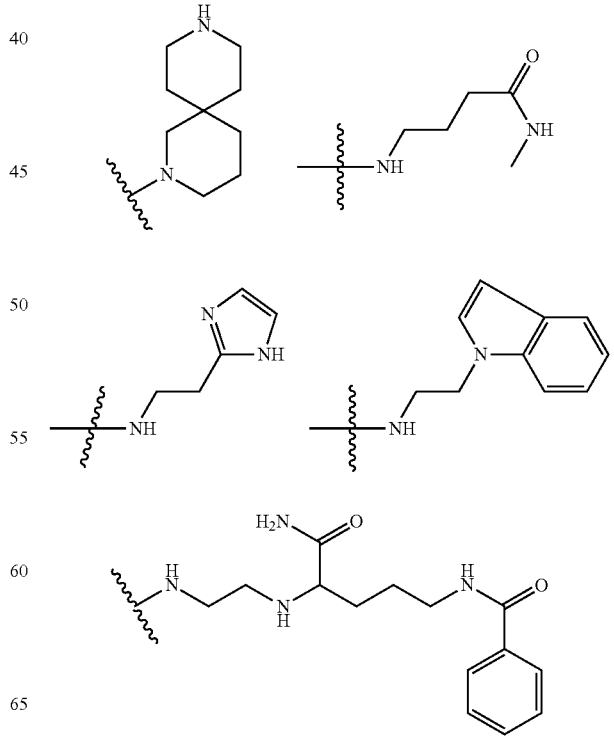

-continued

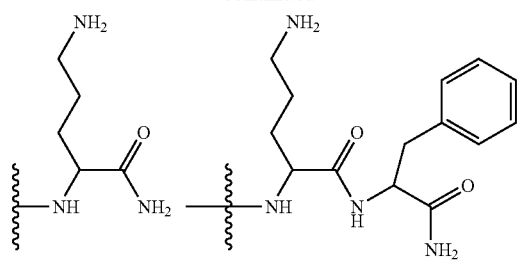

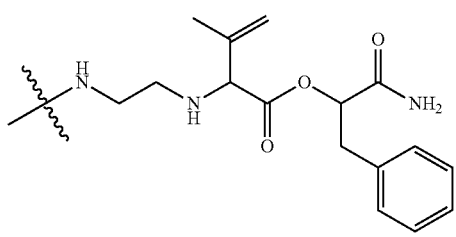

Examples of Substituted or Non-substituted Aryl Radical

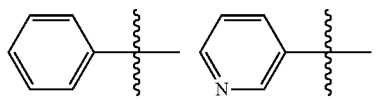

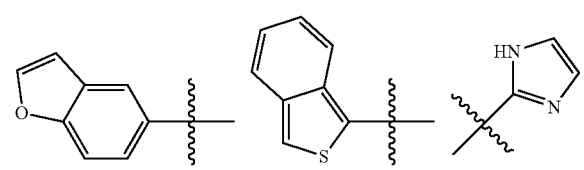

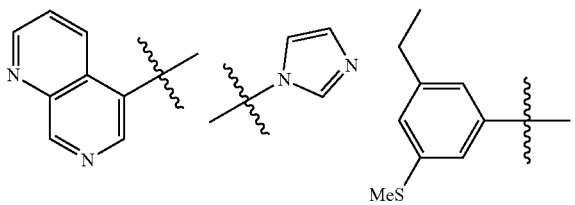

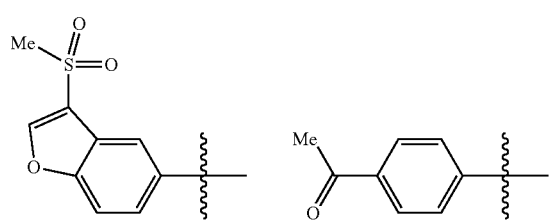

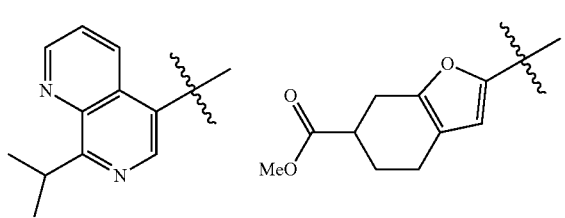

Examples of Substituted or Non-substituted Alkylsulfonyl Arylsulfonyl Radical

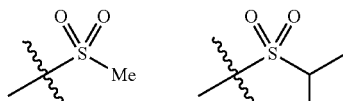

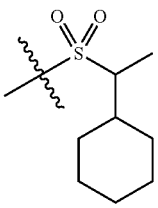

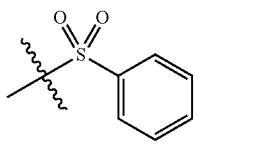

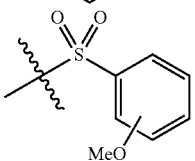

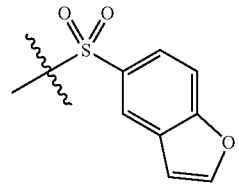

Examples for substituted or non-substituted alkyloxycarbonyl or aryloxycarbonyl, substituted or non-substituted alkylaminocarbonyl or arylaminocarbonyl radicals are provided below.

Examples of Substituted or Non-substituted Alkyloxycarbonyl Radical

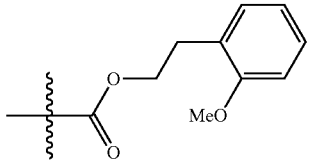

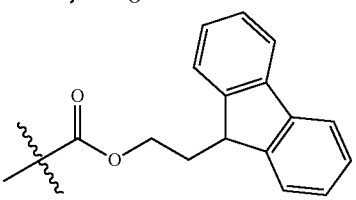

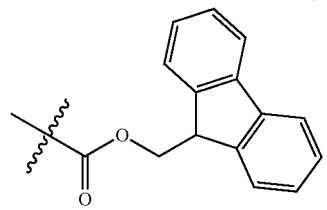

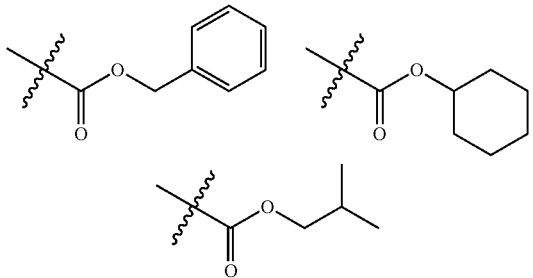

-continued

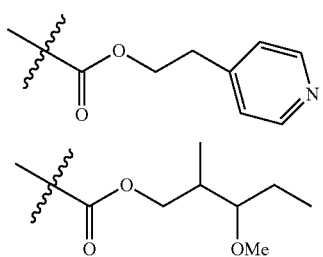

Examples of Substituted or Non-substituted Aryloxycarbonyl Radical

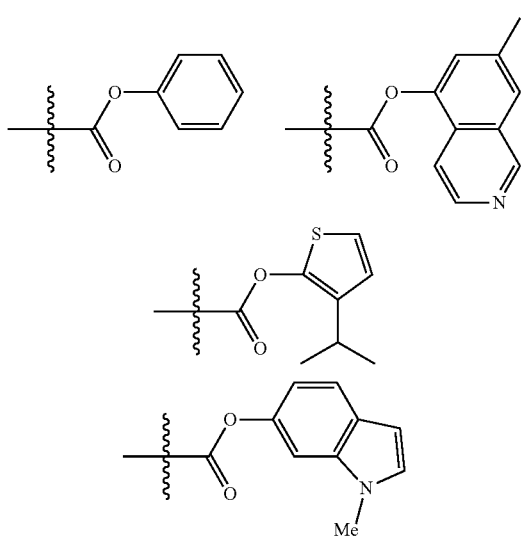

Examples of Substituted or Non-substituted Alkylaminocarbonyl Radical

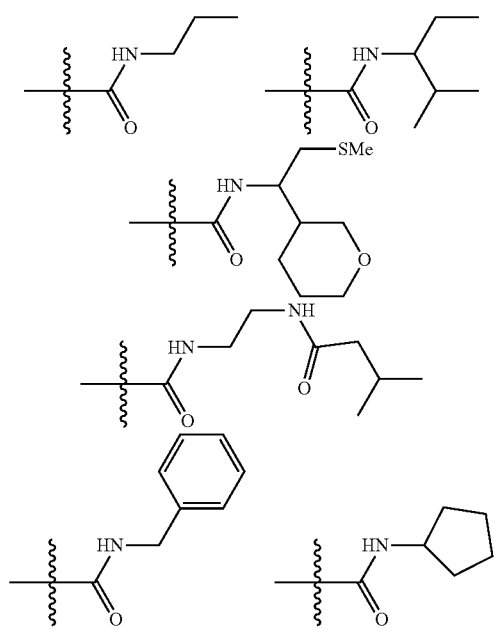

-continued

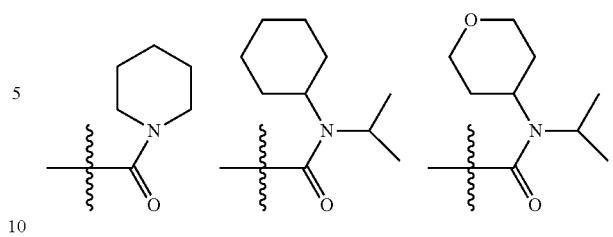

Examples of Substituted or Non-substituted Arylaminocarbonyl Radical

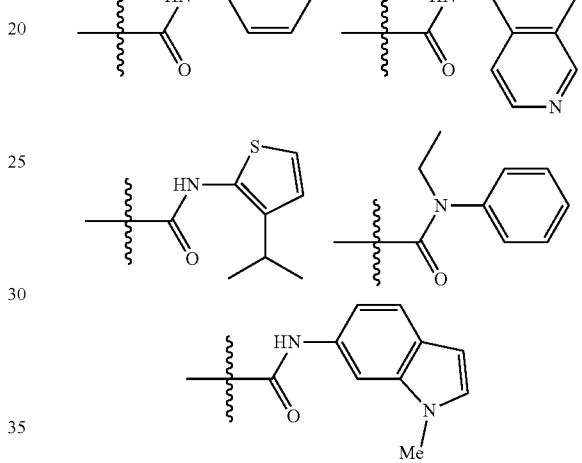

Examples for substituted or non-substituted alkylaminothiocarbonyl, substituted or non-substituted arylaminothiocarbonyl, substituted or non-substituted alkyloxythiocarbonyl, and substituted or non-substituted aryloxythiocarbonyl radicals are provided below.

Examples of Substituted or Non-substituted Alkyloxythiocarbonyl Radical

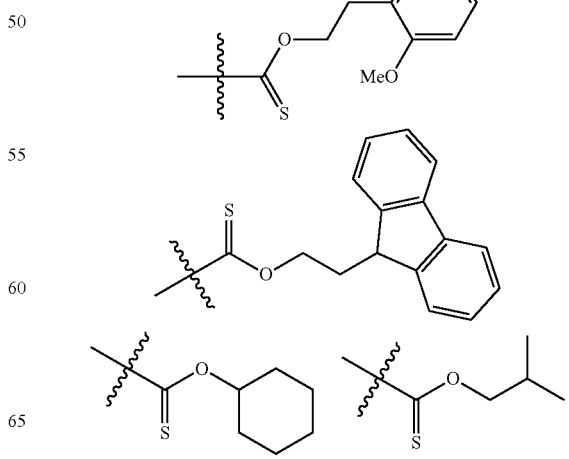

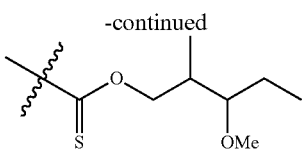

Examples of Substituted or Non-substituted Alkylaminothiocarbonyl Radical

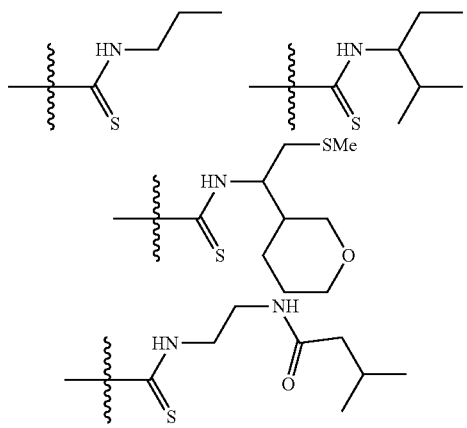

Examples of Substituted or Non-substituted Alkylaminothiocarbonyl Radical

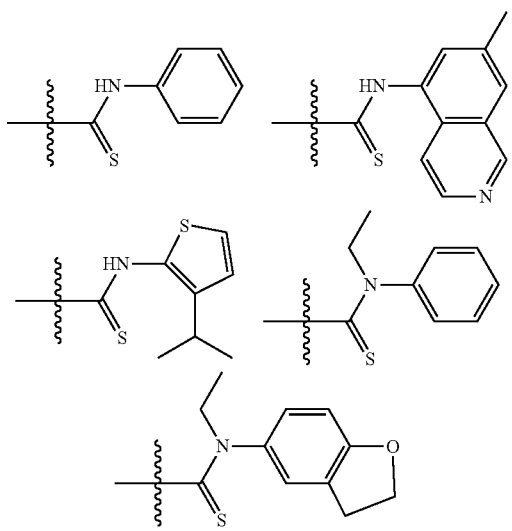

Examples of Substituted or Non-substituted Aryloxythiocarbonyl Radical

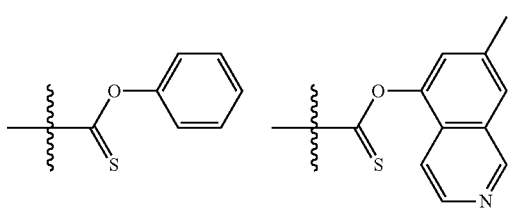

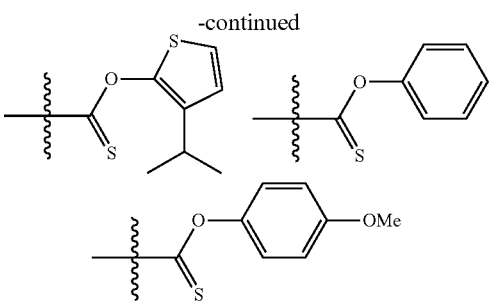

Provision of such exemplary substituents is to illustrate the diversity of substituents allowable for the compound of Formula I, and therefore should not be interpreted to limit the scope of the present invention. A skilled person in the field may easily figure out that the PNA oligonucleotide sequence is the overriding contributor for the sequence specific binding of the said PNA oligonucleotide to the target pre-mRNA sequence over the substituents in the N-terminus or C-terminus.

The PNA compound of Formula I possesses good cell permeability and can be readily delivered into cell if treated as "naked" oligonucleotide as exemplified in the prior art [PCT/KR2009/001256]. Thus the compound of this invention induces the skipping of "exon 2" in the HIF-1α pre-mRNA to yield HIF-1α mRNA splice variant(s) lacking HIF-1α "exon 2" in cells treated with the said compound as "naked" oligonucleotide. Cells treated with the compound of Formula I as "naked" oligonucleotide express a lower level of the full length HIF-1α mRNA and protein than cells without a treatment with the said PNA compound. Likewise, the compound of Formula I inhibits HIF-1α expression in solid tumor tissues upon systemic administration as "naked oligonucleotide". Thus the said compound is useful to treat solid tumors or disorders involving excessive HIF-1α expression.

The compound of Formula I does not require an invasive formulation to increase systemic delivery to target tissue for the intended therapeutic or biological activity. Usually the compound of Formula I is dissolved in PBS (phosphate buffered saline) or saline, and systemically administered to elicit the desired therapeutic (i.e., anti-tumor) or biological activity in target tissues.

The PNA derivative of Formula I may be used as combined or formulated with a pharmaceutically acceptable acid or base including but not limited to sodium hydroxide, potassium hydroxide, hydrochloric acid, methanesulfonic acid, citric acid, trifluoroacetic acid, and so on.

The PNA compound of Formula I or a pharmaceutically acceptable salt thereof can be administered to a subject in combination with a pharmaceutically acceptable adjuvant including but not limited to citric acid, hydrochloric acid, tartaric acid, stearic acid, polyethyleneglycol, polypropyleneglycol, ethanol, isopropanol, sodium bicarbonate, distilled water, preservative(s), and so on.

The compound of the present invention can be systemically administered to a subject at a therapeutically effective dose ranging from 1 fmole/Kg to higher than 1 nmole/Kg, which would vary depending on the dosing schedule, conditions or situations of subject, and so on.

The compound of the present invention can be topically administered to a subject at a therapeutically effective concentration ranging from 1 aM to higher than 1 nM, which would vary depending on the dosing schedule, conditions or situations of subject, and so on.

In certain embodiments, the present invention provides a PNA derivative of Formula I, or a pharmaceutically acceptable salt thereof:

wherein, n is an integer between 10 and 26;

the compound of Formula I possesses at least a 10-mer complementary overlap with the 14-mer RNA sequence of [(5'→3') UAAGUAGGAUAAGU (SEQ ID NO: 2)] in the human HIF-1α pre-mRNA;

the compound of Formula I is fully complementary to the target HIF-1α pre-mRNA sequence, or partially complementary to the target HIF-1α pre-mRNA sequence with one or two mismatches;

$S_1, S_2, \ldots, S_{n-1}, S_n, T_1, T_2, \ldots, T_{n-1}$, and $T_n$ independently represent deuterido, hydrido, substituted or non-substituted alkyl, or substituted or non-substituted aryl radical;

X and Y independently represent hydrido [H], formyl [H—C(=O)—], aminocarbonyl [NH$_2$—C(=O)—], substituted or non-substituted alkyl, substituted or non-substituted aryl, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylsulfonyl, or substituted or non-substituted arylsulfonyl radical;

Z represents hydroxy, substituted or non-substituted alkyloxy, substituted or non-substituted aryloxy, amino [—NH$_2$], substituted or non-substituted alkylamino, substituted or non-substituted arylamino, substituted or non-substituted alkyl, or substituted or non-substituted aryl radical;

$B_1, B_2, \ldots, B_{n-1}$, and $B_n$ are independently selected from natural nucleobases including adenine, thymine, guanine, cytosine and uracil, and unnatural nucleobases; and at least four of $B_1, B_2, \ldots, B_{n-1}$, and $B_n$ are independently selected from unnatural nucleobases with a substituted or non-substituted amino radical covalently linked to the nucleobase moiety.

Preferred is a PNA derivative of Formula I, or a pharmaceutically acceptable salt thereof:

wherein, n is an integer between 10 and 26;

the compound of Formula I possesses at least a 10-mer complementary overlap with the 14-mer RNA sequence of [(5'→3') UAAGUAGGAUAAGU (SEQ ID NO: 2)] in the human HIF-1α pre-mRNA;

the compound of Formula I is fully complementary to the target HIF-1α pre-mRNA sequence, or partially complementary to the target HIF-1α pre-mRNA sequence with one or two mismatches;

$S_1, S_2, \ldots, S_{n-1}, S_n, T_1, T_2, \ldots, T_{n-1}$, and $T_n$ independently represent deuterido, hydrido, substituted or non-substituted alkyl, or substituted or non-substituted aryl radical;

X and Y independently represent hydrido, formyl, aminocarbonyl, substituted or non-substituted alkyl, substituted or non-substituted aryl, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylsulfonyl, or substituted or non-substituted arylsulfonyl radical;

Z represents hydroxy, substituted or non-substituted alkyloxy, substituted or non-substituted aryloxy, amino [—NH$_2$], substituted or non-substituted alkylamino, substituted or non-substituted arylamino, substituted or non-substituted alkyl, or substituted or non-substituted aryl radical;

$B_1, B_2, \ldots, B_{n-1}$, and $B_n$ are independently selected from natural nucleobases including adenine, thymine, guanine, cytosine and uracil, and unnatural nucleobases; and, at least three of $B_1, B_2, \ldots, B_{n-1}$, and $B_n$ are independently selected from unnatural nucleobases represented by Formula II, Formula III, or Formula IV:

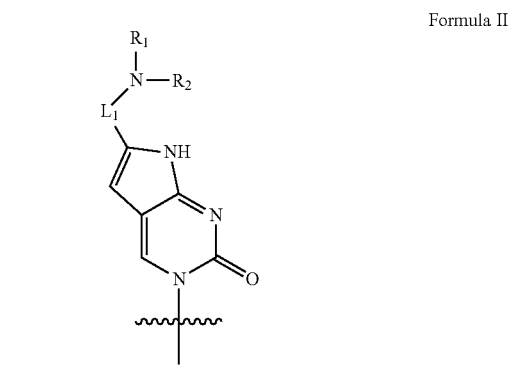

Formula II

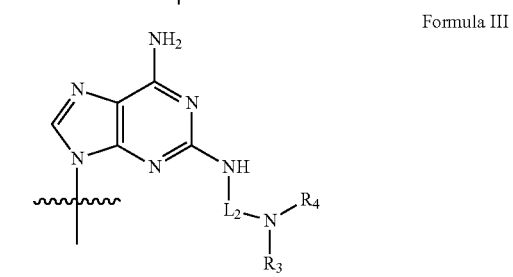

Formula III

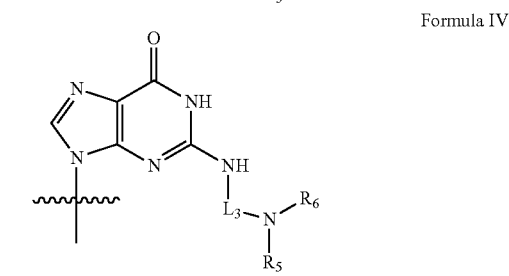

Formula IV wherein, $R_1, R_2, R_3, R_4, R_5$ and $R_6$ are independently selected from substituted or non-substituted alkyl, hydrido, hydroxy, and substituted or non-substituted alkyloxy radical; and $L_1, L_2$ and $L_3$ are a covalent linker represented by Formula V connecting a basic amino group to the moiety responsible for nucleobase pairing properties:

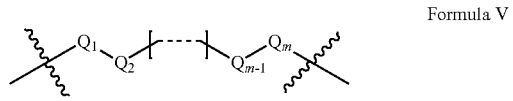

Formula V wherein, $Q_1$ and $Q_m$ are substituted or non-substituted methylene (—CH$_2$—) radical, and $Q_m$ is directly linked to the basic amino group;

$Q_2, Q_3, \ldots$, and $Q_{m-1}$ are independently selected from substituted or non-substituted methylene, oxygen (—O—), sulfur (—S—), and substituted or non-substituted amino radical [—N(H)—, or —N(substituent)-]; and, m is an integer between 1 and 16.

Of interest is a PNA oligomer of Formula I, or a pharmaceutically acceptable salt thereof:
wherein,
n is an integer between 11 and 23;
the compound of Formula I possesses at least a 10-mer complementary overlap with the 14-mer RNA sequence of [(5'→3') UAAGUAGGAUAAGU (SEQ ID NO: 2)] in the human HIF-1α pre-mRNA;
the compound of Formula I is fully complementary to the target HIF-1α pre-mRNA sequence, or partially complementary to the target HIF-1α pre-mRNA sequence with one or two mismatches;
$S_1, S_2, \ldots, S_{n-1}, S_n, T_1, T_2, \ldots, T_{n-1}$, and $T_n$ independently represent hydrido radical;
X and Y independently represent hydrido, substituted or non-substituted alkyl, substituted or non-substituted aryl, substituted or non-substituted alkylacyl, substituted or non-substituted arylacyl, substituted or non-substituted alkyloxycarbonyl, substituted or non-substituted alkylaminocarbonyl, substituted or non-substituted arylaminocarbonyl, substituted or non-substituted alkylsulfonyl, or substituted or non-substituted arylsulfonyl radical;
Z represents amino, or substituted or non-substituted alkylamino radical;
$B_1, B_2, \ldots, B_{n-1}$, and $B_n$ are independently selected from natural nucleobases including adenine, thymine, guanine, cytosine and uracil, and unnatural nucleobases; and,
at least four of $B_1, B_2, \ldots, B_{n-1}$, and $B_n$ are independently selected from unnatural nucleobases represented by Formula II, Formula III, or Formula IV;
$R_1, R_2, R_3, R_4, R_5$ and $R_6$ are independently selected from substituted or non-substituted alkyl, and hydrido radical;
$Q_1$ and $Q_m$ are substituted or non-substituted methylene radical, and $Q_m$ is directly linked to the basic amino group;
$Q_2, Q_3, \ldots$, and $Q_{m-1}$ are independently selected from substituted or non-substituted methylene, oxygen (—O—), and amino radical [—N(H)—]; and
m is an integer between 1 and 11.

Of particular interest is a PNA derivative of Formula I, or a pharmaceutically acceptable salt thereof:
wherein,
n is an integer between 11 and 21;
the compound of Formula I possesses at least a 10-mer complementary overlap with the 14-mer RNA sequence of [(5'→3') UAAGUAGGAUAAGU (SEQ ID NO: 2)] in the human HIF-1α pre-mRNA;
the compound of Formula I is fully complementary to the target HIF-1α pre-mRNA sequence;
$S_1, S_2, \ldots, S_{n-1}, S_n, T_1, T_2, \ldots, T_{n-1}$, and $T_n$ independently represent hydrido radical;
X and Y independently represent hydrido, substituted or non-substituted alkyl, substituted or non-substituted aryl, substituted or non-substituted alkylacyl, substituted or non-substituted arylacyl, or substituted or non-substituted alkyloxycarbonyl radical;
Z represents amino, or substituted or non-substituted alkylamino radical;
$B_1, B_2, \ldots, B_{n-1}$, and $B_n$ are independently selected from natural nucleobases including adenine, thymine, guanine and cytosine, and unnatural nucleobases; and,
at least four of $B_1, B_2, \ldots, B_{n-1}$, and $B_n$ are independently selected from unnatural nucleobases represented by Formula II, Formula III, or Formula IV;
$R_1, R_2, R_3, R_4, R_5$ and $R_6$ are independently selected from substituted or non-substituted alkyl, and hydrido radical;
$Q_1$ and $Q_m$ are methylene radical, and $Q_m$ is directly linked to the basic amino group;
$Q_2, Q_3, \ldots$, and $Q_{m-1}$ are independently selected from substituted or non-substituted methylene, and oxygen radical; and
m is an integer between 1 and 9.

Of high interest is a PNA oligomer of Formula I, or a pharmaceutically acceptable salt thereof:
wherein,
n is an integer between 12 and 19;
the compound of Formula I possesses at least a 10-mer complementary overlap with the 14-mer RNA sequence of [(5'→3') UAAGUAGGAUAAGU (SEQ ID NO: 2)] in the human HIF-1α pre-mRNA;
the compound of Formula I is fully complementary to the target HIF-1α pre-mRNA sequence;
$S_1, S_2, \ldots, S_{n-1}, S_n, T_1, T_2, \ldots, T_{n-1}$, and $T_n$ independently represent hydrido radical;
X and Y independently represent hydrido, substituted or non-substituted alkylacyl, substituted or non-substituted arylacyl, or substituted or non-substituted alkyloxycarbonyl radical;
Z represents amino, or substituted or non-substituted alkylamino radical;
$B_1, B_2, \ldots, B_{n-1}$, and $B_n$ are independently selected from natural nucleobases including adenine, thymine, guanine and cytosine, and unnatural nucleobases; and,
at least four of $B_1, B_2, \ldots, B_{n-1}$, and $B_n$ are independently selected from unnatural nucleobases represented by Formula II, Formula III, or Formula IV;
$R_1, R_2, R_3, R_4, R_5$ and $R_6$ are independently selected from substituted or non-substituted alkyl, and hydrido radical;
$Q_1$ and $Q_m$ are methylene radical, and $Q_m$ is directly linked to the basic amino group;
$Q_2, Q_3, \ldots$, and $Q_{m-1}$ are independently selected from methylene, and oxygen radical; and
m is an integer between 1 and 9.

Of higher interest is a PNA derivative of Formula I, or a pharmaceutically acceptable salt thereof:
wherein,
n is an integer between 12 and 19;
the compound of Formula I possesses at least a 11-mer complementary overlap with the 14-mer RNA sequence of [(5'→3') UAAGUAGGAUAAGU (SEQ ID NO: 2)] in the human HIF-1α pre-mRNA;
the compound of Formula I is fully complementary to the target HIF-1α pre-mRNA sequence;
$S_1, S_2, \ldots, S_{n-1}, S_n, T_1, T_2, \ldots, T_{n-1}$, and $T_n$ independently represent hydrido radical;
X and Y independently represent hydrido, substituted or non-substituted alkylacyl, substituted or non-substituted arylacyl, or substituted or non-substituted alkyloxycarbonyl radical;
Z represents amino, or substituted or non-substituted alkylamino radical;
$B_1, B_2, \ldots, B_{n-1}$, and $B_n$ are independently selected from natural nucleobases including adenine, thymine, guanine and cytosine, and unnatural nucleobases; and
at least four of $B_1, B_2, \ldots, B_{n-1}$, and $B_n$ are independently selected from unnatural nucleobases represented by Formula II, Formula III, or Formula IV;
$R_1, R_2, R_3, R_4, R_5$ and $R_6$ are hydrido radical;
$Q_1$ and $Q_m$ are methylene radical, and $Q_m$ is directly linked to the basic amino group;
$Q_2, Q_3, \ldots$, and $Q_{m-1}$ are independently selected from methylene, and oxygen radical; and,
m is an integer between 1 and 8.

Of highest interest is a PNA derivative of Formula I, or a pharmaceutically acceptable salt thereof:
wherein,
n is an integer between 12 and 19;
the compound of Formula I possesses at least a 12-mer complementary overlap with the 14-mer RNA sequence of [(5'→3') UAAGUAGGAUAAGU (SEQ ID NO: 2)] in the human HIF-1α pre-mRNA;
the compound of Formula I is fully complementary to the target HIF-1α pre-mRNA sequence;
$S_1, S_2, \ldots, S_{n-1}, S_n, T_1, T_2, \ldots, T_{n-1}$, and $T_n$ independently represent hydrido radical;
X is hydrido radical;
Y represents substituted or non-substituted alkylacyl, substituted or non-substituted arylacyl, or substituted or non-substituted alkyloxycarbonyl radical;
Z represents amino, or substituted or non-substituted alkylamino radical;
$B_1, B_2, \ldots, B_{n-1}$, and $B_n$ are independently selected from natural nucleobases including adenine, thymine, guanine and cytosine, and unnatural nucleobases;
at least four of $B_1, B_2, \ldots, B_{n-1}$, and $B_n$ are independently selected from unnatural nucleobases represented by Formula II, Formula III, or Formula IV;
$R_1, R_2, R_3, R_4, R_5$ and $R_6$ are hydrido radical;
$L_1$ represents —$(CH_2)_2$—O—$(CH_2)_2$—, —$CH_2$—O—$(CH_2)_2$—, —$CH_2$—O—$(CH_2)_3$—, —$CH_2$—O—$(CH_2)_4$—, —$CH_2$—O—$(CH_2)_5$—, —$CH_2$—O—$(CH_2)_6$—, or —$CH_2$—O—$(CH_2)_7$— with the right end is directly linked to the basic amino group; and,
$L_2$ and $L_3$ are independently selected from —$(CH_2)_2$—O—$(CH_2)_2$—, —$(CH_2)_3$—O—$(CH_2)_2$—, —$(CH_2)_2$—O—$(CH_2)_3$—, —$(CH_2)_2$—, —$(CH_2)_3$—, —$(CH_2)_4$—, —$(CH_2)_5$—, —$(CH_2)_6$—, —$(CH_2)_7$—, and —$(CH_2)_8$— with the right end is directly linked to the basic amino group.

Of specific interest is a PNA derivative of Formula I which is selected from the group of compounds provided below, or a pharmaceutically acceptable salt thereof:

(N→C) Fethoc-CA(5)G-AA(5)C-TTA(5)-TCC(102)-TA(5)-NH₂;

(N→C) Fmoc-CA(5)G-AA(5)C-TTA(5)-TCC(102)-TA(5)-NH₂;

(N→C) H-CA(5)G-AA(5)C-TTA(5)-T CC(103)-TA(5)-NH₂;

(N→C) Ac-CA(5)G-AA(5)C-TTA(5)-TCC(102)-TA(5)-NH₂;

(N→C) Piv-CA(5)G-AA(5)C-TTA(5)-TCC(102)-TA(5)-NH₂;

(N→C) Benzoyl-CA(5)G(203)-AA(5)C-TTA(4)-TCC(102)-TA(5)-NH₂;

(N→C) n-Propyl-CA(5)G-AA(5)C-TTA(5)-TCC(202)-TA(5)-NH₂;

(N→C) Benzyl-CA(5)G-AA(5)C-TTA(5)-TCC(102)-TA(5)-NH₂;

(N→C) p-Toluenesulfonyl-CA(5)G-AA(5)C-TTA(202)-TCC(102)-TA(5)-NH₂;

(N→C) N-(2-Phenylethyl)aminolcarbonyl-CA(5)G(3)-AA(5)C-TTA(3)-TCC(102)-TA(5)-NH₂;

(N→C) Fethoc-Lys-Leu-CA(5)G(202)-AA(5)C-TTA(8)-TCC(102)-TA(5)-Lys-NH₂;

(N→C) N-Ph-N-Me-CA(5)G-AA(5)C-TTA(5)-TCC(102)-TA(5)-Lys-NH₂;

(N→C) Piv-HEX-CA(5)G-AA(5)C-TTA(5)-TCC(102)-TA(5)-Lys-NH₂;

(N→C) FAM-HEX-CA(5)G-AA(5)C-TTA(5)-TCC(102)-TA(5)-Lys-NH₂;

(N→C) Fethoc-GA(5)A-C(102)TT-A(5)TC-CTA(5)-C(102)T-NH₂;

(N→C) Fethoc-G(5)AA(5)-CTT-A(5)TC-CTA(5)-C(102)T-NH₂;

(N→C) Fethoc-GA(5)A-C(102)TT-A(5)TC-CTA(5)-CT-NH₂;

(N→C) Fethoc-G(5)AA(6)-CTT-A(6)TC-CTA(6)-C(102)T-NH₂;

(N→C) Fethoc-GA(202)A-C(105)TT-A(3)TC-CTA(5)-C(103)T-NH₂;

(N→C) Benzoyl-Gly-GA(5)A-C(102)TT-A(5)TC-CTA(5)-C(102)T-NH₂;

(N→C) Fethoc-Arg-GA(5)A-C(102)TT-A(5)TC-CTA(5)-C(102)T-Gly-NH₂;

(N→C) Fethoc-Val-GA(5)A-CTT-A(6)TC-CTA(5)-C(202)T-Gly-Lys-NH₂;

(N→C) Fethoc-A(6)GA-A(6)CT-TA(6)T-CC(102)T-A(6)CT-TA(6)-NH₂;

(N→C) Fethoc-A(5)GA-AC(102)T-TG(6)T-CC(102)T-A(6)CT-TA(6)-NH₂;

(N→C) Fethoc-A(6)GA-A(6)CT-TA(6)T-CC(102)T-A(6)CT-CA-NH₂;

(N→C) Fethoc-A(6)GA-A(6)CT-TA(6)T-CC(102)T-A(6)CT-AT-NH₂;

(N→C) Piv-Lys-AA(6)C-TTA(6)-TCC(102)-TA(6)C-TTA(5)-Val-NH₂;

(N→C) Fethoc-A(6)GA-A(6)CT-CA(6)T-CC(102)T-A(6)CT-TA(6)-NH₂;

(N→C) Fethoc-C(105)TT-A(6)TC-CTA(6)-C(102)TT-AA(6)C-NH₂;

(N→C) Fethoc-CTC(102)-A(6)TC-CTA(6)-C(102)TT-AA(6)C-NH₂;

(N→C) Fmoc-Val-CTC(102)-A(5)TC-CTA(6)-C(103)TT-AA(202)C-NH₂;

(N→C) Piv-A(6)TC-CTA(6)-C(102)TT-A(5)AC-NH₂;

(N→C) Fethoc-TTC(105)-AG(5)A-A(4)CT-TA(5)T-CC(202)T-A(6)CT-TA(6)A-C-NH₂;

(N→C) Fethoc-G-TTC(105)-AG(5)A-A(4)CT-TA(5)T-CC(102)T-AC(105)T-TA(6)A-C-NH₂;
and (N→C) Fethoc-TTC(105)-AG(5)A-A(4)CT-TA(5)T-CCT-AC(105)T-TAA-CA(202)A-NH₂:

wherein,

A, G, T, and C are PNA monomers with a natural nucleobase of adenine, guanine, thymine, and cytosine, respectively;

C(pOq), A(p), A(pOq), G(p), and G(pOq) are PNA monomers with an unnatural nucleobase represented by Formula VI, Formula VII, Formula VIII, Formula IX, and Formula X, respectively;

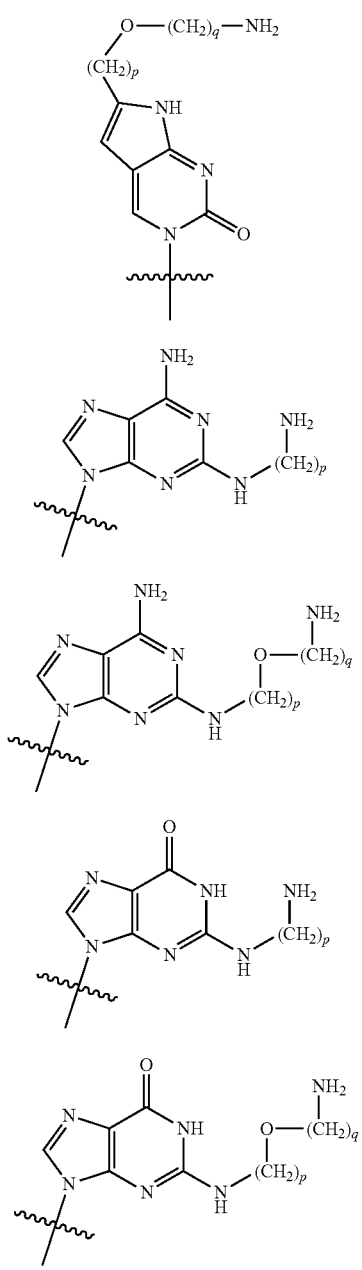

Formula VI

Formula VII

Formula VIII

Formula IX

Formula X wherein, p and q are integers; and, the abbreviations for the N- and C-terminus substituents are as specifically described as follows: "Fmoc-" is the abbreviation for "[(9-fluorenyl)methyloxy]carbonyl-"; "Fethoc-" for "[2-(9-fluorenyl)ethyl-1-oxy]carbonyl"; "Ac-" for "acetyl-"; "Benzoyl-" for "benzenecarbonyl-"; "Piv-" for "pivaloyl-"; "n-Propyl-" for "1-(n-propyl)-"; "H-" for "hydrido-" group; "p-Toluenesulfonyl-" for "(4-methyl-benzene)-1-sulfonyl-"; "-Lys-" for amino acid residue "lysine"; "—Val-" for amino acid residue "valine"; "-Leu-" for amino acid residue "leucine"; "-Arg-" for amino acid residue "arginine"; "-Gly-" for amino acid residue "glycine"; "[N-(2-Phenylethyl)amino]carbonyl-" for "[N-(2-phenylethyl)amino]carbonyl-"; "Benzyl-" for "1-(phenyl)methyl-"; "Phenyl-" for "phenyl-"; "Me-" for "methyl-"; "—HEX-" for "6-amino-1-hexanoyl-", "FAM-" for "5, or 6-fluorescein-carbonyl- (isomeric mixture)", and "—$NH_2$" for non-substituted "-amino" group.

In certain embodiments, the present invention provides a PNA derivative of Formula I, or a pharmaceutically acceptable salt thereof:

wherein, the compound of Formula I possesses at least a 10-mer complementary overlap with a 20-mer RNA sequence [(5'→3') UGUUAAGUAGGAUAAGUUCU (SEQ ID NO: 1)], a part of the human HIF-1α pre-mRNA;

n is an integer between 10 and 26;

$S_1, S_2, \ldots, S_{n-1}, S_n, T_1, T_2, \ldots, T_{n-1}$, and $T_n$ independently represent hydrido, substituted or non-substituted alkyl, or substituted or non-substituted aryl radical;

X and Y independently represent hydrido, substituted or non-substituted alkyl, substituted or non-substituted acyl, substituted or non-substituted sulfonyl, or substituted or non-substituted aryl radical;

Z represents hydrido, hydroxy, substituted or non-substituted alkyloxy, substituted or non-substituted aryloxy, substituted or non-substituted amino radical;

$B_1, B_2, \ldots, B_{n-1}$, and $B_n$ are independently selected from natural nucleobases including adenine, thymine, guanine, cytosine and uracil, and unnatural nucleobases; and, at least three of $B_1, B_2, \ldots, B_{n-1}$, and $B_n$ are independently selected from unnatural nucleobases with a substituted or non-substituted amino radical covalently linked to the moiety responsible for its due nucleobase pairing properties.

In certain embodiments, the present invention provides a PNA derivative of Formula I, or a pharmaceutically acceptable salt thereof:

wherein, the compound of Formula I possesses at least a 10-mer complementary overlap with a 20-mer RNA sequence [(5'→3') UGUUAAGUAGGAUAAGUUCU (SEQ ID NO: 1)], a part of the human HIF-1α pre-mRNA;

n is an integer between 10 and 26;

$S_1, S_2, \ldots, S_{n-1}, S_n, T_1, T_2, \ldots, T_{n-1}$, and $T_n$ independently represent hydrido radical;

X and Y independently represent hydrido, substituted or non-substituted alkyl, substituted or non-substituted acyl, substituted or non-substituted sulfonyl, or substituted or non-substituted aryl radical;

Z represents hydrido, hydroxy, substituted or non-substituted alkyloxy, substituted or non-substituted aryloxy, substituted or non-substituted amino radical;

$B_1, B_2, \ldots, B_{n-1}$, and $B_n$ are independently selected from natural nucleobases including adenine, thymine, guanine, cytosine and uracil, and unnatural nucleobases;

at least three of $B_1, B_2, \ldots, B_{n-1}$, and $B_n$ are independently selected from unnatural nucleobases represented by Formula II, Formula III, or Formula IV:

wherein, $R_1, R_2, R_3, R_4, R_5$ and $R_6$ are independently selected from substituted or non-substituted alkyl, hydrido, hydroxy, and substituted or non-substituted alkyloxy radical; and, $L_1, L_2$ and $L_3$ are a covalent linker represented by Formula V connecting a basic amino group to the moiety responsible for nucleobase pairing properties:

wherein, $Q_1$ and $Q_m$ are substituted or non-substituted methylene (—$CH_2$—) radical, and $Q_m$ is directly linked to the basic amino group;

$Q_2, Q_3, \ldots$, and $Q_{m-1}$ are independently selected from substituted or non-substituted methylene, oxygen (—O—), sulfur (—S—), and substituted or non-substituted amino radical [—N(H)—, or —N(substituent)-]; and, m is an integer between 1 and 16.

In certain embodiments, the present invention provides a PNA derivative of Formula I, or a pharmaceutically acceptable salt thereof:

wherein, the compound of Formula I possesses at least a 10-mer complementary overlap with a 20-mer RNA sequence [(5'→3') UGUUAAGUAGGAUAAGUUCU (SEQ ID NO: 1)], a part of the human HIF-1α pre-mRNA;

n is an integer between 11 and 21;

$S_1, S_2, \ldots, S_{n-1}, S_n, T_1, T_2, \ldots, T_{n-1}$, and $T_n$ are hydrido radical;

X and Y are independently selected from hydrido, substituted or non-substituted alkyl, and substituted or non-substituted acyl radical;

Z represents hydroxy, or substituted or non-substituted amino radical;

$B_1, B_2, \ldots, B_{n-1}$, and $B_n$ are independently selected from natural nucleobases including adenine, thymine, guanine, cytosine and uracil, and unnatural nucleobases;

at least four of $B_1, B_2, \ldots, B_{n-1}$, and B. are independently selected from unnatural nucleobases represented by Formula II, Formula III, or Formula IV;

$R_1, R_2, R_3, R_4, R_5$ and $R_6$ are independently selected from substituted or non-substituted alkyl, and hydrido radical;

$Q_1$ and $Q_m$ are substituted or non-substituted methylene radical, and $Q_m$ is directly linked to the basic amino group;

$Q_2, Q_3, \ldots,$ and $Q_{m-1}$ are independently selected from substituted or non-substituted methylene, oxygen, and amino radical; and, m is an integer between 1 and 11.

In certain embodiments, the present invention provides a PNA derivative of Formula I, or a pharmaceutically acceptable salt thereof:

wherein, the compound of Formula I possesses at least a 10-mer complementary overlap with a 20-mer RNA sequence [(5'→3') UGUUAAGUAGGAUAAGUUCU (SEQ ID NO: 1)], a part of the human HIF-1α pre-mRNA;

n is an integer between 11 and 19;

$S_1, S_2, \ldots, S_{n-1}, S_n, T_1, T_2, \ldots, T_{n-1}$, and $T_n$ are hydrido radical;

X and Y are independently selected from hydrido, and substituted or non-substituted acyl radical;

Z represents substituted or non-substituted amino radical; and, $B_1, B_2, \ldots, B_{n-1}$, and $B_n$ are independently selected from natural nucleobases including adenine, thymine, guanine, cytosine and uracil, and unnatural nucleobases;

at least four of $B_1, B_2, \ldots, B_{n-1}$, and $B_n$ are independently selected from unnatural nucleobases represented by Formula II, Formula III, or Formula IV;

$R_1, R_2, R_3, R_4, R_5$ and $R_6$ are independently selected from substituted or non-substituted alkyl, and hydrido radical;

$Q_1$ and $Q_m$ are methylene radical, and $Q_m$ is directly linked to the basic amino group;

$Q_2, Q_3, \ldots,$ and $Q_{m-1}$ are independently selected from methylene, oxygen, and amino radical; and, m is an integer between 1 and 9.

In certain embodiments, the present invention provides a PNA derivative of Formula I, or a pharmaceutically acceptable salt thereof:

wherein, the compound of Formula I possesses at least a 10-mer complementary overlap with a 20-mer RNA sequence [(5'→3') UGUUAAGUAGGAUAAGUUCU (SEQ ID NO: 1)], a part of the human HIF-1α pre-mRNA;

n is an integer between 11 and 19;

$S_1, S_2, \ldots, S_{n-1}, S_n, T_1, T_2, \ldots, T_{n-1}$, and $T_n$ are hydrido radical;

X and Y are independently selected from hydrido, and substituted or non-substituted acyl radical;

Z represents substituted or non-substituted amino radical;

$B_1, B_2, \ldots, B_{n-1}$, and $B_n$ are independently selected from natural nucleobases including adenine, thymine, guanine, cytosine and uracil, and unnatural nucleobases;

at least four of $B_1, B_2, \ldots, B_{n-1}$, and $B_n$ are independently selected from unnatural nucleobases represented by Formula II, Formula III, or Formula IV;

$R_1, R_3,$ and $R_5$ are hydrido radical, and $R_2, R_4,$ and $R_6$ independently represent hydrido, or substituted or non-substituted alkyl radical;

$Q_1$ and $Q_m$ are methylene radical, and $Q_m$ is directly linked to the basic amino group;

$Q_2, Q_3, \ldots,$ and $Q_{m-1}$ are independently selected from methylene, oxygen radical; and, m is an integer between 1 and 9.

In certain embodiments, the present invention provides a PNA derivative of Formula I, or a pharmaceutically acceptable salt thereof:

wherein, the compound of Formula I possesses at least a 10-mer complementary overlap with a 20-mer RNA sequence [(5'→3') UGUUAAGUAGGAUAAGUUCU (SEQ ID NO: 1)], a part of the human HIF-1α pre-mRNA;

n is an integer between 11 and 19;

$S_1, S_2, \ldots, S_{n-1}, S_n, T_1, T_2, \ldots, T_{n-1}$, and $T_n$ are hydrido radical;

X and Y are independently selected from hydrido, and substituted or non-substituted acyl radical;

Z represents substituted or non-substituted amino radical;

$B_1, B_2, \ldots, B_{n-1}$, and $B_n$ are independently selected from adenine, thymine, guanine, cytosine, and unnatural nucleobases;

at least four of $B_1, B_2, \ldots, B_{n-1}$, and $B_n$ are independently selected from unnatural nucleobases represented by Formula II, Formula III, or Formula IV;

$R_1, R_2, R_3, R_4, R_5,$ and $R_6$ are hydrido radical;

$Q_1$ and $Q_m$ are methylene radical, and $Q_m$ is directly linked to the basic amino group;

$Q_2, Q_3, \ldots,$ and $Q_{m-1}$ are independently selected from methylene, and oxygen radical; and, m is an integer between 1 and 8.

In certain embodiments, the present invention provides a PNA derivative of Formula I, or a pharmaceutically acceptable salt thereof:

wherein, the compound of Formula I possesses at least a 10-mer complementary overlap with a 20-mer RNA sequence [(5'→3') UGUUAAGUAGGAUAAGUUCU (SEQ ID NO: 1)], a part of the human HIF-1α pre-mRNA;

n is an integer between 11 and 17;

$S_1, S_2, \ldots, S_{n-1}, S_n, T_1, T_2, \ldots, T_{n-1}$, and $T_n$ are hydrido radical;

X is hydrido radical;

Y represents substituted or non-substituted acyl radical;

Z represents substituted or non-substituted amino radical;

$B_1, B_2, \ldots, B_{n-1}$, and $B_n$ are independently selected from adenine, thymine, guanine, cytosine, and unnatural nucleobases;

at least four of $B_1, B_2, \ldots, B_{n-1}$, and $B_n$ are independently selected from unnatural nucleobases represented by Formula II, Formula III, or Formula IV;

$R_1, R_2, R_3, R_4, R_5$, and $R_6$ are hydrido radical;

$L_1$ represents —(CH$_2$)$_2$—O—(CH$_2$)$_2$—, —CH$_2$—O—(CH$_2$)$_2$—, or —CH$_2$—O—(CH$_2$)$_3$— with the right end is directly linked to the basic amino group; and, $L_2$ and $L_3$ are independently selected from —(CH$_2$)$_2$—O—(CH$_2$)$_2$—, —(CH$_2$)$_3$—O—(CH$_2$)$_2$—, —(CH$_2$)$_2$—O—(CH$_2$)$_3$—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, and —(CH$_2$)$_8$— with the right end is directly linked to the basic amino group.

In certain embodiments, the present invention provides a PNA derivative of Formula I which is selected from the group of compounds provided below, or a pharmaceutically acceptable salt thereof:

(N→C) Fethoc-CTT-A(6)TC(105)-CTA(6)-C(102)TT-A(5)AC-NH$_2$;

(N→C) Fethoc-C(105)TT-A(6)TC-CTA(6)-C(102)TT-A(5)AC(105)-A-NH$_2$;

(N→C) Fethoc-CA(5)T-A(6)TC-CTA(6)-C(102)TT-A(5)AC(105)-A-NH$_2$;

(N→C) Fethoc-CG(6)T-A(6)TC-CTA(6)-C(102)TT-A(5)AC(105)-A-NH$_2$;

(N→C) Fethoc-AC(102)T-TA(5)T-CC(102)T-A(6)C(102)T-TA(5)A-C-NH$_2$;

(N→C) Fethoc-CTT-A(6)TC-CTA(6)-C(102)TT-A(5)AC-NH$_2$;

(N→C) Piv-AC(102)T-TA(5)T-CC(102)T-A(6)C(102)T-TA(5)A-C-NH$_2$;

(N→C) Benzoyl-AC(102)T-TA(5)T-CC(102)T-A(6)C(102)T-TA(5)A-C-NH$_2$;

(N→C) Fethoc-Lys-AC(102)T-TA(5)T-CC(102)T-A(6)C(102)T-TA(5)A-C-NH$_2$;

(N→C) Fethoc-CTC(102)-A(6)TC-CTA(6)-C(102)TT-AA(6)C-NH$_2$;

(N→C) Fmoc-Val-CTC(102)-A(5)TC-CTA(6)-C(103)TT-AA(202)C-NH$_2$;

(N→C) Fethoc-A(6)GA-A(6)CT-TA(6)T-CC(102)T-A(6)CT-TA(6)-NH$_2$;

(N→C) Fethoc-AG(5)A-A(202)CT-TA(5)T-CC(102)T-A(6)CT-TA-NH$_2$;

(N→C) Piv-AG(5)A-A(202)CT-TA(5)T-CC(102)T-A(6)CT-TA-NH$_2$;

(N→C) Ac-AG(5)A-A(203)CT-TA(5)T-CC(102)T-A(6)CT-TA- (N→C) Fethoc-A(5)GA(5)-AC(103)T-TA(5)T-CC(102)T-A(6)CT-TA(4)-NH$_2$;

(N→C) Fethoc-GA(5)A-C(102)TT-A(5)TC-CTA(5)-C(102)T-NH$_2$;

(N→C) Fethoc-G(5)AA(5)-C(102)TT-A(5)TC-CTA(5)-C(102)T-NH$_2$;

(N→C) Fethoc-GA(5)A-C(102)TT-A(5)TC-CTA(5)-C(102)T-Lys-NH$_2$;

(N→C) Benzoyl-GA(5)A-C(102)TT-A(5)TC-CTA(5)-C(102)T-NH$_2$;

(N→C) Ac-HEX-GA(5)A-C(102)TT-A(5)TC-CTA(5)-C(102)T-NH$_2$;

(N→C) Fmoc-Gly-GA(5)A-C(102)TT-A(5)TC-CTA(5)-C(102)T-NH$_2$;

(N→C) Me-GA(5)A-C(102)TT-A(5)TC-CTA(5)-C(102)T-NH$_2$;

(N→C) Benzyl-GA(5)A-C(102)TT-A(5)TC-CTA(5)-C(102)T-NH$_2$;

(N→C) Fethoc-G(5)AA(5)-CTT-A(5)TC-CTA(5)-C(102)T-NH$_2$;

(N→C) Fethoc-GA(5)A-C(102)TT-A(5)TC-CTA(5)-CT-NH$_2$;

(N→C) Fethoc-G(5)AA(6)-CTT-A(6)TC-CTA(6)-C(102)T-NH$_2$;

and (N→C) Fethoc-CA(5)G-AA(5)C-TTA(5)-TCC(102)-TA(5)-NH$_2$;

wherein,

A, G, T, and C are PNA monomers with a natural nucleobase of adenine, guanine, thymine, and cytosine, respectively;

C(pOq), A(p), A(pOq), G(p), and G(pOq) are PNA monomers with an unnatural nucleobase represented by Formula VI, Formula VII, Formula VIII, Formula IX, and Formula X, respectively;

wherein, p and q are integers; and the abbreviations for the N- and C-terminus substituents are as specifically described as follows: "Fmoc-" is the abbreviation for "[(9-fluorenyl)methyloxy]carbonyl-"; "Fethoc-" for "[2-(9-fluorenyl)ethyl-1-oxy]carbonyl"; "Ac-" for "acetyl-"; "Benzoyl-" for "benzenecabonyl-"; "Piv-" for "pivaloyl-"; "n-Propyl-" for "1-(n-propyl)-"; "-Lys-" for amino acid residue "lysine"; "-Val-" for amino acid residue "valine"; "-Leu-" for amino acid residue "leucine"; "-Arg-" for amino acid residue "arginine"; "-Gly-" for amino acid residue "glycine"; "Benzyl-" for "1-(phenyl)methyl-"; "Phenyl-" for "phenyl-"; "Me-" for "methyl-".

Chemical structures for the PNA monomers abbreviated as A, G, T, C, C(pOq), A(p), A(pOq), G(p), and G(pOq) are collectively provided below. As discussed in the prior art [PCT/KR2009/001256], C(pOq) is regarded as a modified PNA monomer corresponding to "cytosine" due to its preferred hybridization to "guanine". A(p) and A(pOq) are taken as modified PNA monomers acting as "adenine" for their tight affinity for "thymine". Likewise G(p) and G(pOq) are considered to be modified PNA monomers equivalent to "guanine" owing to their productive base pairing with "cytosine".

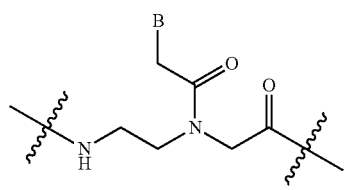
PNA Monomer
B: Nucleobase
p: Integer
q: Integer
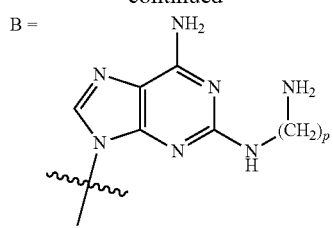
A(p)
Modified Adenine
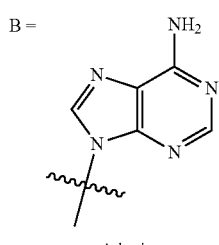   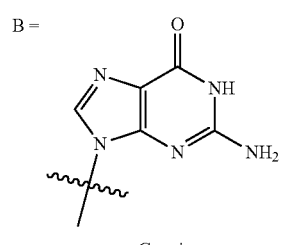
Adenine      Guanine
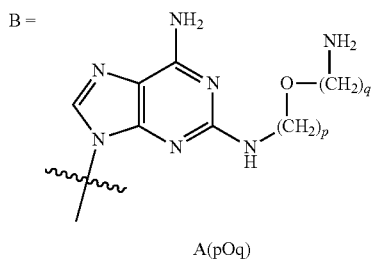
A(pOq)
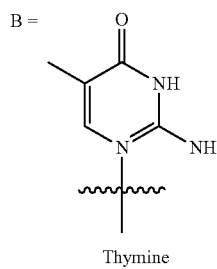   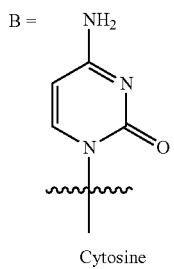
Thymine   Cytosine
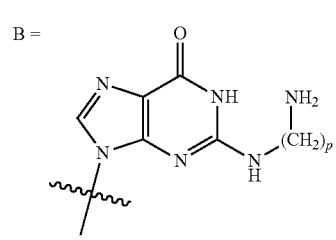
G(p)
Modified Guanine
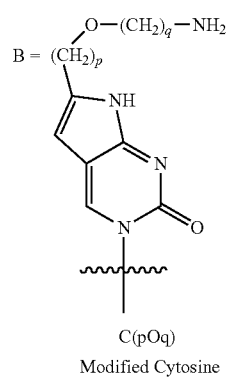
C(pOq)
Modified Cytosine
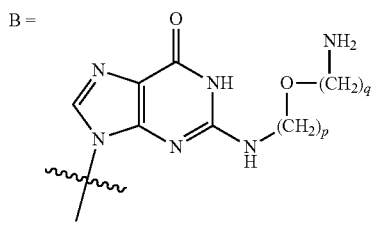
G(pOq)

Chemical structures or a variety of abbreviations or substituents use or diversifying the N-terminus or C-terminus of the PNA derivative of Formula I in this invention are provided below.
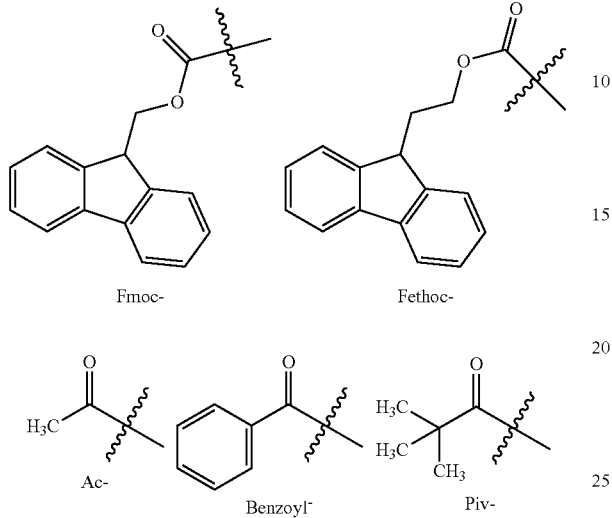
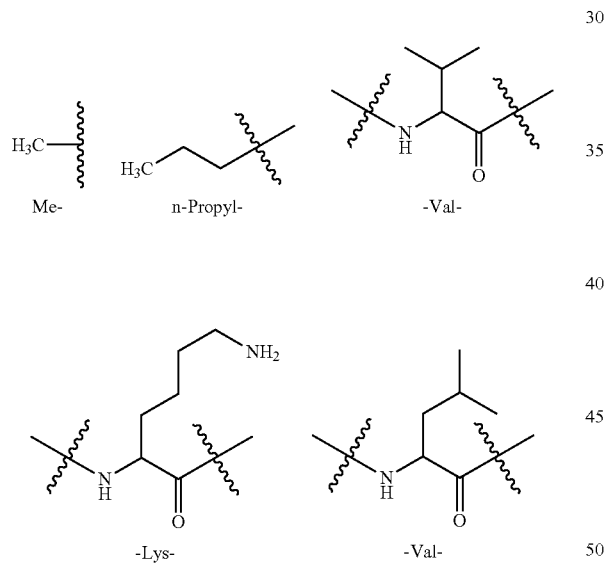
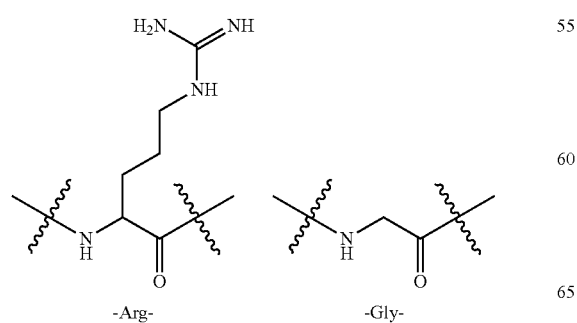
-continued
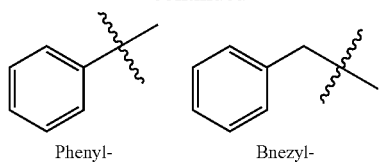
Phenyl-    Bnezyl-
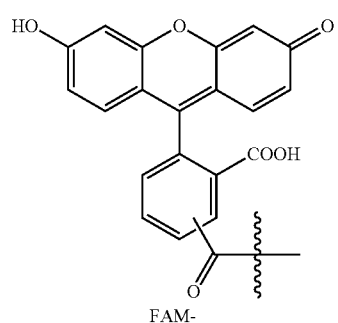
-Hex-
FAM-
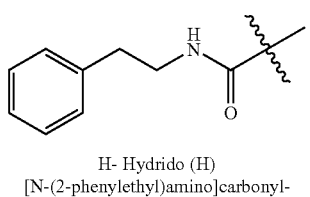
H- Hydrido (H)
[N-(2-phenylethyl)amino]carbonyl-

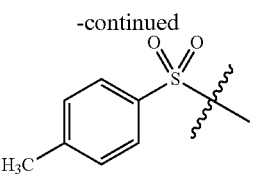
-NH₂ non-substituted amino
p-Toluenesulfonyl-
In order to illustrate the abbreviations for the PNA derivatives, the chemical structure for a 14-mer PNA derivative abbreviated as "(N→C) Fethoc-GA(5)A-C(1O2)TT-A(5)TC-CTA(5)-C(1O2)T-NH₂" is provided below.
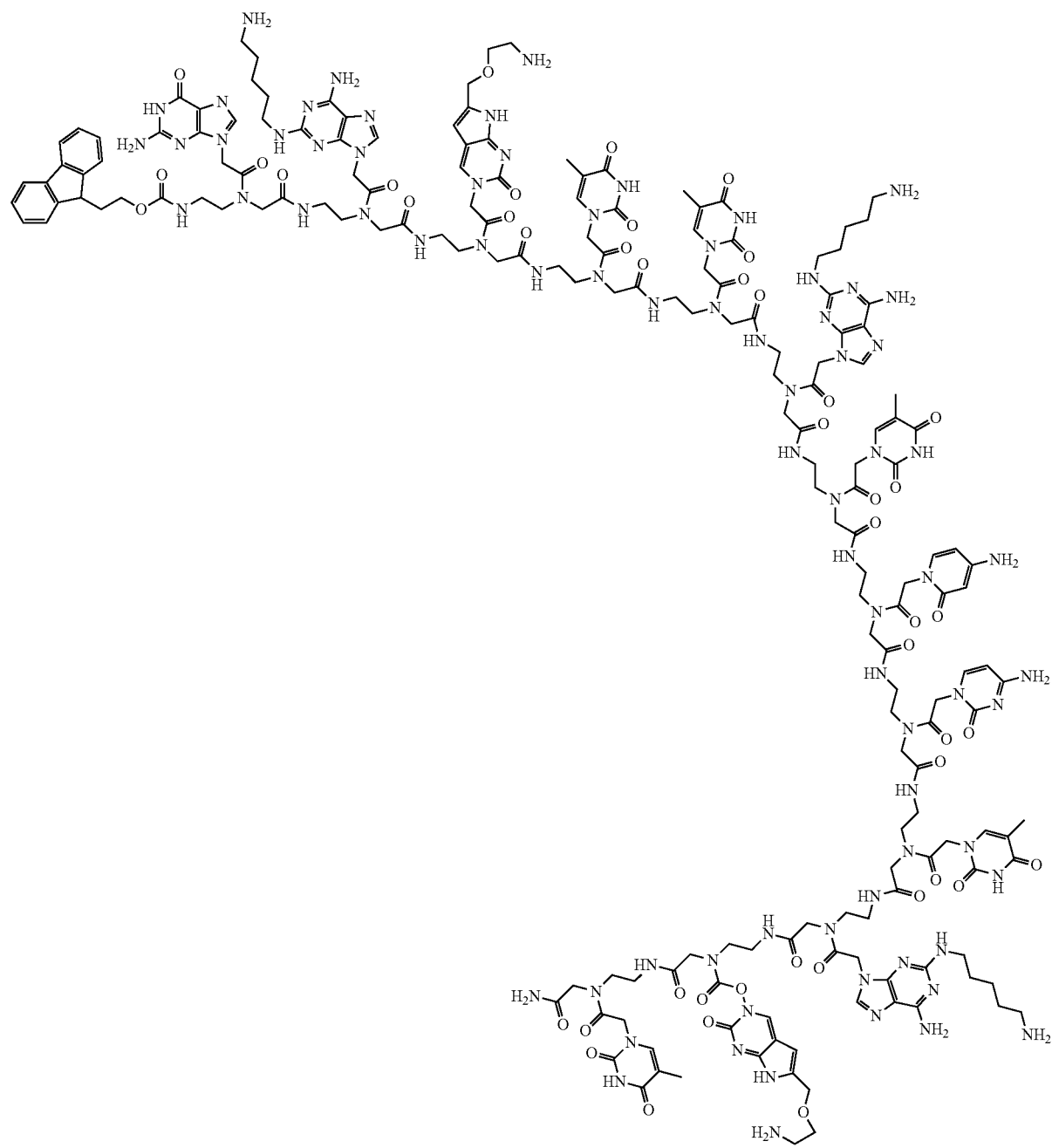

As another illustration, the chemical structure for a 15-mer PNA derivative abbreviated as "(N→C) Fmoc-Val-CTC(1O2)-A(5)TC-CTA(6)-C(1O3)TT-AA(2O2)C—NH₂" is provided below.

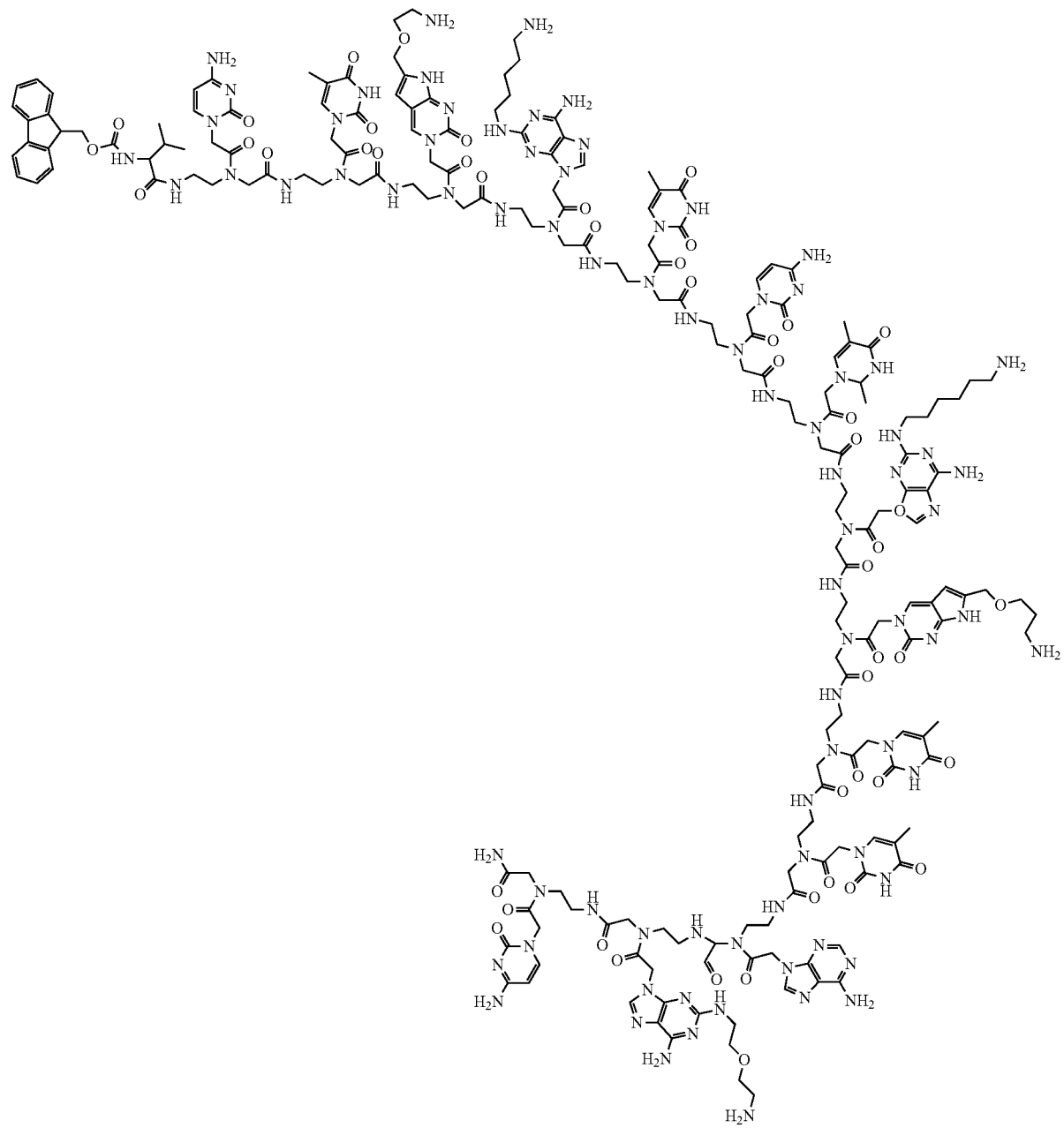

A 14-mer PNA derivative abbreviated as "(N→C) Fethoc-CA(5)G-AA(5)C-TTA(5)-TCC(1O2)-TA(5)-NH₂" is equivalent to the DNA sequence of "(5'→3') CAG-AAC-TTA-TCC-TA (SEQ ID NO: 4)" for complementary binding to pre-mRNA. The 14-mer PNA possesses a 14-mer complementary overlap with a 30-mer pre-mRNA sequence of [(5'→3') guuguuguuaaguag|GAUAAGUUCUGAACG (SEQ ID NO: 5)] spanning the junction of intron 1 and exon 2 in the human HIF-1α pre-mRNA with the complementary base pairings as marked "bold" and "underlined" in

[(5'→3') guuguuguuaaguag|
GAUAAGUUCUGAACG (SEQ ID NO: 5)].

A 15-mer PNA derivative abbreviated as "(N→C) Fethoc-CTC(1O2)-A(6)TC-CTA(6)-C(1O2)TT-AA(6)C—NH₂" is equivalent to the DNA sequence of "(5'→3') CAA-TTC-ATC-CTA-CTC (SEQ ID NO: 6)" for complementary binding to pre-mRNA. The 15-mer PNA possesses a 15-mer complementary overlap with the 30-mer human HIF-1α pre-mRNA sequence of [(5'→3') guuguuguuaaguag-

[GAUAAGUUCUGAACG (SEQ ID NO: 5)] with the complementary base pairings as marked "bold" and "underlined" in

[(5'→3') guuguuguuaaguag|GAUAAGUUCUGAACG (SEQ ID NO: 5)].

A 15-mer PNA sequence of "(N→C) Piv-Lys-AA(6)C-TTA(6)-TCC(1O2)-TA(6)C-TTA(5)-Val-NH$_2$" is equivalent to the DNA sequence of "(5'→3') ATT-CAT-CCT-ATT-CAA (SEQ ID NO: 7)" for complementary binding to pre-mRNA. The 15-mer PNA possesses a 15-mer complementary overlap with the 30-mer human HIF-1α pre-mRNA sequence of [(5'→3') guuguuguuaaguag|GAUAAGUU-CUGAACG (SEQ ID NO: 5)] with the complementary base pairings as marked "bold" and "underlined" in

[(5'→3') guuguuguuaaguag|GAUAAGUUCUGAACG (SEQ ID NO: 5)].

A 17-mer PNA derivative abbreviated as "(N→C) Fethoc-A(6)GA-A(6)CT-CA(6)T-CC(1O2)T-A(6)CT-TA(6)-NH$_2$" is equivalent to the DNA sequence of "(5'→3') AGA-ACT-CAT-CCT-ACT-TA (SEQ ID NO: 8)" for complementary binding to pre-mRNA. The 17-mer PNA possesses a 16-mer complementary overlap and a single mismatch against the 30-mer the human HIF-1α pre-mRNA sequence of [(5'→3') guuguuguuaaguag|GAUAAGUUCUGAACG (SEQ ID NO: 5)]. The complementary base pairings are marked "bold" and "underlined", and the single mismatch is marked with a quote sign (" ") as in

[(5'→3') guuguuguuaaguag|GAU"A"AGUUCUGAACG (SEQ ID NO: 5)].

Despite the single mismatch, this 17-mer PNA meets the structural requirements for the compound of Formula I. Thus the 17-mer PNA derivative belongs to the compound of Formula I.

In some embodiments, the present invention provides a PNA derivative of Formula I which is selected from the group of specific compounds enlisted below, or a pharmaceutically acceptable salt thereof:

(N→C) Fethoc-CA(5)G-AA(5)C-TTA(5)-TCC(1O2)-TA(5)-NH$_2$;

(N→C) Fethoc-GA(5)A-C(1O2)TT-A(5)TC-CTA(5)-C(1O2)T-NH$_2$;

(N→C) Fethoc-G(5)AA(5)-CTT-A(5)TC-CTA(5)-C(1O2)T-NH$_2$;

(N→C) Fethoc-GA(5)A-C(1O2)TT-A(5)TC-CTA(5)-CT-NH$_2$;

(N→C) Fethoc-G(5)AA(6)-CTT-A(6)TC-CTA(6)-C(1O2)T-NH$_2$;

(N→C) Fethoc-A(6)GA-A(6)CT-TA(6)T-CC(1O2)T-A(6)CT-TA(6)-NH$_2$;

(N→C) Fethoc-C(105)TT-A(6)TC-CTA(6)-C(1O2)TT-AA(6)C-NH$_2$;

(N→C) Fethoc-CTC(1O2)-A(6)TC-CTA(6)-C(1O2)TT-AA(6)C-NH$_2$;

(N→C) Piv-Lys-AA(6)C-TTA(6)-TCC(1O2)-TA(6)C-TTA(5)-Val-NH$_2$;

(N→C) Benzoyl-CA(5)G(2O3)-AA(5)C-TTA(4)-TCC(1O2)-TA(5)-NH$_2$;
and (N→C) p-Toluenesulfonyl-CA(5)G-AA(5)C-TTA(2O2)-TCC(1O2)-TA(5)-NH$_2$.

In some embodiments, the present invention provides a PNA derivative of Formula I which is selected from the group of specific compounds enlisted below, or a pharmaceutically acceptable salt thereof:

(N→C) Fethoc-CTT-A(6)TC(105)-CTA(6)-C(1O2)TT-A(5)AC-NH$_2$;

(N→C) Fethoc-C(105)TT-A(6)TC-CTA(6)-C(1O2)TT-A(5)AC(105)-A-NH$_2$;

(N→C) Fethoc-AC(1O2)T-TA(5)T-CC(1O2)T-A(6)C(1O2)T-TA(5)A-C-NH$_2$;

(N→C) Fethoc-CTT-A(6)TC-CTA(6)-C(1O2)TT-A(5)AC-NH$_2$;

(N→C) Piv-AC(1O2)T-TA(5)T-CC(1O2)T-A(6)C(1O2)T-TA(5)A-C-NH$_2$;

(N→C) Fethoc-Lys-AC(1O2)T-TA(5)T-CC(1O2)T-A(6)C(1O2)-T-TA(5)A-CNH$_2$;

(N→C) Fethoc-CTC(1O2)-A(6)TC-CTA(6)-C(1O2)TT-AA(6)C-NH$_2$;

(N→C) Fethoc-A(6)GA-A(6)CT-TA(6)T-CC(1O2)T-A(6)CT-TA(6)-NH$_2$;

(N→C) Piv-AG(5)A-A(2O2)CT-TA(5)T-CC(1O2)T-A(6)CT-TA-NH$_2$;

(N→C) Fethoc-A(5)GA(5)-AC(103)T-TA(5)T-CC(1O2)T-A(6)CT-TA(4)-NH$_2$;

(N→C) Fethoc-GA(5)A-C(1O2)TT-A(5)TC-CTA(5)-C(1O2)T-NH$_2$;

(N→C) Benzoyl-GA(5)A-C(1O2)TT-A(5)TC-CTA(5)-C(1O2)T-NH$_2$;

(N→C) Fethoc-G(5)AA(5)-CTT-A(5)TC-CTA(5)-C(1O2)T-NH$_2$;

(N→C) Fethoc-GA(5)A-C(1O2)TT-A(5)TC-CTA(5)-CT-NH$_2$;

(N→C) Fethoc-G(5)AA(6)-CTT-A(6)TC-CTA(6)-C(1O2)T-NH$_2$;
and (N→C) Fethoc-CA(5)G-AA(5)C-TTA(5)-TCC(1O2)-TA(5)-NH$_2$;

DETAILED DESCRIPTION OF INVENTION

General Procedures for Preparation of PNA Oligomers

PNA oligomers were synthesized by solid phase peptide synthesis (SPPS) based on Fmoc-chemistry according to the method disclosed in the prior art [U.S. Pat. No. 6,133,444; WO96/40685] with minor but due modifications. The solid support employed in this study was H-Rink Amide-ChemMatrix purchased from PCAS BioMatrix Inc. (Quebec, Canada). Fmoc-PNA monomers with a modified nucleobase were synthesized as described in the prior art [PCT/KR 2009/001256] or with minor modifications. Such Fmoc-PNA monomers with a modified nucleobase and Fmoc-PNA monomers with a naturally-occurring nucleobase were used to synthesize the PNA derivatives of the present invention. PNA oligomers were purified by Cis-reverse phase HPLC (water/acetonitrile or water/methanol with 0.1% TFA) and characterized by mass spectrometry.

Scheme 1 illustrates a typical monomer elongation cycle adopted in the SPPS of this invention, and procedural details are provided below. To a skilled person in the field, however, minor variations are obviously possible in order to run effectively SPPS reactions on an automatic peptide synthesizer or manual peptide synthesizer. Each reaction step in Scheme 1 is briefly provided as follows.

[Activation of H-Rink-ChemMatrix Resin] 0.01 mmol (ca 20 mg resin) of the ChemMatrix resin in 1.5 mL 20% piperidine/DMF was vortexed in a libra tube for 20 min, and the DeFmoc solution was filtered off. The resin was washed for 30 sec each in series with 1.5 mL methylene chloride (MC), 1.5 mL dimethylformamide (DMF), 1.5 mL MC, 1.5 mL DMF, and 1.5 mL MC. The resulting free amines on the solid support were subjected to coupling either with an Fmoc-PNA monomer or with an Fmoc-protected amino acid derivative.

[DeFmoc] The resin was vortexed in 1.5 mL 20% piperidine/DMF for 7 min, and the DeFmoc solution was filtered off. The resin was washed for 30 sec each in series with 1.5 mL MC, 1.5 mL DMF, 1.5 mL MC, 1.5 mL DMF, and 1.5 mL MC. The resulting free amines on the solid support were immediately subjected to coupling with an Fmoc-PNA monomer.

[Coupling with Fmoc-PNA Monomer] The free amines on the solid support were coupled with an Fmoc-PNA monomer as follows. 0.04 mmol of PNA monomer, 0.05 mmol HBTU, and 10 mmol DIEA were incubated for 2 min in 1 mL anhydrous DMF, and added to the resin with free amines. The resin solution was vortexed for 1 hour and the reaction medium was filtered off. Then the resin was washed for 30 sec each in series with 1.5 mL MC, 1.5 mL DMF, and 1.5 mL MC. The chemical structures of Fmoc-PNA monomers with a modified nucleobase used in this invention are provided below. The Fmoc-PNA monomers with a modified nucleobase are provided below should be taken as examples, and therefore should not be taken to limit the scope of the present invention. A skilled person in the field may easily figure out a number of variations in Fmoc-PNA monomers to synthesize the PNA derivative of Formula I.

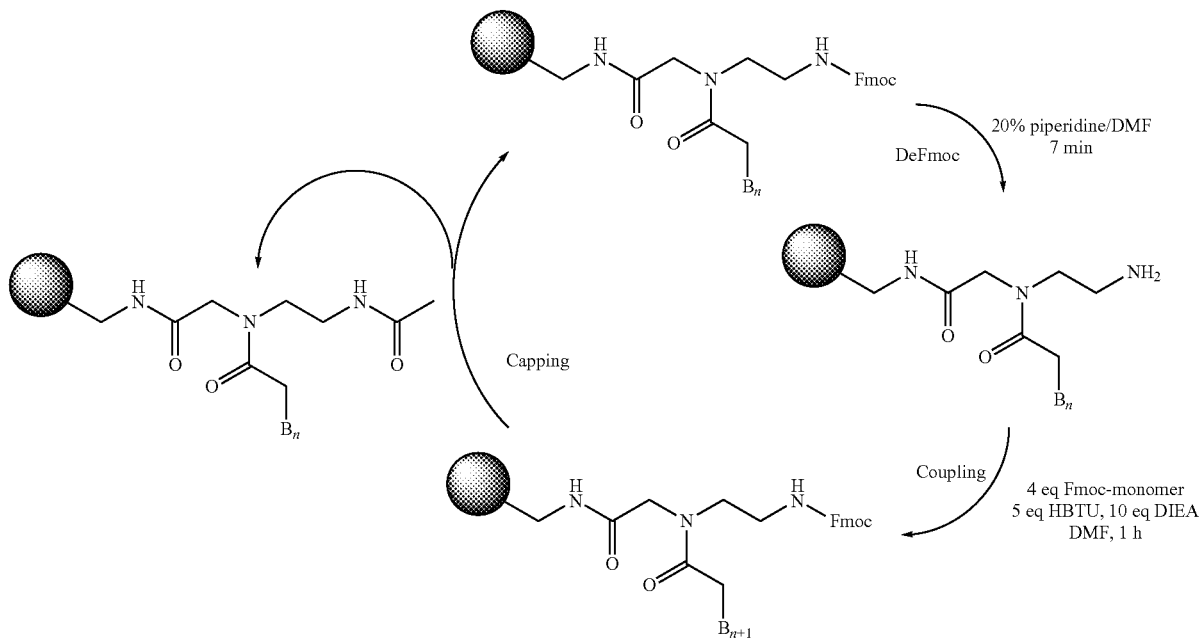

Scheme 1

Fmoc-PNA Monomer

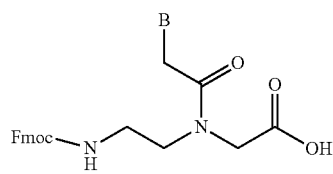

B: Nucleobase with protecting group(s)
X: methylene, oxygen, sulfur, or Boc-protected amino
m: Integer
n: Integer

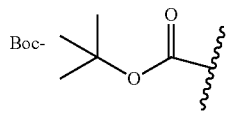

Modified Cytosine

C(mXn): B =

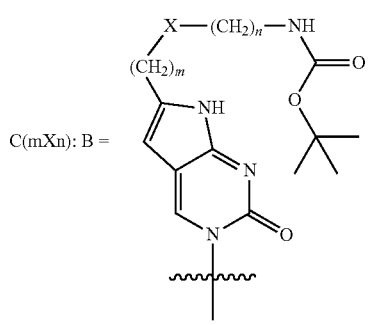

Modified Adenine

A(mXn): B =

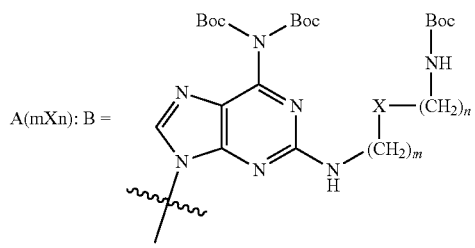

Modified Guanine

G(mXn): B =

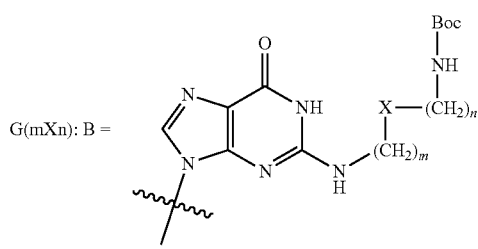

[Capping] Following the coupling reaction, the unreacted free amines were capped by shaking for 5 min in 1.5 mL capping solution (5% acetic anhydride and 6% 2,6-leutidine in DMF). Then the capping solution was filtered off and washed for 30 se each in series with 1.5 mL MC, 1.5 mL DMF, and 1.5 mL MC.

[Introduction of "Fethoc-" Radical in N-Terminus] "Fethoc-" radical was introduced to the N-terminus by reacting the free amine on the resin with "Fethoc-OSu" under basic coupling conditions. The chemical structure of "Fethoc-OSu" [CAS No. 179337-69-0, $C_{20}H_{17}NO_5$, MW 351.36] is provided as follows.

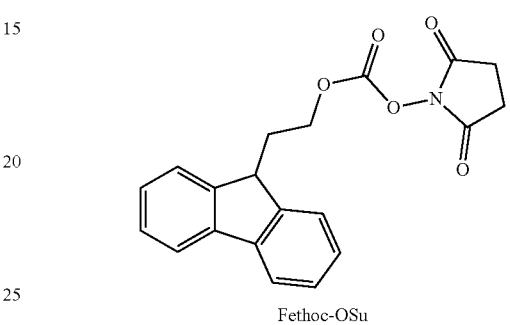

Fethoc-OSu

[Cleavage from Resin] PNA oligomers bound to the resin were cleaved from the resin by shaking for 3 hours in 1.5 mL cleavage solution (2.5% tri-isopropylsilane and 2.5% water in trifluoroacetic acid). The resin was filtered off and the filtrate was concentrated under reduced pressure. The residue was triturated with diethylether, and the resulting precipitate was collected by filtration for purification by reverse phase HPLC.

Figure 7A:
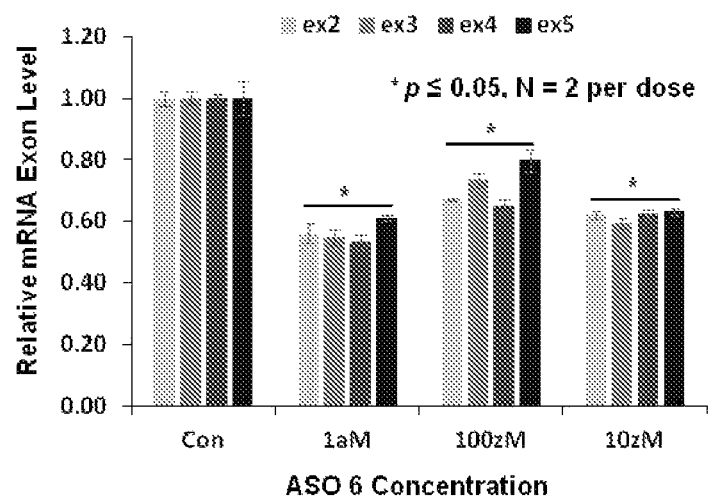
FIG. 7A. Nested qPCR data by SYBR Green in HeLa cells treated with "ASO 6" at 0 (negative control), 10, 100 or 1,000 zM. (error bar by standard error)
Figure 7B:
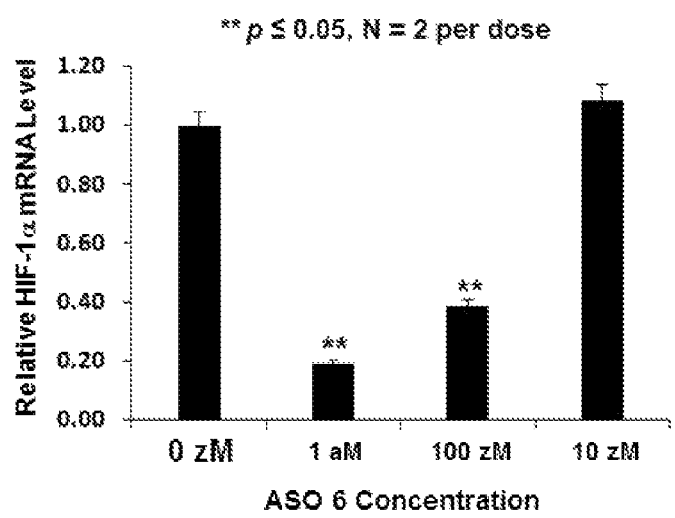
FIG. 7B. Nested qPCR data by TaqMan probe in HeLa cells treated with "ASO 6" at 0 (negative control), 10, 100 or 1,000 zM. (error bar by standard error)

[HPLC Analysis and Purification] Following a cleavage from resin, the crude product of a PNA derivative was purified by Cis-reverse phase HPLC eluting water/acetonitrile or water/methanol (gradient method) containing 0.1% TFA. FIGS. 7A and 7B are exemplary HPLC chromatograms for "ASO 1" before and after HPLC purification, respectively. The oligomer sequence of "ASO 1" is as provided in Table 1.

Synthetic Examples for PNA Derivatives of Formula I

PNA derivatives of this invention were prepared according to the synthetic procedures provided above or with minor modifications. Table 1 provides examples of HIF-1α ASOs of the present invention along with structural characterization data by mass spectrometry. Provision of the HIF-1α ASOs in Table 1 is to exemplify the PNA derivatives of Formula I, and should not be interpreted to limit the scope of the present invention.

TABLE 1

PNA derivatives of Formula I and structural identification by mass spectrometry.

| PNA | PNA Sequence (N→C) | Exact Mass, m/z Theor.[a] | Obs.[b] |
|---|---|---|---|
| ASO 1 | Fethoc-CA(5)G-AA(5)C-TTA(5)-TCC(102)-TA(5)-NH₂ | 4486.05 | 4486.04 |
| ASO 2 | Fethoc-GA(5)A-C(102)TT-A(5)TC-CTA(5)-C(102)T-NH₂ | 4473.99 | 4474.02 |
| ASO 3 | Fethoc-G(5)AA(5)-CTT-A(5)TC-CTA(5)-C(102)T-NH₂ | 4462.03 | 4462.07 |

TABLE 1-continued

PNA derivatives of Formula I and structural identification by mass spectrometry.

| PNA | PNA Sequence (N→C) | Exact Mass, m/z Theor.[a] | Obs.[b] |
|---|---|---|---|
| ASO 4 | Fethoc-GA(5)A-C(1O2)TT-A(5)TC-CTA(5)-CT-NH$_2$ | 4376.94 | 4376.99 |
| ASO 5 | Fethoc-G(5)AA(6)-CTT-A(6)TC-CTA(6)-C(1O2)T-NH$_2$ | 4504.07 | 4504.09 |
| ASO 6 | Fethoc-A(6)GA-A(6)CT-TA(6)T-CC(1O2)T-A(6)CT-TA(6)-NH$_2$ | 5393.47 | 5393.44 |
| ASO 7 | Fethoc-C(1O5)TT-A(6)TC-CTA(6)-C(1O2)TT-AA(6)C-NH$_2$ | 4784.18 | 4784.14 |
| ASO 8 | Fethoc-CTC(1O2)-A(6)TC-CTA(6)-C(1O2)TT-AA(6)C-NH$_2$ | 4727.13 | 4727.79 |
| ASO 9 | Piv-A(6)TC-CTA(6)-C(1O2)TT-A(5)AC-NH$_2$ | 3695.73 | 3695.74 |
| ASO 10 | Piv-Lys-AA(6)C-TTA(6)-TCC(1O2)-TA(6)C-TTA(5)-Val-NH$_2$ | 4844.33 | 4844.33 |
| ASO 11 | Fethoc-A(6)GA-A(6)CT-CA(6)T-CC(1O2)T-A(6)CT-TA(6)-NH$_2$ | 5448.54 | 5448.50 |
| ASO 12 | H-CA(5)G-AA(5)C-TTA(5)-T CC(1O3)-TA(5)-NH$_2$ | 4263.98 | 4263.99 |
| ASO 13 | Benzoyl-CA(5)G(2O3)-AA(5)C-TTA(4)-TCC(1O2)-TA(5)-NH$_2$ | 4441.06 | 4441.06 |
| ASO 14 | n-Propyl-CA(5)G-AA(5)C-TTA(5)-TCC(2O2)-TA(5)-NH$_2$ | 4306.03 | 4306.05 |
| ASO 15 | p-Toluenesulfonyl-CA(5)G-AA(5)C-TTA(2O2)-TCC(1O2)-TA(5)-NH$_2$ | 4405.95 | 4405.90 |
| ASO 16 | +N-(2-Phenylethyl)aminolcarbonyl-CA(5)G(3)-AA(5)C-TTA(3)-TCC(1O2)-TA(5)-NH$_2$ | 4426.06 | 4426.08 |
| ASO 17 | Fethoc-Lys-Leu-CA(5)G(2O2)-AA(5)C-TTA(8)-TCC(1O2)-TA(5)-Lys-NH$_2$ | 4984.44 | 4984.46 |
| ASO 18 | N-Ph-N-Me-CA(5)G-AA(5)C-TTA(5)-TCC(1O2)-TA(5)-Lys-NH$_2$ | 4468.11 | 4468.14 |

[a]theoretical exact mass,
[b]observed exact mass

Figure 1B:
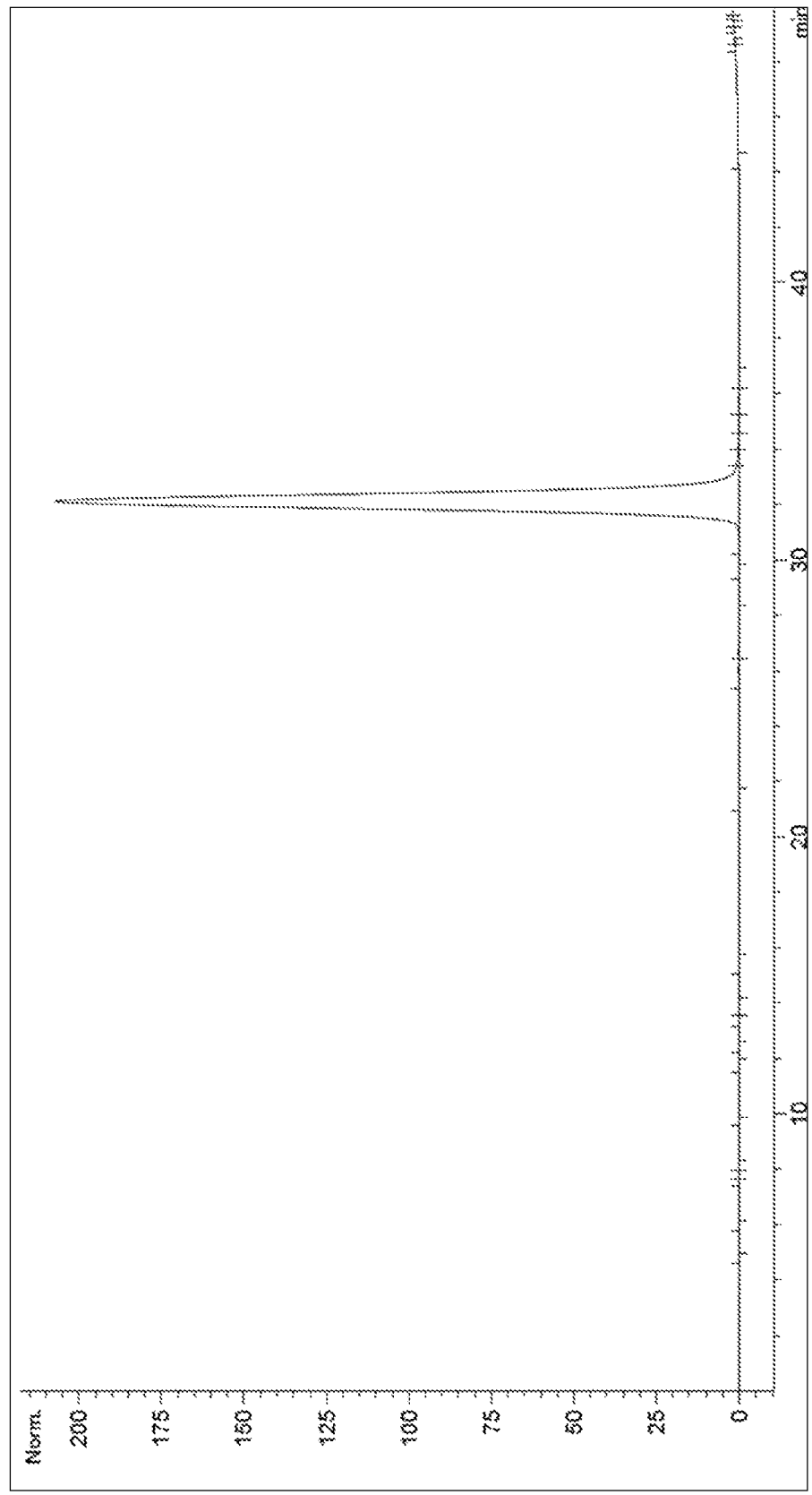
FIG. 1B. $C_{18}$-reverse phase HPLC chromatogram of "ASO 1" after preparatory HPLC purification.
Figure 2:
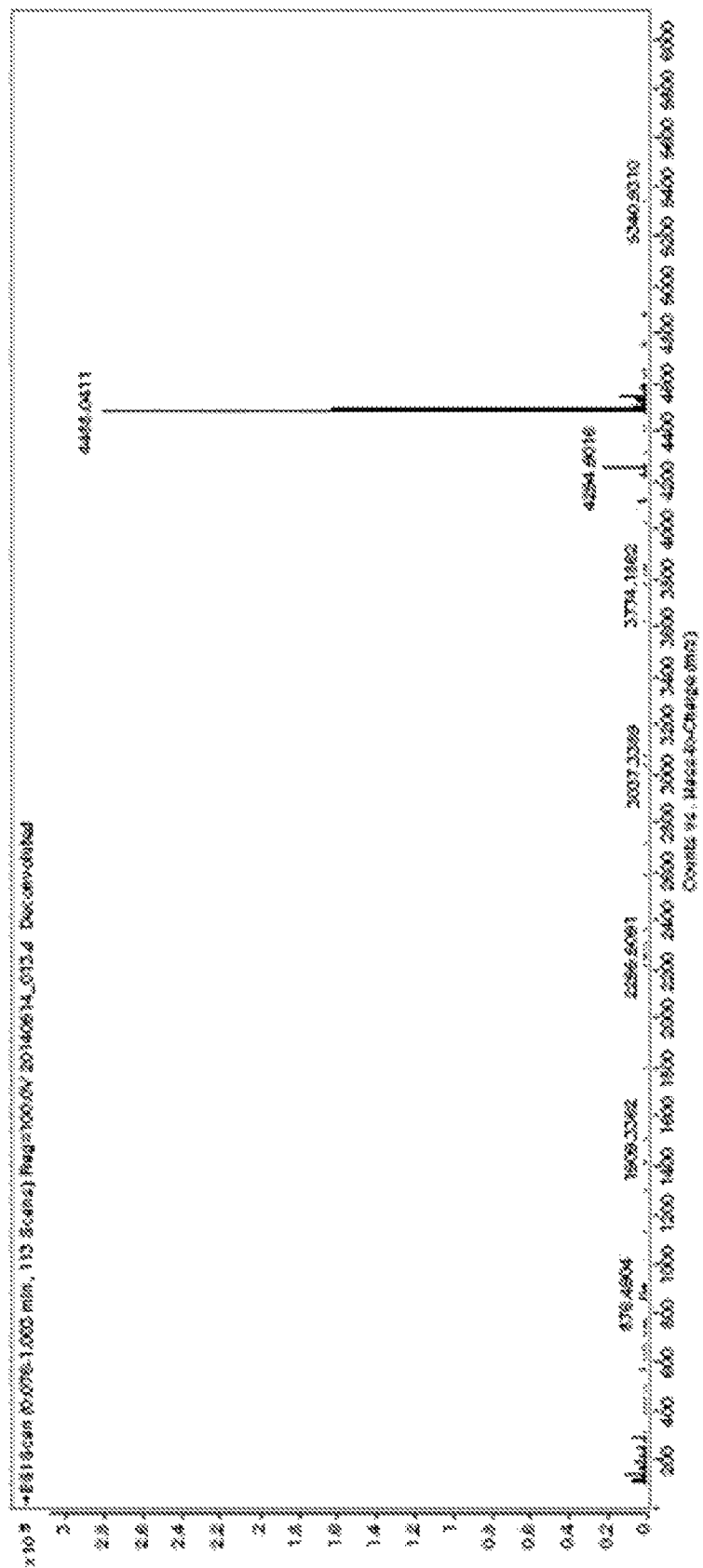
FIG. 2. ESI-TOF mass spectrum of "ASO 1" after purification by $C_{18}$—RP prep HPLC.

FIG. 1A is a HPLC chromatogram obtained with a crude product of ASO 1. The crude product was purified by C$_{18}$-RP preparatory HPLC. FIG. 1B is a HPLC chromatogram for a purified product of ASO 1. The purity of ASO 1 improved markedly by the preparatory HPLC purification. FIG. 2 provides an ESI-TOF mass spectrum obtained with the purified product of ASO 1. Provision of the analysis data for ASO 1 is to illustrate how the PNA derivatives of Formula I were purified and identified in the present invention, and should not be interpreted to limit the scope of this invention.

Binding Affinity of PNA for 10-mer Complementary DNA

The PNA derivatives in Table 1 were evaluated for their binding affinity for 10-mer DNAs complementarily targeting either the N-terminal or C-terminal. The binding affinity was assessed by $T_m$ value for the duplex between PNA and 10-mer complementary DNA. The duplex between PNA derivatives in Table 1 and fully complementary DNAs show $T_m$ values too high to be reliably determined in aqueous buffer solution, since the buffer solution tends to boil off during the $T_m$ measurement. $T_m$ values were determined on an UV/Vis spectrometer as follows or with minor modifications.

A mixed solution of 4 μM PNA oligomer and 4 μM complementary 10-mer DNA in 4 mL aqueous buffer (pH 7.16, 10 mM sodium phosphate, 100 mM NaCl) in 15 mL polypropylene falcon tube was incubated at 90° C. for a minute and slowly cooled down to ambient temperature over several minutes. Then the solution was transferred into a 3 mL quartz UV cuvette equipped with an air-tight cap, and subjected to a $T_m$ measurement at 260 nm on a UV/Visible spectrophotometer as described in the prior art [PCT/KR2009/001256] or with minor modifications. The 10-mer complementary DNAs for $T_m$ measurement were purchased from Bioneer (www.bioneer.com, Dajeon, Republic of Korea) and used without further purification.

Observed $T_m$ values of the PNA derivatives of Formula I are high for a complementary binding to 10-mer DNAs for their low G/C content, and provided in Table 2. For example, "ASO 8" showed a $T_m$ value of 73.0° C. for the duplex with the 10-mer complementary DNA targeting the N-terminal 10-mer within the PNA marked as "bold" and "underlined" in [(N→C) Fethoc-CTC(1O2)-A(6)TC-CTA(6)-C(1O2)TT-AA(6)C—NH$_2$]. In the meantime, "ASO 8" showed a $T_m$ of 61.0° C. for the duplex with the 10-mer complementary DNA targeting the C-terminal 10-mer within the PNA marked as "bold" and "underlined" in [(N→C) Fethoc-CTC(1O2)-A(6)TC-CTA(6)-C(1O2)TT-AA(6)C—NH$_2$].

TABLE 2

$T_m$ values between PNAs in Table and 10-mer complementary DNA targeting either the N-terminal or the C-terminal of PNA.

| PNA | $T_m$ Value, °C. | |
|---|---|---|
| | 10-mer DNA against N-Terminal | 10-mer DNA against C-Terminal |
| ASO 1 | 66.0 | 60.0 |
| ASO 4 | 66.0 | 53.4 |
| ASO 5 | 62.0 | 58.0 |
| ASO 7 | 69.0 | 61.0 |
| ASO 8 | 73.0 | 61.0 |
| ASO 9 | 60.9 | 59.0 |
| ASO 10 | 61.0 | 60.0 |
| ASO 11 | 73.4 | 61.0 |

Examples for Biological Activities for PNA Derivatives of Formula I

PNA derivatives of Formula I were evaluated for the in vitro antisense activity in HeLa cells, and for the antitumor activity in nude mice with tumor xenograft. These biological examples were provided as examples to illustrate the biological profiles of the PNA derivatives of Formula I, and therefore should not be interpreted to limit the scope of the current invention.

Example 1. Exon Skipping Induced by "ASO 2"

"ASO 2" specified in Table 1 is a 14-mer ASO complementarily binding to the 3' splice site of exon 2 in the human HIF-1α pre-mRNA with the complementary overlaps as marked "bold" and "underlined" in the 30-mer pre-mRNA sequence of

```
[(5'→3')
guuguuguuaaguag|GAUAAGUUCUGAACG
(SEQ ID NO: 5)].
```

"ASO 2" possesses a 5-mer overlap with intron 1 and a 9-mer overlap with exon 2.

"ASO 2" was evaluated by nested RT-PCR for its ability to induce the skipping of exon 2 of the human HIF-1α mRNA in HeLa cells. The employed procedures are as provided below.

[Cell Culture & ASO Treatment] HeLa cells (Cat. Number CCL-2, ATCC) were sub-cultured in 60 mm culture dish containing 5 mL EMEM medium supplemented with 10% FBS, 1% streptomycin/penicillin, 1% L-glutamine, and 1% sodium pyruvate under 5% $CO_2$ at 37° C. The cells were treated with "ASO 2" at 0 (i.e. negative control), 10, 100 or 1,000 zM.

[RNA Extraction] After 5 hours, total RNA was extracted using "Universal RNA Extraction Kit" (Cat. Number 9767, Takara) according to the manufacturer's instructions.

[cDNA Synthesis by One Step RT-PCR] 200 ng of RNA template was subjected to a 25 µL reverse transcription reaction using Super Script® One-Step RT-PCR kit with Platinum© Taq polymerase (Cat. Number 10928-042, Invitrogen) against a set of exon-specific primers [exon 1_forward: (5'→3') CTTGCCTTTCCTTCTCTTCT (SEQ ID NO: 9); exon 8_reverse: (5'→3') AACCCAGACA-TATC-CACC (SEQ ID NO: 10)] according to the following cycle conditions: 50° C. for 30 min and 94° C. for 2 min, followed by 15 cycles of 30 sec at 94° C., 30 sec at 55° C., and 1 min at 72° C.

[Nested PCR] 1 µL of cDNA was subjected to a 20 µL nested PCR reaction (Cat. Number K2612, Bioneer) against a set of exon-specific primers [exon 1n_forward: (5'→3') TGAAGACA-TCGCGGGGAC (SEQ ID NO: 11); exon 5n_reverse: (5'→3') TTTTTCACAAGGCCATTTCT (SEQ ID NO: 12)] according to the following cycle conditions: 95° C. for 5 min followed by 39 cycles of 30 sec at 95° C., 40 sec at 50° C., and 50 sec at 72° C.

Figure 3A:
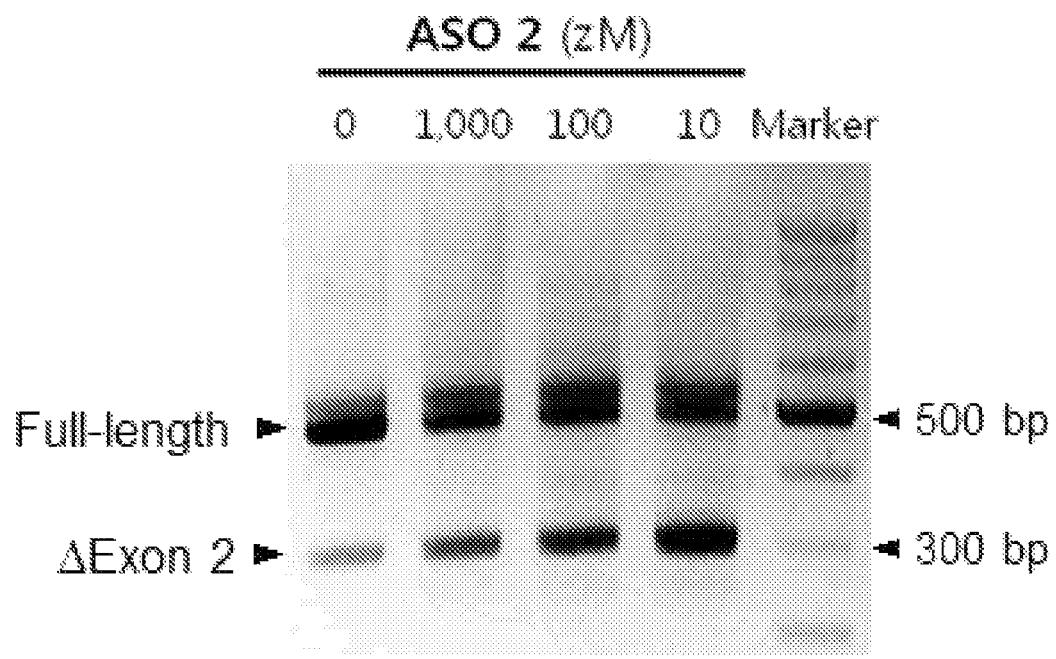
FIG. 3A. Electrophoresis data of HIF-1α nested RT-PCR products in HeLa cells treated with "ASO 2" at 0 (negative control), 10, 100 or 1,000 zM.
Figure 3B:
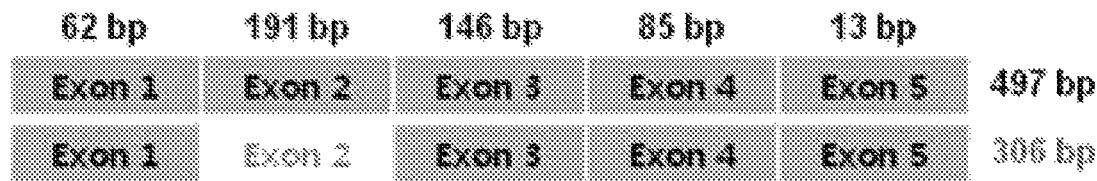
FIG. 3B. The predicted size of the PCR bands.
Figure 3C:
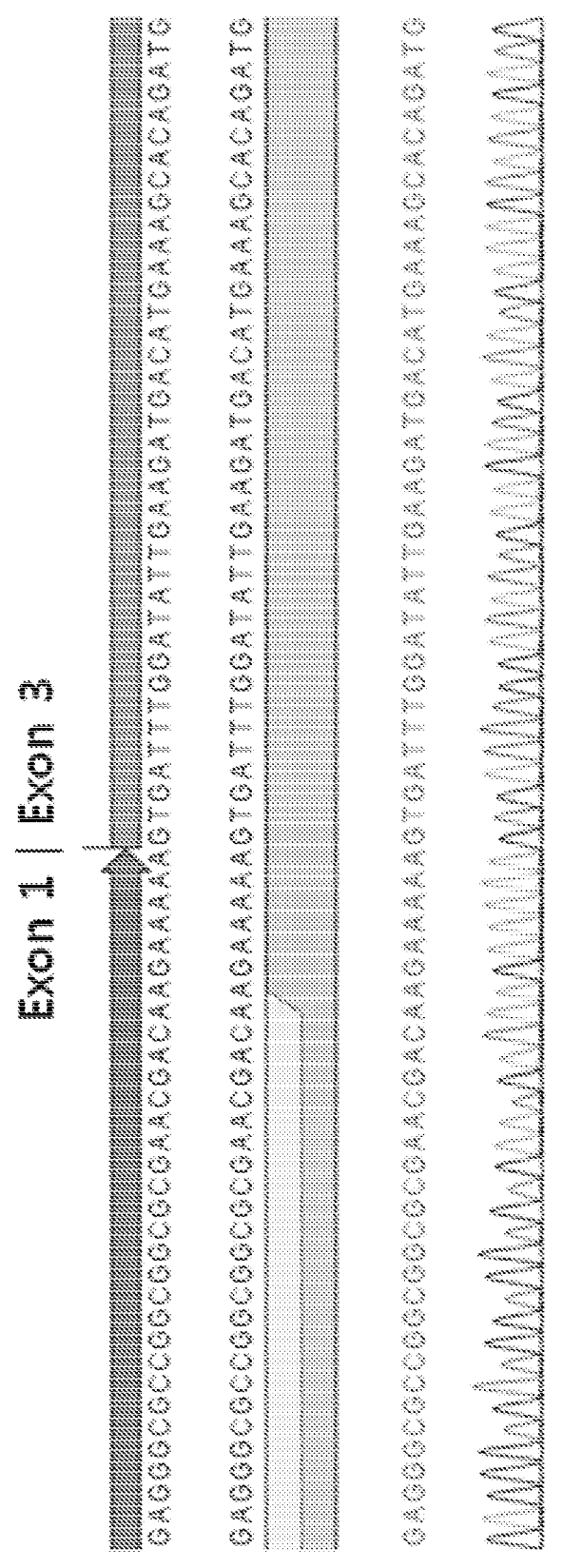

[Identification of Exon Skipping] The PCR products were subjected to electrophoretic separation on a 2% agarose gel along with a size marker cocktail. The bands of target size were collected and analyzed by Sanger Sequencing. The observed PCR bands corresponded to the full-length mRNA (i.e., without exon skipping), and the splice variant lacking exon 2 as marked in FIG. 3A. The cells treated with the ASO yielded a strong PCR band of a size assignable to the skipping of exon 2. The cells without the ASO treatment (i.e., negative control) also yielded the PCR product corresponding to the skipping of exon 2, suggesting that exon 2 is spontaneously deleted to a certain extent. However, the intensity of the exon skipping band was much stronger in the cells treated with the ASO than in the cells without ASO treatment. Thus "ASO 2" promoted the skipping of exon 2 in HeLa cells. The sequencing data for the exon skipping band are provided in FIG. 3C, and manifests the mRNA sequence for the junction of exon 1 and exon 3.

Example 2. Inhibition of HIF-1α Protein Expression in HeLa Cells by "ASO 2"

"ASO 2" was evaluated for its ability to inhibit the expression of HIF-1α protein in HeLa cells as described below.

[Cell Culture & ASO Treatment] HeLa cells grown in 5 mL medium in 60 mm culture were treated with "ASO 2" at 0 zM (negative control), 10 zM, 100 zM, 1 aM, or 10 aM.

[$CoCl_2$ Treatment and Cell Lysis] 24 hours after the ASO treatment, the culture dishes except for the one without ASO treatment were treated with 200 µM $CoCl_2$ for 3 hours to suppress the activity of prolylhydroxylases (PHDs). Then the cells were washed 2× with 1 mL cold PBS, and subjected to lysis on ice with 200 µL 1× RIPA buffer (Cat. Number 9806, Cell Signaling Tech) supplemented with 1% SDS and 1× proteinase inhibitor cocktail (cOmplete Mini, Roche). Then the lysates were collected in 1.5 mL e-tube, mixed with 100 µL 5× sample buffer, and boiled for 5 min at 100° C. The lysates were subjected to electrophoretic separation on an 8% SDS-PAGE gel, and transferred onto a 0.45 µm PVDF membrane. The membrane was probed with anti-HIF-1α antibody (Cat. Number 610958, BD Biosciences) and anti-β-actin antibody (Cat. Number sc4778, Santa Cruz).

Figure 4A:
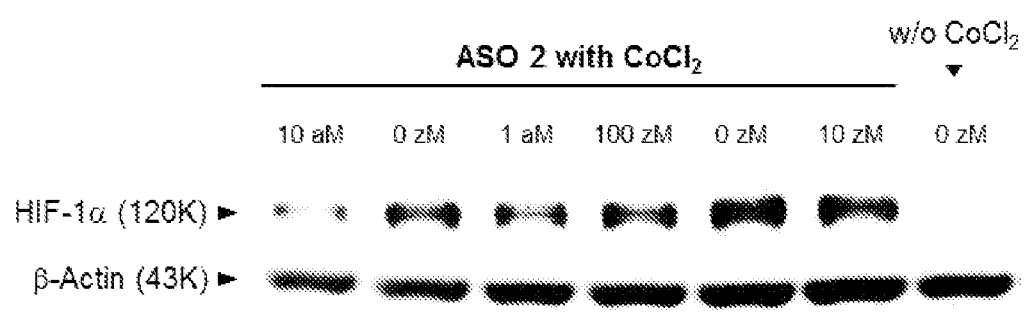
FIG. 4A. HIF-1α western blot data in HeLa Cells treated with "ASO 2" at 0 zM (negative control), 10 zM, 100 zM, 1 aM or 10 aM for 24 hours.

[Inhibition of HIF-1α Protein Expression] FIG. 4A provides the HIF-1α western blot data obtained with HeLa cells treated with "ASO 2". There was no HIF-1α band detected with the lysate of the cells without $CoCl_2$ treatment. The lysates of the cells with $CoCl_2$ treatment showed a strong band for HIF-1α, indicating a marked suppression of PHDs activity by $CoCl_2$.

Figure 4B:
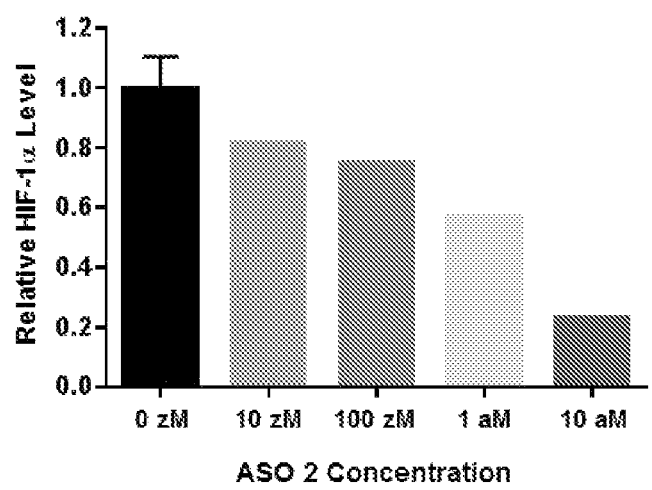
FIG. 4B. HIF-1α expression levels normalized against β-actin in HeLa cells treated with "ASO 2" at 0 zM (negative control), 10 zM, 100 zM, 1 aM or 10 aM for 24 hours.

FIG. 4B provides the individual HIF-1α band intensities against individual β-actin band intensity by densitometry. The HIF-1α expression gradually decreased as the "ASO 2"

concentration was increased to 10 aM. The observed decrease was ca 75% at 10 aM "ASO 2".

Example 3. qPCR by SYBR Green for HIF-1α mRNA in HeLa Cells Treated with "ASO 2"

"ASO 2" was evaluated by nested qPCR for its ability to inhibit the expression of the full-length HIF-1α mRNA in HeLa cells as described below.

[Cell Culture & ASO Treatment] HeLa cells grown in 5 mL medium in 60 mm culture were treated with "ASO 2" at 0 (negative control), 10, 100 or 1,000 zM (2 culture dishes per each ASO concentration).

[RNA Extraction] 3 hours after the ASO treatment, total RNA was extracted by "MiniBEST Universal RNA Extraction Kit" (Cat. Number 9767, Takara) according to the manufacturer's instructions.

[cDNA Synthesis by One Step RT-PCR] 200 ng of RNA template subjected to a 25 µL reverse transcription reaction using Super Script® One-Step RT-PCR kit with Platinum® Taq polymerase (Cat. Number 10928-042, Invitrogen) against a set of exon-specific primers [exon 1_forward: (5'→3') CTTGCCTTTCCTTCTCTTCT (SEQ ID NO: 9); exon 8_reverse: (5'→3') AACCCAGACA-TATCCACC (SEQ ID NO: 10)] according to the following cycle conditions: 50° C. for 30 min and 94° C. for 2 min, followed by 15 cycles of 30 sec at 94° C., 30 sec at 55° C., and 1 min at 72° C.

[Nested qPCR] 1 µL of cDNA diluted by 100 times was subjected to a 20 µL Real-Time PCR reaction against the following sets of exon specific primers: [exon 2n_forward (5'→3') CTTGCTCATCAGTTGCCACTTC (SEQ ID NO: 13); exon 2n_reverse (5'→3') AAGTTTCCT-CACACGCAAAT-AG (SEQ ID NO: 14); exon 3n_forward (5'→3') GAAAGCACAGATGAATTGC (SEQ ID NO: 15); exon 3n_reverse (5'→3') TCATGTCACCATCATCTGT (SEQ ID NO: 16); exon 4n_forward (5'→3') CTAACTGGA-CACAGTGTGTTTG (SEQ ID NO: 17); exon 4n_reverse (5'→3') TCTGTGTGTAAGCAT-TTCTCTC (SEQ ID NO: 18); exon 5n_forward (5'→3') GCC-TTGTGAAAAAGGGTAAAG (SEQ ID NO: 19); exon 5n_reverse (5'→3') CCATGTTGCAGACTTTATGT (SEQ ID NO: 20)]. The PCR reactions were probed with SYBR Green (Takara, Japan) according to the following cycle conditions: 95° C. for 3 min followed by 40 cycles 5 sec at 95° C., and 30 sec at 60° C.

Figure 5A:
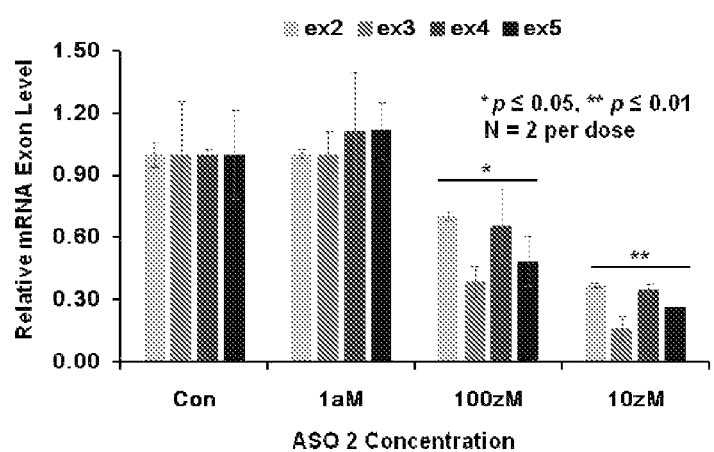
FIG. 5A. Nested qPCR by SYBR Green in HeLa cells treated with "ASO 2" at 0 (negative control), 10, 100 or 1,000 zM. (error bar by standard error)

[Changes in HIF-1α mRNA Exon Levels] The individual exon levels of ASO treated samples were normalized against each individual exon level without ASO treatment. The relative exon levels for each exon are provided in FIG. 5A. All the individual exon levels significantly decreased by 60 to 80% and 50 to 70% in the cells treated with "ASO 2" at 10 zM and 100 zM, respectively. However, the individual exon levels obtained with the cells treated with "ASO 2" at 1,000 zM (i.e., 1 aM) were not different from those with the cells without ASO treatment. It remains to be elucidated why the exon levels returned to the levels of negative control as the ASO concentration was increased to 1,000 zM. Nevertheless, the dose response pattern of the qPCR data is comparable to the dose response pattern of exon skipping in FIG. 3A of "Example 1".

Example 4. qPCR by TaqMan Probe for HIF-1α mRNA in HeLa Cells Treated with "ASO 2"

"ASO 2" was evaluated by nested qPCR for its ability to inhibit the expression of the full-length HIF-1α mRNA in HeLa cells as described in "Example 3" unless noted otherwise.

[cDNA Synthesis by One Step RT-PCR] 200 ng of RNA template subjected to a 25 µL reverse transcription reaction using Super Script® One-Step RT-PCR kit with Platinum® Taq polymerase (Cat. Number 10928-042, Invitrogen) against a set of exon-specific primers [exon 1_forward: (5'→3') CGCGAACGACAAGAAAAA (SEQ ID NO: 21); exon 8_reverse: (5'→3') CTGTGGTGAC-TTGTCCTTT (SEQ ID NO: 22)] according to the following cycle conditions: 50° C. for 30 min and 94° C. for 2 min, followed by 20 cycles of 30 sec at 94° C., 40 sec at 51° C., and 50 sec at 72° C.

[Nested qPCR] 1 µL of cDNA diluted by 100 times was subjected to a 20 µL Real-Time PCR reaction using a TaqMan probe (Hs00936371_m1, Thermo Fisher) designed to detect the junction of the human HIF-1α exon 1 and exon 2 according to the following cycle conditions: 95° C. for 3 min followed by 40 cycles 10 sec at 95° C., and 30 sec at 60° C.

Figure 5B:
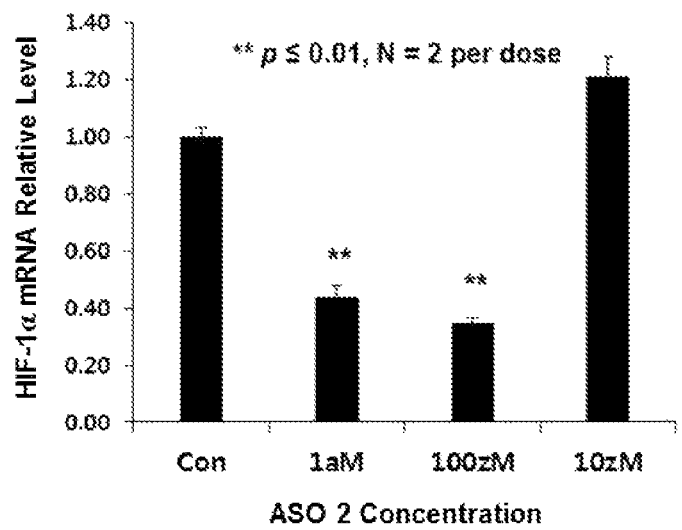
FIG. 5B. Nested qPCR by TaqMan probe in HeLa cells treated with "ASO 2" at 0 (negative control), 10, 100 or 1,000 zM. (error bar by standard error)

[Changes in Full-length HIF-1α mRNA Level] The full-length mRNA level of ASO treated samples were normalized against the mRNA level without ASO treatment. The observed relative mRNA levels are provided in FIG. 5B. The full-length HIF-1α mRNA level significantly decreased by 65% and 55% in the cells treated with "ASO 2" at 100 zM and 1,000 zM, respectively. However, the full-length mRNA level remained unchanged in the cells treated with "ASO 2" at 10 zM.

Example 5. Exon Skipping Induced by "ASO 6"

"ASO 6" specified in Table 1 is a 17-mer ASO complementarily binding to the 3' splice site of exon 2 in the human HIF-1α pre-mRNA with the complementary base pairings as marked "bold" and "underlined" in

[(5'→3') guuguuguuaaguag|
GAUAAGUUCUGAACG (SEQ ID NO: 5)].

"ASO 6" possesses a 7-mer complementary overlap with intron 1 and a 10-mer complementary overlap with exon 2.

"ASO 6" was evaluated by nested RT-PCR for its ability to induce the skipping of exon 2 of the human HIF-1α mRNA in HeLa cells according to the procedures described in "Example 1" unless noted otherwise.

Figure 6A:
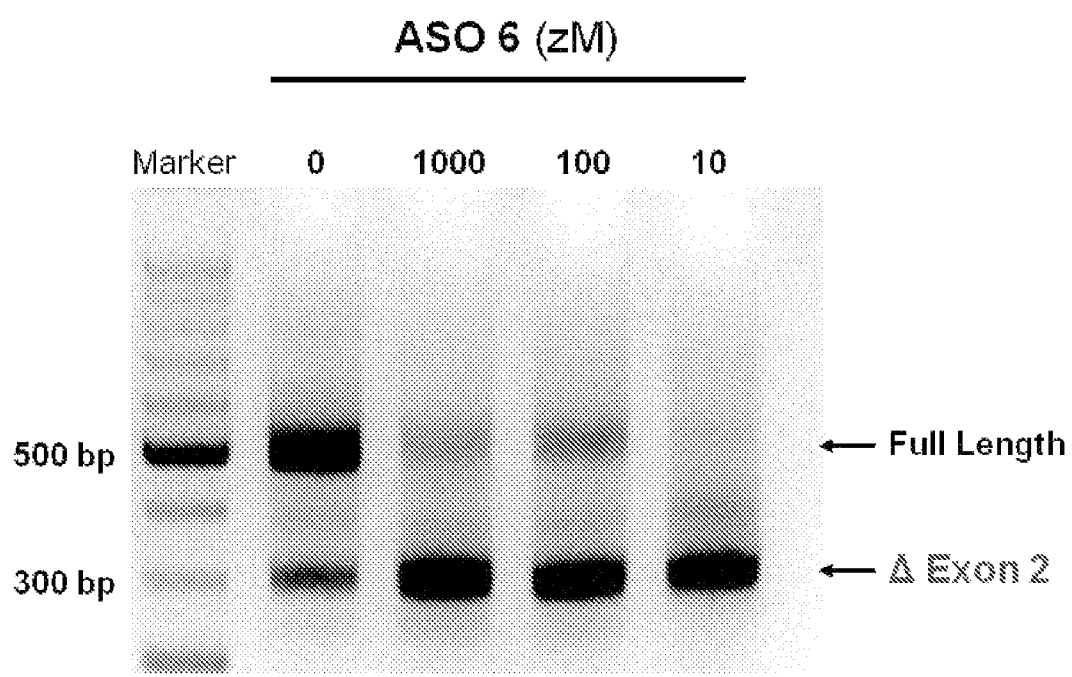
FIG. 6A. Electrophoresis data of HIF-1α nested RT-PCR products in HeLa cells treated with "ASO 6" at 0 (negative control), 10, 100 or 1,000 zM.

The PCR products were subjected to electrophoretic separation on a 2% agarose, and the electrophoresis results are provided in FIG. 6A. The skipping of exon 2 was robust at all the treatment concentrations of "ASO 6". "ASO 6" induced the skipping of exon 2 more effectively than "ASO 2". The PCR band for the full length HIF-1α mRNA disappeared almost completely at all the tested concentrations of "ASO 6". [cf. FIG. 6A] In the meantime, there was a significant level of the full length HIF-1α mRNA remaining in the RNA extracts of the cells treated with "ASO 2" at 10 to 1,000 zM. [cf. FIG. 3A]

Example 6. Inhibition of HIF-1α Protein Expression in HeLa Cells by "ASO 6"

"ASO 6" was evaluated for its ability to inhibit the expression of HIF-1α protein in HeLa cells according to the procedures described in "Example 2" unless noted otherwise.

Figure 6B:
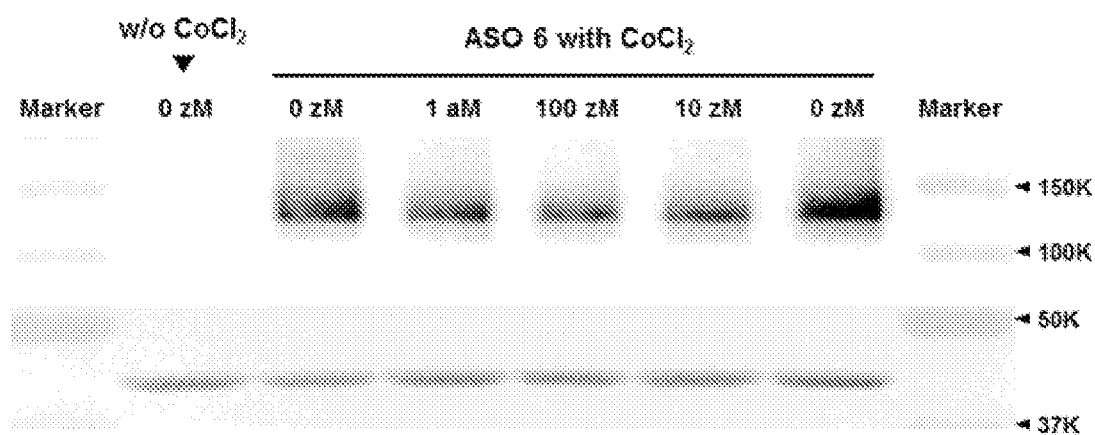
FIG. 6B. HIF-1α western blot data in HeLa Cells treated with "ASO 6" at 0 zM (negative control), 10 zM, 100 zM, or 1 aM for 24 hours.
Figure 6C:
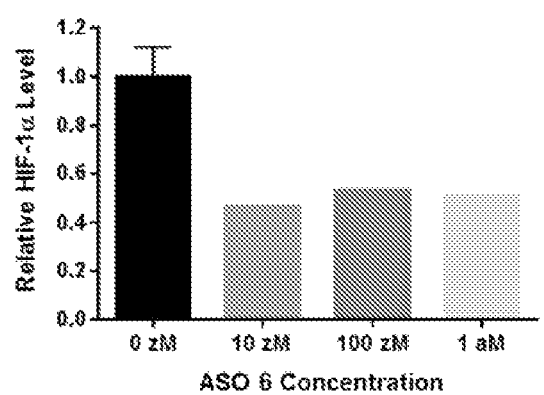
FIG. 6C. HIF-1α expression levels normalized against β-actin in HeLa cells treated with "ASO 6" at 0 zM (negative control), 10 zM, 100 zM, or 1 aM for 24 hours. (error bar by standard error)

FIG. 6B is a western blot data obtained with HeLa cells treated with "ASO 6" at 0 (negative control), 10, 100 or 1,000 zM. The expression of HIF-1α protein decreased by ca 45~55% at the treatment concentrations (FIG. 6C).

Example 7. qPCR by SYBR Green for HIF-1α mRNA in HeLa Cells Treated with "ASO 6"

"ASO 6" was evaluated for its ability to induce a change in HIF-1α mRNA in HeLa cells by nested qPCR according to the procedures in "Example 4" unless noted otherwise.

[cDNA Synthesis by One Step RT-PCR] 200 ng of RNA template subjected to a 25 μL reverse transcription reaction using Super Script® One-Step RT-PCR kit with Platinum® Taq polymerase (Cat. Number 10928-042, Invitrogen) against a set of exon-specific primers [exon 1_forward: (5'→3') CGCGAACGACAAGAAAAA (SEQ ID NO: 21); exon 8_reverse: (5'→3') CTGTGGTGAC-TTGTCCTTT (SEQ ID NO: 22)] according to the following cycle conditions: 50° C. for 30 min and 94° C. for 2 min, followed by 15 cycles of 30 sec at 94° C., 40 sec at 51° C., and 50 sec at 72° C.

[Changes in HIF-1α mRNA Exon Levels] The individual exon levels normalized against the individual exon levels without ASO treatment are provided in FIG. 7A. The exon levels significantly decreased by 35%, ca 30%, and ca 45% in the cells treated with "ASO 6" at 10, 100, and 1,000 zM, respectively.

Example 8. qPCR by TaqMan Probe for HIF-1α mRNA in HeLa Cells Treated with "ASO 6"

"ASO 6" was evaluated by nested qPCR for its ability to inhibit the expression of the full-length HIF-1α mRNA in HeLa cells as described in "Example 7" unless noted otherwise.

[Changes in Full-length HIF-1α mRNA Level] The full-length mRNA level of ASO treated samples were normalized against the mRNA level without ASO treatment. The observed relative mRNA levels are provided in FIG. 7B. The full-length HIF-1α mRNA level significantly decreased by ca 60% and 80% in the cells treated with "ASO 6" at 100 zM and 1,000 zM (1 aM), respectively. However, the full-length mRNA level remained unchanged in the cells treated with "ASO 6" at 10 zM.

Example 9. Inhibition of HIF-1α Protein Expression in HeLa Cells by "ASO 1"

"ASO 1" specified in Table 1 is a 14-mer ASO complementarily binding to the 3' splice site of exon 2 in the human HIF-1α pre-mRNA with the complementary base pairings as marked "bold" and "underlined" in

[(5'→3') guuguuguuaaguag|
GAUAAGUUCUGAACG (SEQ ID NO: 5)].

"ASO 1" possesses a 3-mer complementary overlap with intron 1 and an 11-mer complementary overlap with exon 2.

"ASO 1" was evaluated for its ability to down-regulate the HIF-1α expression in HeLa cells according to the procedures described in "Example 2" unless noted otherwise. In this example, HeLa cells were treated with "ASO 1" at 0 zM (negative control), 100 zM, 300 zM, 1 aM, 3 aM, 10 aM, 30 aM, 100 aM or 300 aM for 72 hours prior to inhibit the activity of PHDs by an incubation with 200 μM $CoCl_2$ for 3 hours. There were 4 culture dishes of the negative control, i.e., 0 zM "ASO 1".

Figure 8A:
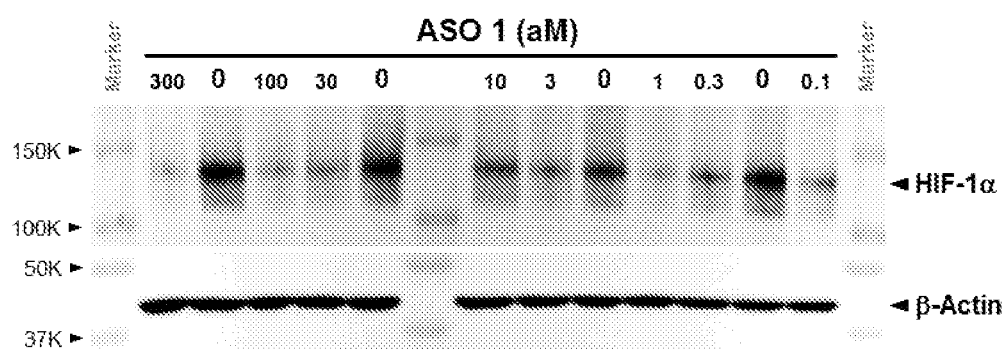
FIG. 8A. HIF-1α western blot data in HeLa cells treated with "ASO 1" at 0 zM (negative control), 100 zM, 300 zM, 1 aM, 3 aM, 10 aM, 30 aM, 100 aM or 300 aM for 72 hours.

FIG. 8A provides a HIF-1α western blot data obtained with the HeLa cell lysates. The HIF-1α protein level was considerably higher in the lysates of the negative control than all the lysates of the cells treated with "ASO 1".

Figure 8B:
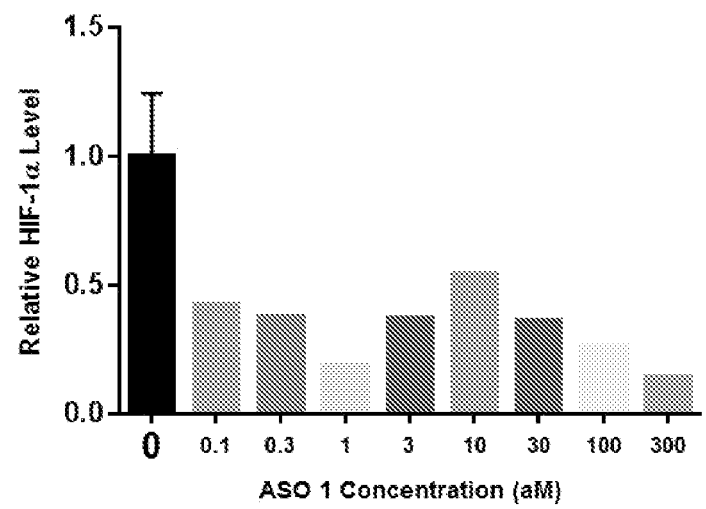
FIG. 8B. HIF-1α expression levels normalized against β-actin in HeLa cells treated with "ASO 1" at 0 zM (negative control), 100 zM, 300 zM, 1 aM, 3 aM, 10 aM, 30 aM, 100 aM or 300 aM for 72 hours. (N=4 only for the negative control; error bar by standard error)

FIG. 8B provides the individual HIF-1α band intensities against individual β-actin band intensity by densitometry. The HIF-1α expression in HeLa cells decreased by 40 to 80% by the 72 hour incubation with "ASO 1" at 0.1 to 300 aM.

Example 10. Inhibition of Tumor Growth of U-251 Xenograft in Nude Mice by "ASO 1"

"ASO 1" was evaluated for its ability to inhibit the tumor growth in nude mice with U-251 xenograft as described below.

[Induction of U-251 Xenograft] U-251 human glioblastoma cells were grown in DMEM supplemented with 10% FBS, 1% streptomycin-penicillin, 1% L-glutamine and 1% sodium pyruvate under 5% $CO_2$ at 37° C. In Day −14, 6 weeks old male nude mice (Charles River, Japan) were subcutaneously inoculated with $5 \times 10^5$ U-251 cells per animal in the right supra-scapular area. The animals were allowed free access to chow diet and tap water.

[Grouping & ASO Treatment] In Day 0, the animals were randomly assigned into 4 groups of negative control (no ASO treatment), 100 pmole/Kg "ASO 1", 1,000 pmole/Kg "ASO 1", and 3,000 pmole/Kg "ASO 1". 7 animals per group with an average tumor volume of 50 $mm^3$. The ASO treatment groups subcutaneously received "ASO 1" as dissolved in PBS at 5 mL/Kg 3× per week from Day 0 to Day 21.

Figure 9A:
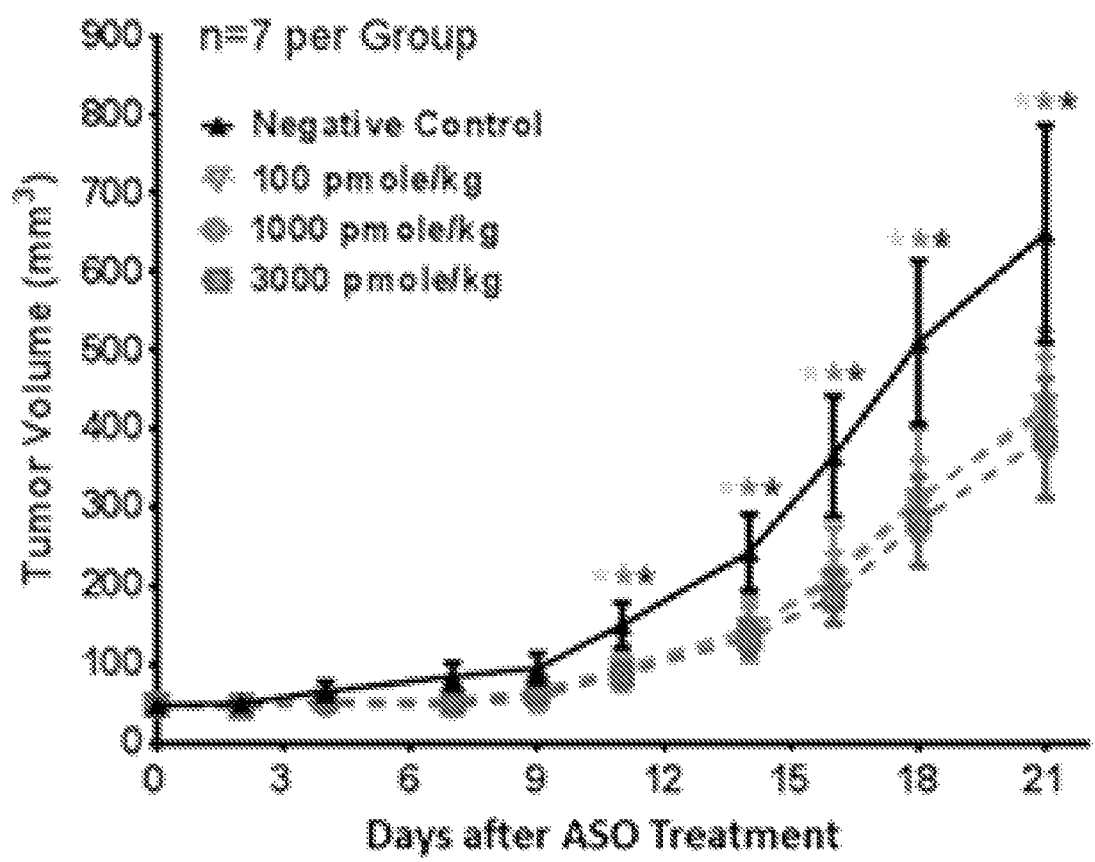
FIG. 9A. U251 tumor growth in nude mice subcutaneously receiving "ASO 1" at 0 (negative control), 100, 1,000 or 3,000 pmole/Kg. (error bar by standard error)

[Inhibition of Tumor Growth] The tumor volume was measured three times per week. The tumor growth was significantly inhibited in the ASO treatment groups by ca 35 to 45% in Day 21. [cf. FIG. 9A]

[HIF-1α IHC of Tumor Mass] In Day 22, the animals were sacrificed and the tumor mass was extracted for the evaluation of the HIF-1α protein expression in tumor mass by HIF-1α IHC (immunohistochemistry). Tissue samples for IHC were prepared by paraffin block. The tissues on slide were immunolabeled in series with a rabbit anti-human HIF-1α antibody (Cat. Number SC-10790, Santa Cruz) at 1:100 dilution, with an anti-rabbit IgG (Cat. Number BA-1100, Vector) at 1:200 dilution, and finally with Dylight 594-steptavidin (Cat. Number SA-5594, Vector) at 1:200 dilution. The HIF-1α IHC images were captured on an Olympus fluorescence microscope. The nuclei were stained with DAPI.

Figure 9B:
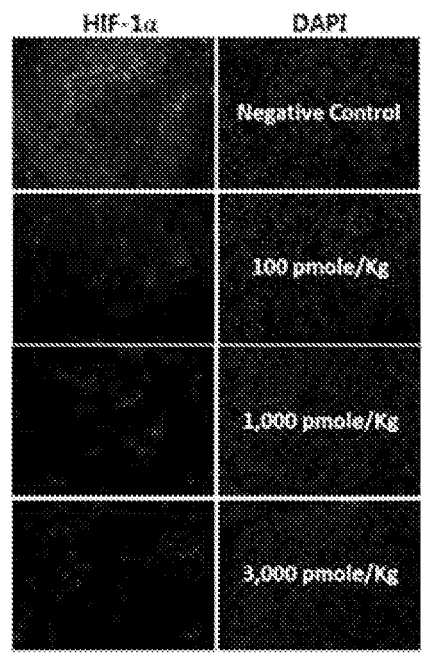
FIG. 9B. Representative intra-tumoral HIF-1α IHC images from each ASO dose group.
Figure 9C:
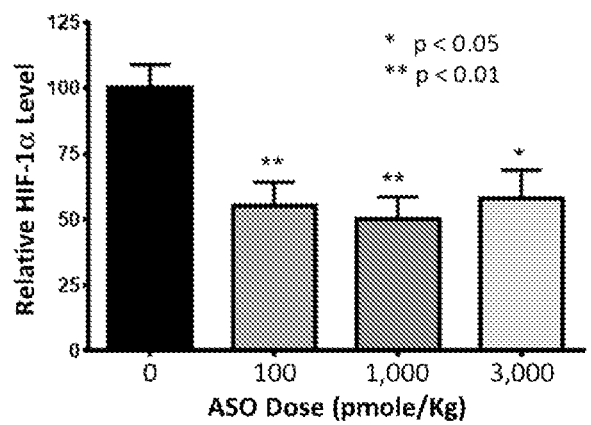
FIG. 9C. Average HIF-1α expression level of each dose group normalized against the negative control group. (N=5 per group; error bar by standard error)

FIG. 9B provides a representative set HIF-1α IHC images from each group. The HIF-1α expression in the negative control group was marked, whereas the expression in the treatment groups was minimal. Each IHC image was scored for HIF-1α expression by densitometry using ImageJ program. FIG. 9C provides the average HIF-1α expression level of each dose group normalized against the negative control group. (N=5 per group) The intra-tumoral HIF-1α expression significantly (by student's t-test) decreased by ca 40 to 50% in all the ASO treatment groups.

Example 11. Inhibition of Tumor Growth of A431 Xenograft in Nude Mice by "ASO 6"

"ASO 6" was evaluated for its ability to inhibit the tumor growth of A431 xenograft in nude mice as described below.

[Induction of A431 Xenograft] A431 human epidermoid carcinoma cells (Cat. Number CRL1555, ATCC) were grown in DMEM supplemented with 10% FBS, 1% streptomycin/penicillin, 1% L-glutamine and 1% sodium pyruvate under 5% $CO_2$ at 37° C. In Day −10, 6 weeks old male nude mice (Charles River, Japan) were subcutaneously inoculated with 5×10⁵ A431 cells per animal in the left leg. The animals were allowed free access to chow diet and tap water.

[Grouping & ASO Treatment] In Day 0, the animals were randomly assigned into 4 groups of negative control (no ASO treatment), 30 pmole/Kg "ASO 6", 100 pmole/Kg "ASO 6", and 300 pmole/Kg "ASO 6". 8 animals per group with an average tumor volume of 108 mm³. The ASO treatment groups subcutaneously received "ASO 6" dissolved in PBS at 2 mL/Kg 3× per week from Day 0 to Day 25.

Figure 10A:
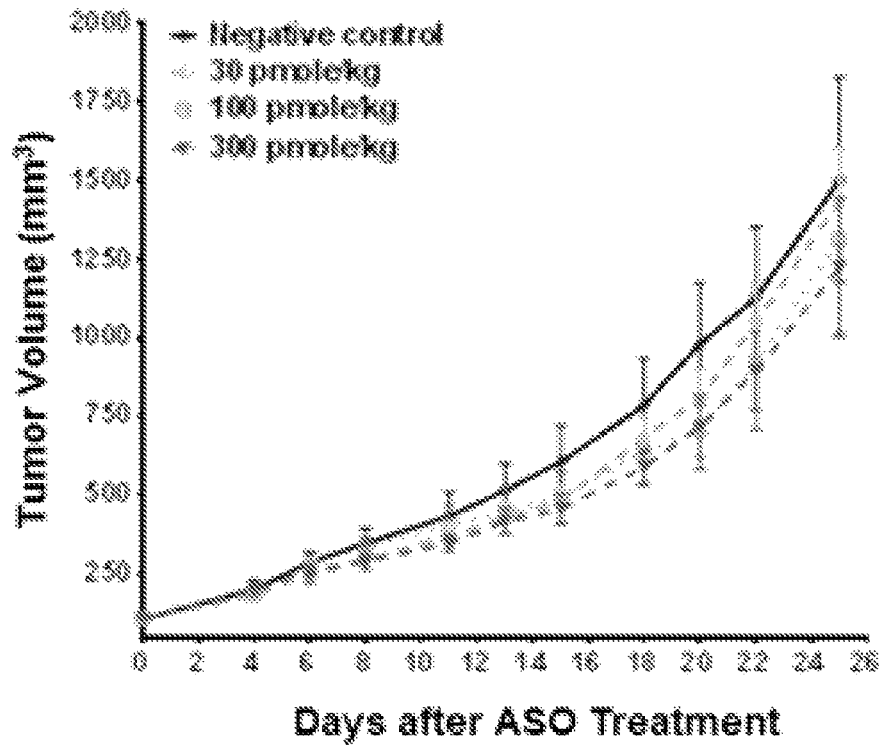
FIG. 10A. A431 tumor growth in nude mice subcutaneously treated with "ASO 6" at 0 (negative control), 30, 100 or 300 pmole/Kg, 3× per week.
Figure 10B:
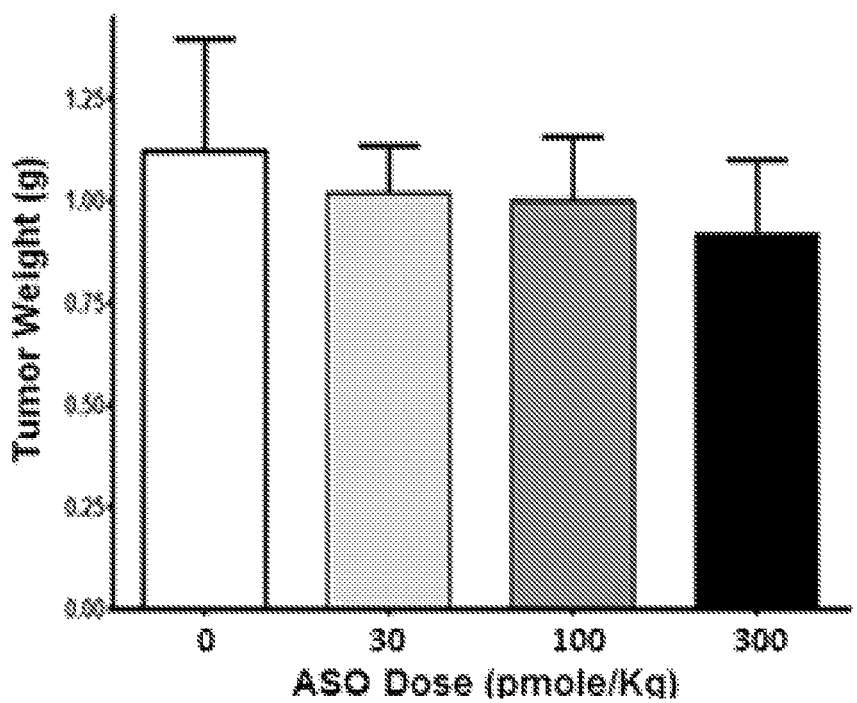
FIG. 10B. Average tumor weight in Day 25. (error bar by standard error)

[Inhibition of Tumor Growth] The tumor volume was measured three times per week. As "ASO 6" was repeatedly administered, the tumor growth was inhibited in a dose dependent manner although without statistical significance. [cf. FIG. 10A] The tumor growth was inhibited by ca 20% in the 300 pmole/Kg group. In Day 25 the animals were sacrificed for tumor extraction. The average tumor mass in Day 25 (at sacrifice) tended to decrease as the ASO dose was increased. [cf. FIG. 10B] The tumor mass decreased by ca 20% without significance in the 300 pmole/Kg ASO treatment group.

Example 12. Inhibition of Tumor Growth of PC3 Xenograft in Nude Mice by "ASO 6"

"ASO 6" was evaluated for its ability to inhibit the tumor growth of PC3 xenograft in nude mice as described below.

[Induction of PC3 Xenograft] PC3 human prostate carcinoma cells (Cat. Number CRL1435, ATCC) were grown in F-12K medium supplemented with 10% FBS, 1% streptomycin-penicillin, 1% L-glutamine and 1% sodium pyruvate under 5% $CO_2$ at 37° C. In Day −7, 6 weeks old male nude mice (Harlan Laboratories, Italy) were subcutaneously inoculated with 3×10⁶ PC3 cells per animal in the left leg. The animals were allowed free access to chow diet and tap water.

[Grouping & ASO Treatment] In Day 0, the animals were randomly assigned into 4 groups of negative control (no ASO treatment), 1 pmole/Kg "ASO 6", 10 pmole/Kg "ASO 6", and 100 pmole/Kg "ASO 6". 9 animals per group with an average tumor volume of ca 88 mm³. The treatment groups subcutaneously received "ASO 6" as dissolved in PBS at 2 mL/Kg 2× per week from Day 0 to Day 28.

Figure 10C:
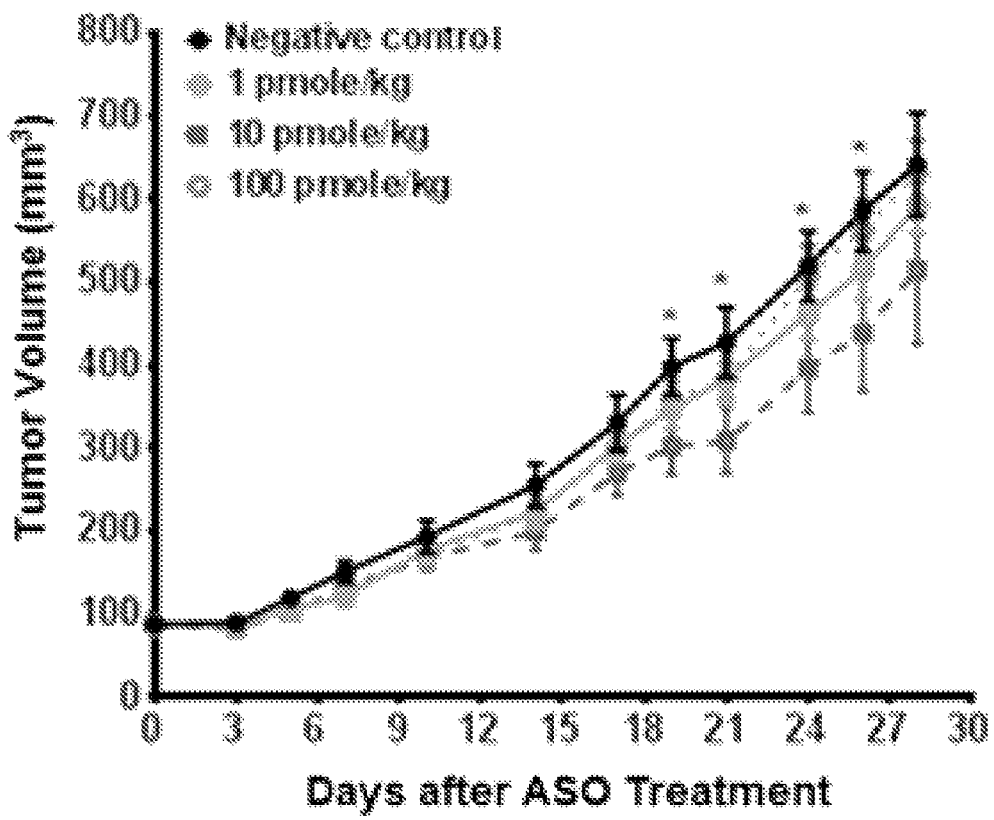
FIG. 10C. PC3 tumor growth in nude mice subcutaneously treated with "ASO 6" at 0 (negative control), 1, 10 or 100 pmole/Kg, 2× per week.
Figure 10D:
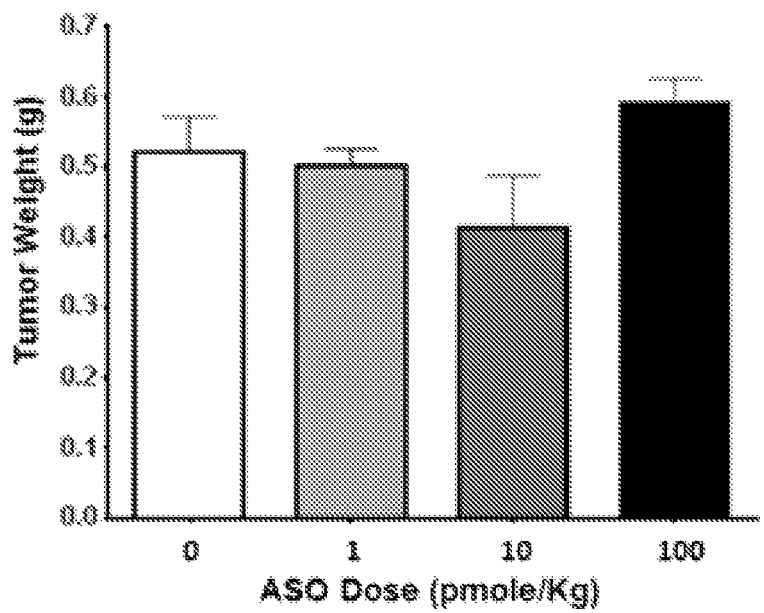
FIG. 10D. Average tumor weight in Day 28. (error bar by standard error)

[Inhibition of Tumor Growth] The tumor volume was measured three times per week. The tumor growth was significantly inhibited by ca 25~30% in the 10 pmole/Kg group during Days 19~26. [cf. FIG. 10C] In Day 28, the animals were sacrificed for tumor extraction. The average tumor mass of the 10 pmole/Kg group was smaller than the mass of the negative control group by 21% but without significance. [cf. FIG. 10D]

As the dose was increased from 10 to 100 pmole/Kg, the anti-tumor activity disappeared. Given that elevated HIF-1α expression was suggested to prolong lymphocyte survival in transgenic mice [*PLOS One* vol 8(4), e57833 (April 2013)], the observed decrease of the antitumor activity in the 100 pmole/Kg group would be due to a decrease of the innate immunity by knocking down HIF-1α activity too much in the high dose group.

Example 13. Inhibition of Tumor Growth of U-251 MG Xenograft in Nude Mice by "ASO 6" & "ASO 11"

Although "ASO 6" is fully complementary to the human HIF-1α pre-mRNA, it possesses a single mismatch with the mouse HIF-1α pre-mRNA exon 2. "ASO 11" is a 17-mer ASO designed to complementarily target the mouse pre-mRNA at the same region targeted by "ASO 6" the human HIF-1α pre-mRNA. "ASO 11" possesses a 7-mer and 10-mer complementary overlap with intron 1 and exon 2 in the mouse HIF-1α pre-mRNA, respectively.

"ASO 6" and "ASO 11" were combined by equivalent amount in order to evaluate the antitumor activity against U-251 MG xenograft in nude mice by inhibiting HIF-1α expression in the xenograft of human origin as well as in the mouse.

[Induction of U-251 MG Xenograft] U-251 MG human glioblastoma astrocytoma cells (Cat. Number 09063001, Sigma) were grown in MEM supplemented with 10% FBS, 1% streptomycin-penicillin, 1% L-glutamine and 1% sodium pyruvate under 5% $CO_2$ at 37° C. In Day −30, 5 weeks old male nude mice (Harlan Laboratories, Italy) were subcutaneously inoculated with 3×10⁶ U-251 MG cells formulated with Matrigel in the right supra-scapular area of each animal. The animals were allowed free access to chow diet and tap water.

[Grouping & ASO Treatment] In Day 0, the animals were randomly assigned into 4 groups of negative control (no ASO treatment), 0.1 pmole/Kg "ASO 6" plus 0.1 pmole/Kg "ASO 11", 1 pmole/Kg "ASO 6" plus 1 pmole/Kg "ASO 11", and 10 pmole/Kg "ASO 6" plus 1 pmole/Kg "ASO 11". 9 animals per group with an average tumor volume of ca 75 mm³. The treatment groups subcutaneously received "ASO 6" and "ASO 11" as dissolved in PBS at 2 mL/Kg 2× per week from Day 0 to Day 91.

[Terminal Sacrifice for Organ/Tissue Analysis] The animals were sacrificed in Day 92 to extract tissue samples including tumor, whole blood, the liver, lung, spleen, heart and kidneys. The tissue samples were subjected to IHC and biological analysis.

Figure 11A:
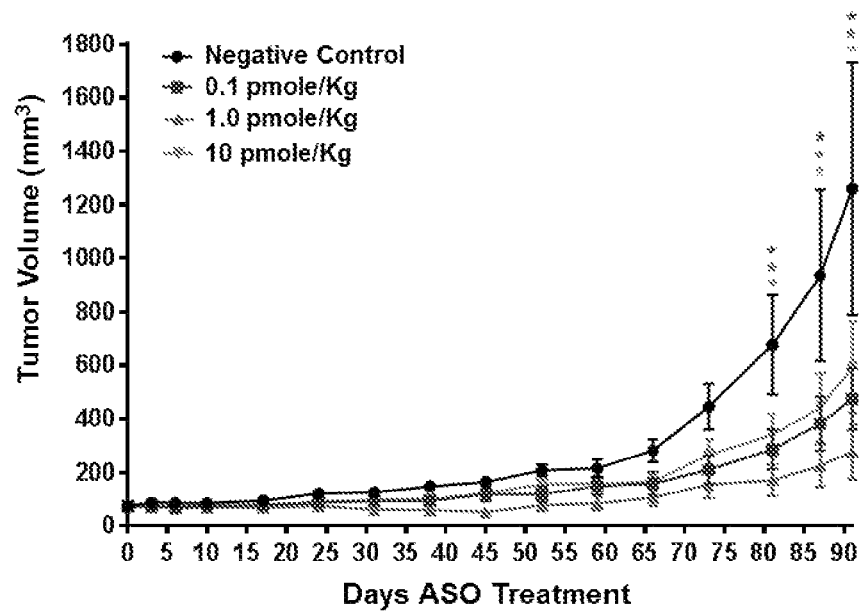
FIG. 11A. U-251 MG tumor growth in nude mice subcutaneously treated with "ASO 6" plus "ASO 11" by equivalent amount at 0 (negative control), 0.1, 1.0 or 10 pmole/Kg, 2× per week. (error bar by standard error)

[Inhibition of Tumor Growth] The tumor volume was measured 2× per week during the first two weeks post dose, and 1× per week afterwards. There was a clear and significant trend of tumor growth inhibition in the ASO treatment groups. However the 1.0 pmole/Kg treatment group showed the strongest inhibition of tumor growth. In Day 91, the tumor growth was significantly (by ANOVA) inhibited by 66%, 83% and 56% for the 0.1, 1.0 and 10 pmole/Kg ASO treatment group, respectively. [cf. FIG. 11A]

Figure 11B:
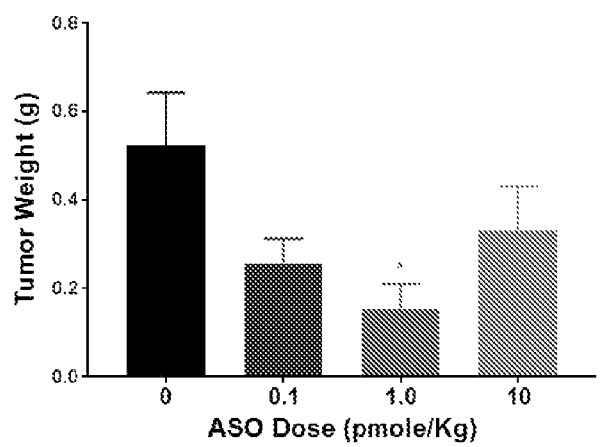
FIG. 11B. Average U-251 MG tumor weight in Day 92.

FIG. 11B provides the average tumor weight by group in Day 92. Although the tumor weight decreased by 47 to 71% in the ASO treatment groups, the 1.0 pmole/Kg dose group showed the largest decrease of 71%. The difference between the negative control and 1 pmole/Kg group was significant by student's t-test.

Given that elevated HIF-1α expression was suggested to prolong lymphocyte survival in transgenic mice [*PLOS One* vol 8(4), e57833 (April 2013)], the weaker antitumor activity in the 10 pmole/Kg group than in the 1.0 pmole/Kg group would possibly reflect a decrease of the innate immunity by knocking down HIF-1α activity too much in the 10 pmole/Kg group.

[Average Bodyweight & Organ Weight] Although there were no significant changes in the bodyweight, the 10 pmole/Kg group showed the smallest average bodyweight in Week 13, i.e., 39.6 g for the negative control group vs 38.0 g for the 10 pmole/Kg group.

The 10 pmole/Kg treatment group tended to show smaller weight of organs except for the spleen than the negative control group. The weights of the heart and kidney were significantly smaller in the 10 pmole/Kg group than the negative control group. (0.23±0.01) g vs (0.20±0.01) g for the heart and (0.60±0.02) g vs (0.56±0.02) g for the kidney.

The weight of the spleen was larger in the 10 pmole/Kg group than the negative control group. (0.27±0.03) g for the negative control group vs (0.33±0.13) g for the 10 pmole/Kg group.

Based on the above findings with the weights, the 10 pmole/Kg treatment is considered to have affected the growth or development of the animals than the treatment at lower doses or the negative control. Considering that HIF-1α induces the expression of VEGF and EPO (erythropoietin), it would not be surprising to imagine a marked increase of the spleen weight by chronic systemic inhibition of HIF-1α. Thus the HIF-1α expression could have been inhibited more in the 10 pmole/Kg group than in the 1.0 pmole/Kg group.

[Serum VEGF-A Level] The serum VEGF-A level was determined using a mouse VEGF-A ELISA kit (Cat. Number NMV00, R&D Systems, USA). Interestingly, the serum VEGF-A level tended to be higher in the ASO treatment groups, although without significance. The observed serum VEGF-A levels were (47.0±2.5) pg/mL, (48.7±3.1) pg/mL, (51.0±5.6) pg/mL, and (50.0±2.7) pg/mL for the negative control group, the 0.1 pmole/Kg, 1 pmole/Kg, and 10 pmole/Kg ASO treatment group, respectively. The observed serum VEGF-A levels would look contrary to usual predictions based on in vitro HIF-1α biology. In a controlled clinical study, however, a transient hypoxia induced a significant decrease in the serum VEGF-A level, suggesting the complexity of VEGF physiology. [*Am. J. Physiol. Endocrinol. Metab.* vol 290, E434-439 (2006)]

[HIF-1α IHC of Tumor Mass] Tumor samples of the negative control and 1.0 pmole/Kg treatment group were prepared by paraffin block for HIF-1α IHC. (N=4 per group) The tissues on slide were immunolabeled first with a rabbit anti-HIF-1α antibody (Cat. Number ab51608, Abcam) at 1:100 dilution, and then with an anti-rabbit IgG (Cat. Number A21207, Invitrogen) at 1:250 dilution. The HIF-1α IHC images were captured on a Zeiss slide scanner. The nuclei were stained with DAPI.

Figure 12A:
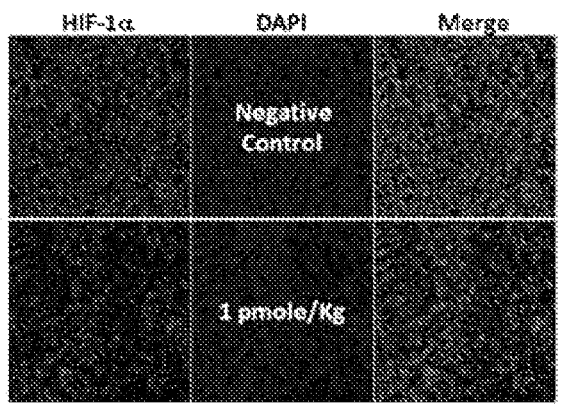
FIG. 12A. Representative intra-tumoral HIF-1α IHC images from the negative control and 1.0 pmole/Kg dose group.
Figure 12B:
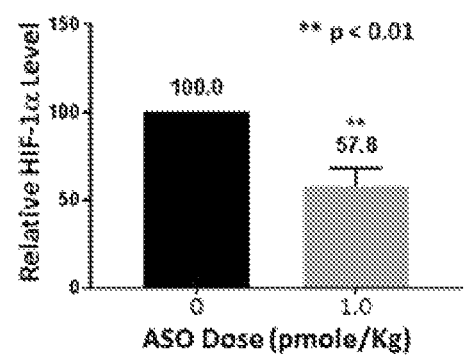
FIG. 12B. Average HIF-1α expression level of 1.0 pmole/Kg dose group normalized against the negative control group. (N=4 per group; error bar by standard error)

FIG. 12A provides a representative set HIF-1α IHC images from each group. Each IHC image was scored for HIF-1α expression by densitometry using ImageJ program. FIG. 12B provides the average HIF-1α expression level of the 1 pmole/Kg group normalized against the negative control group. (N=4 per group) The intra-tumoral HIF-1α expression significantly (by student's t-test) decreased by 42% in the 1.0 pmole/Kg ASO treatment group.

[VEGF-A IHC of Tumor Mass] Tumor samples of the negative control and 1.0 pmole/Kg treatment group were prepared by paraffin block for VEGF-A IHC. (N=4 per group) The tissues on slide were immunolabeled first with a rabbit anti-VEGF-A antibody (Cat. Number ab46154, Abcam) at 1:100 dilution, and then with an anti-rabbit IgG (Cat. Number A21207, Invitrogen) at 1:250 dilution. The VEGF-A IHC images were captured on a Zeiss slide scanner. The nuclei were stained with DAPI.

Figure 12C:
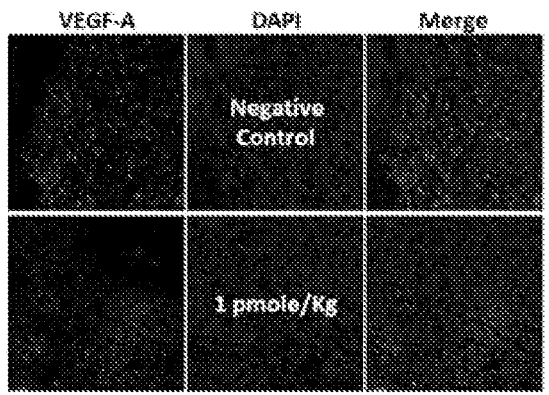
FIG. 12C. Representative intra-tumoral VEGF-A IHC images from the negative control and 1.0 pmole/Kg dose group.
Figure 12D:
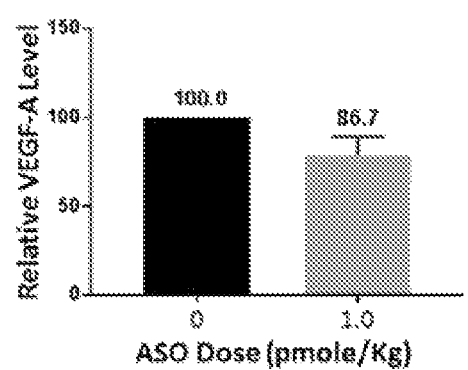
FIG. 12D. Average VEGF-A expression level of 1.0 pmole/Kg dose group normalized against the negative control group. (N=4 per group; error bar by standard error)
Figure 13:
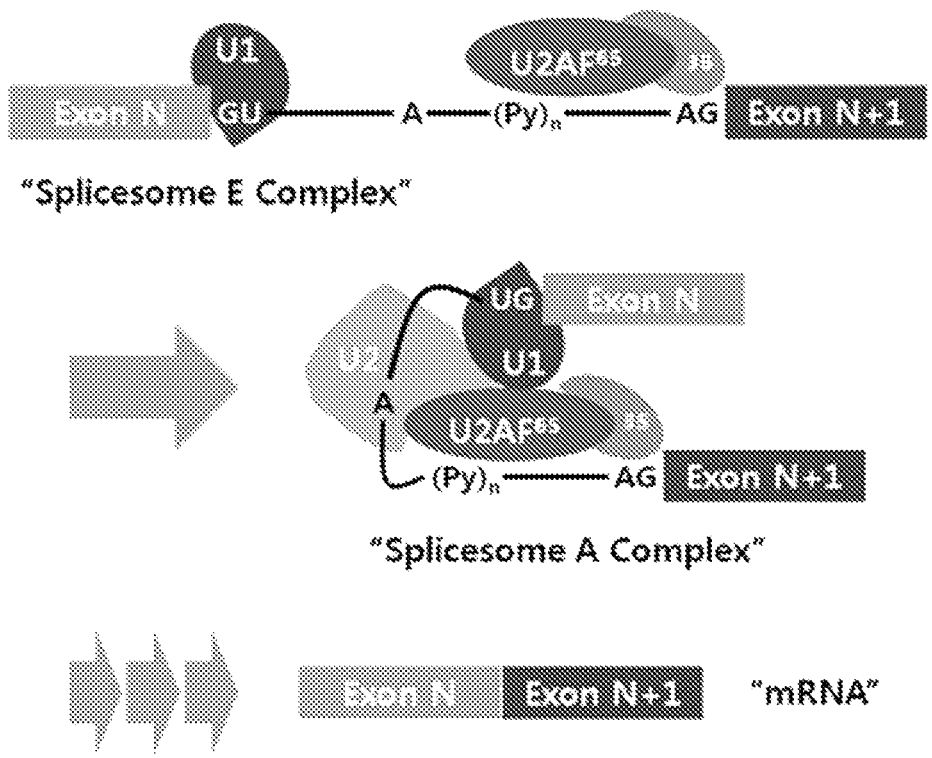
FIG. 13. Pre-mRNA is processed into mRNA following deletion of introns by a series of complex reactions collectively called "splicing".

FIG. 12C provides a representative set of VEGF-A IHC images from each group. Each IHC image was scored for VEGF-A expression by densitometry using ImageJ program. FIG. 12D provides the average VEGF-A level of the 1 pmole/Kg group normalized against the negative control group. The intra-tumoral VEGF-A expression marginally decreased by 13% in the 1.0 pmole/Kg ASO treatment group.

---

We claim:
1. A peptide nucleic acid derivative represented by Formula I, or a pharmaceutically acceptable salt thereof:

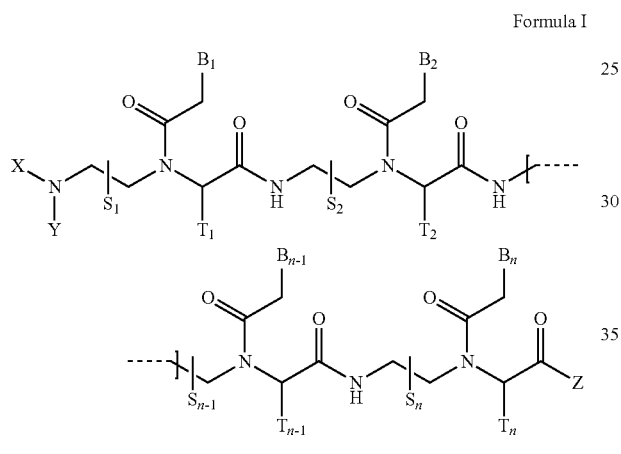

Formula I wherein, n is an integer between 10 and 26;

the compound of Formula I possesses at least a 10-mer complementary overlap with the 14-mer RNA sequence of [(5'→3') UAAGUAGGAUAAGU (SEQ ID NO: 2)] in the human HIF-1α pre-mRNA;

$S_1, S_2, \ldots, S_{n-1}, S_n, T_1, T_2, \ldots, T_{n-1}$, and $T_n$ independently represent deuterido, hydrido, substituted or non-substituted alkyl, or substituted or non-substituted aryl radical;

X and Y independently represent hydrido [H], formyl [H—C(=O)—], aminocarbonyl [NH$_2$—C(=O)—], substituted or non-substituted alkyl, substituted or non-substituted aryl, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylsulfonyl, or substituted or non-substituted arylsulfonyl radical;

Z represents hydroxy, substituted or non-substituted alkyloxy, substituted or non-substituted aryloxy, amino [—NH$_2$], substituted or non-substituted alkylamino, substituted or non-substituted arylamino, substituted or non-substituted alkyl, or substituted or non-substituted aryl radical;

$B_1, B_2, \ldots, B_{n-1}$, and $B_n$ are independently selected from natural nucleobases including adenine, thymine, guanine, cytosine and uracil, and unnatural nucleobases; and at least four of $B_1, B_2, \ldots, B_{n-1}$, and $B_n$ are independently selected from unnatural nucleobases with a substituted or non-substituted amino radical covalently linked to the nucleobase moiety.

2. The peptide nucleic acid derivative according to claim 1, or a pharmaceutical salt thereof:

wherein, n is an integer between 10 and 26;

the compound of Formula I possesses at least a 10-mer complementary overlap with the 14-mer RNA sequence of [(5'→3') UAAGUAGGAUAAGU (SEQ ID NO: 2)] in the human HIF-1α pre-mRNA;

$S_1, S_2, \ldots, S_{n-1}, S_n, T_1, T_2, \ldots, T_{n-1}$, and $T_n$ independently represent deuterido, hydrido, substituted or non-substituted alkyl, or substituted or non-substituted aryl radical;

X and Y independently represent hydrido, formyl, aminocarbonyl, substituted or non-substituted alkyl, substituted or non-substituted aryl, substituted or non-substituted alkylacyl, substituted or non-substituted arylacyl, substituted or non-substituted alkyloxycarbonyl, substituted or non-substituted aryloxycarbonyl, substituted or non-substituted alkylaminocarbonyl, substituted or non-substituted arylaminocarbonyl, substituted or non-substituted alkylsulfonyl, or substituted or non-substituted arylsulfonyl radical;

Z represents hydroxy, substituted or non-substituted alkyloxy, substituted or non-substituted aryloxy, amino [—NH$_2$], substituted or non-substituted alkylamino, substituted or non-substituted arylamino, substituted or non-substituted alkyl, or substituted or non-substituted aryl radical;

$B_1, B_2, \ldots, B_{n-1}$, and $B_n$ are independently selected from natural nucleobases including adenine, thymine, guanine, cytosine and uracil, and unnatural nucleobases; and, at least three of $B_1, B_2, \ldots, B_{n-1}$, and $B_n$ are independently selected from unnatural nucleobases represented by Formula II, Formula III, or Formula IV:

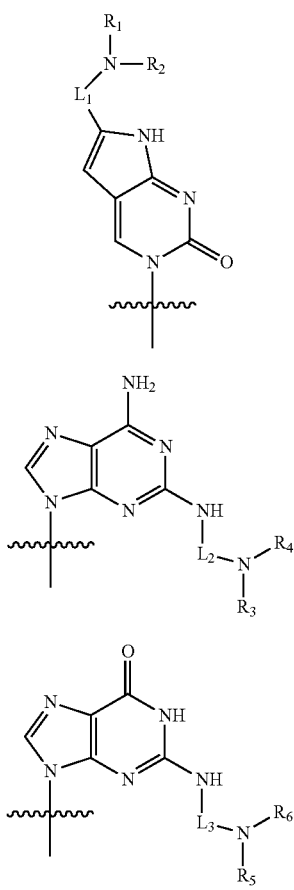

Formula II

Formula III

Formula IV wherein, $R_1, R_2, R_3, R_4, R_5$ and $R_6$ are independently selected from substituted or non-substituted alkyl, hydrido, hydroxy, and substituted or non-substituted alkyloxy radical; and, $L_1, L_2$ and $L_3$ are a covalent linker represented by Formula V connecting a basic amino group to the moiety responsible for nucleobase pairing properties:

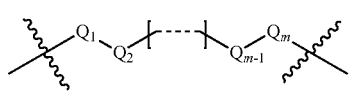

Formula V wherein, $Q_1$ and $Q_m$ are substituted or non-substituted methylene (—$CH_2$—) radical, and $Q_m$ is directly linked to the basic amino group;

$Q_2, Q_3, \ldots,$ and $Q_{m-1}$ are independently selected from substituted or non-substituted methylene, oxygen (—O—), sulfur (—S—), and substituted or non-substituted amino radical [—N(H)—, or —N(substituent)-]; and, m is an integer between 1 and 16.

3. The peptide nucleic acid derivative according to claim 1, or a pharmaceutical salt thereof:

wherein, n is an integer between 11 and 23;

the compound of Formula I possesses at least a 10-mer complementary overlap with the 14-mer RNA sequence of [(5'→3') UAAGUAGGAUAAGU (SEQ ID NO: 2)] in the human HIF-1α pre-mRNA;

$S_1, S_2, \ldots, S_{n-1}, S_n, T_1, T_2, \ldots, T_{n-1},$ and $T_n$ independently represent hydrido radical;

X and Y independently represent hydrido, substituted or non-substituted alkyl, substituted or non-substituted aryl, substituted or non-substituted alkylacyl, substituted or non-substituted arylacyl, substituted or non-substituted alkyloxycarbonyl, substituted or non-substituted alkylaminocarbonyl, substituted or non-substituted arylaminocarbonyl, substituted or non-substituted alkylsulfonyl, or substituted or non-substituted arylsulfonyl radical;

Z represents amino, or substituted or non-substituted alkylamino radical;

$B_1, B_2, \ldots, B_{n-1},$ and $B_n$ are independently selected from natural nucleobases including adenine, thymine, guanine, cytosine and uracil, and unnatural nucleobases; and, at least four of $B_1, B_2, \ldots, B_{n-1},$ and $B_n$ are independently selected from unnatural nucleobases represented by Formula II, Formula III, or Formula IV;

$R_1, R_2, R_3, R_4, R_5$ and $R_6$ are independently selected from substituted or non-substituted alkyl, and hydrido radical;

$Q_1$ and $Q_m$ are substituted or non-substituted methylene radical, and $Q_m$ is directly linked to the basic amino group;

$Q_2, Q_3, \ldots,$ and $Q_{m-1}$ are independently selected from substituted or non-substituted methylene, oxygen (—O—), and amino radical [—N(H)—]; and m is an integer between 1 and 11.

4. The peptide nucleic acid derivative according to claim 1, or a pharmaceutical salt thereof:

wherein, n is an integer between 11 and 21;

the compound of Formula I possesses at least a 10-mer complementary overlap with the 14-mer RNA sequence of [(5'→3') UAAGUAGGAUAAGU (SEQ ID NO: 2)] in the human HIF-1α pre-mRNA;

$S_1, S_2, \ldots, S_{n-1}, S_n, T_1, T_2, \ldots, T_{n-1},$ and $T_n$ independently represent hydrido radical;

X and Y independently represent hydrido, substituted or non-substituted alkyl, substituted or non-substituted aryl, substituted or non-substituted alkylacyl, substituted or non-substituted arylacyl, or substituted or non-substituted alkyloxycarbonyl radical;

Z represents amino, or substituted or non-substituted alkylamino radical;

$B_1, B_2, \ldots, B_{n-1},$ and $B_n$ are independently selected from natural nucleobases including adenine, thymine, guanine, cytosine, and unnatural nucleobases; and at least four of $B_1, B_2, \ldots, B_{n-1},$ and $B_n$ are independently selected from unnatural nucleobases represented by Formula II, Formula III, or Formula IV;

$R_1, R_2, R_3, R_4, R_5$ and $R_6$ are independently selected from substituted or non-substituted alkyl, and hydrido radical;

$Q_1$ and $Q_m$ are methylene radical, and $Q_m$ is directly linked to the basic amino group;

$Q_2, Q_3, \ldots,$ and $Q_{m-1}$ are independently selected from substituted or non-substituted methylene, and oxygen radical; and m is an integer between 1 and 9.

5. The peptide nucleic acid derivative according to claim 1, or a pharmaceutical salt thereof:
wherein,
n is an integer between 12 and 19;
the compound of Formula I possesses at least a 10-mer complementary overlap with the 14-mer RNA sequence of [(5'→3') UAAGUAGGAUAAGU (SEQ ID NO: 2)] in the human HIF-1α pre-mRNA;
$S_1, S_2, \ldots, S_{n-1}, S_n, T_1, T_2, \ldots, T_{n-1}$, and $T_n$ independently represent hydrido radical;
X and Y independently represent hydrido, substituted or non-substituted alkylacyl, substituted or non-substituted arylacyl, or substituted or non-substituted alkyloxycarbonyl radical;
Z represents amino, or substituted or non-substituted alkylamino radical;
$B_1, B_2, \ldots, B_{n-1}$, and $B_n$ are independently selected from natural nucleobases including adenine, thymine, guanine and cytosine, and unnatural nucleobases; and,
at least four of $B_1, B_2, \ldots, B_{n-1}$, and $B_n$ are independently selected from unnatural nucleobases represented by Formula II, Formula III, or Formula IV;
$R_1, R_2, R_3, R_4, R_5$ and $R_6$ are independently selected from substituted or non-substituted alkyl, and hydrido radical;
$Q_1$ and $Q_m$ are methylene radical, and $Q_m$ is directly linked to the basic amino group;
$Q_2, Q_3$, and $Q_{m-1}$ are independently selected from methylene, and oxygen radical; and
m is an integer between 1 and 9.

6. The peptide nucleic acid derivative according to claim 1, or a pharmaceutical salt thereof:
wherein,
n is an integer between 12 and 19;
the compound of Formula I possesses at least a 11-mer complementary overlap with the 14-mer RNA sequence of [(5'→3') UAAGUAGGAUAAGU (SEQ ID NO: 2)] in the human HIF-1α pre-mRNA;
$S_1, S_2, \ldots, S_{n-1}, S_n, T_1, T_2, \ldots, T_{n-1}$, and $T_n$ independently represent hydrido radical;
X and Y independently represent hydrido, substituted or non-substituted alkylacyl, substituted or non-substituted arylacyl, or substituted or non-substituted alkyloxycarbonyl radical;
Z represents amino, or substituted or non-substituted alkylamino radical;
$B_1, B_2, \ldots, B_{n-1}$, and $B_n$ are independently selected from natural nucleobases including adenine, thymine, guanine and cytosine, and unnatural nucleobases; and,
at least four of $B_1, B_2, \ldots, B_{n-1}$, and $B_n$ are independently selected from unnatural nucleobases represented by Formula II, Formula III, or Formula IV;
$R_1, R_2, R_3, R_4, R_5$ and $R_6$ are hydrido radical;
$Q_1$ and $Q_m$ are methylene radical, and $Q_m$ is directly linked to the basic amino group;
$Q_2, Q_3, \ldots$, and $Q_{m-1}$ are independently selected from methylene, and oxygen radical; and
m is an integer between 1 and 8.

7. The peptide nucleic acid derivative according to claim 1, or a pharmaceutical salt thereof:
wherein,
n is an integer between 12 and 19;
the compound of Formula I possesses at least a 12-mer complementary overlap with the 14-mer RNA sequence of [(5'→3') UAAGUAGGAUAAGU (SEQ ID NO: 2)] in the human HIF-1α pre-mRNA;
$S_1, S_2, \ldots, S_{n-1}, S_n, T_1, T_2, \ldots, T_{n-1}$, and $T_n$ independently represent hydrido radical;
X is hydrido radical;
Y represents substituted or non-substituted alkylacyl, substituted or non-substituted arylacyl, or substituted or non-substituted alkyloxycarbonyl radical;
Z represents amino, or substituted or non-substituted alkylamino radical;
$B_1, B_2, \ldots, B_{n-1}$, and $B_n$ are independently selected from natural nucleobases including adenine, thymine, guanine and cytosine, and unnatural nucleobases;
at least four of $B_1, B_2, \ldots, B_{n-1}$, and $B_n$ are independently selected from unnatural nucleobases represented by Formula II, Formula III, or Formula IV;
$R_1, R_2, R_3, R_4, R_5$ and $R_6$ are hydrido radical;
$L_1$ represents —(CH$_2$)$_2$—O—(CH$_2$)$_2$—, —CH$_2$—O—(CH$_2$)$_2$—, —CH$_2$—O—(CH$_2$)$_3$—, —CH$_2$—O—(CH$_2$)$_4$—, —CH$_2$—O—(CH$_2$)$_5$—, —CH$_2$—O—(CH$_2$)$_6$—, or —CH$_2$—O—(CH$_2$)$_7$— with the right end is directly linked to the basic amino group; and
$L_2$ and $L_3$ are independently selected from —(CH$_2$)$_2$—O—(CH$_2$)$_2$—, —(CH$_2$)$_3$—O—(CH$_2$)$_2$—, —(CH$_2$)$_2$—O—(CH$_2$)$_3$—, —(CH$_2$)$_2$—, —(CH$_2$)$_3$—, —(CH$_2$)$_4$—, —(CH$_2$)$_5$—, —(CH$_2$)$_6$—, —(CH$_2$)$_7$—, and —(CH$_2$)$_8$— with the right end is directly linked to the basic amino group.

8. The peptide nucleic acid derivative according to claim 1, or a pharmaceutical salt thereof, wherein the compound of Formula I is fully complementary to the target HIF-1α pre-mRNA sequence, or partially complementary to the target HIF-1α pre-mRNA sequence with one or two mismatches.

9. The peptide nucleic acid derivative according to claim 1, which is selected from the group of peptide nucleic acid derivatives provided below, or a pharmaceutically acceptable salt thereof:

(N→C) Fethoc-CA(5)G-AA(5)C-TTA(5)-TCC(102)-TA(5)-NH$_2$;

(N→C) Fmoc-CA(5)G-AA(5)C-TTA(5)-TCC(102)-TA(5)-NH$_2$;

(N→C) H-CA(5)G-AA(5)C-TTA(5)-T CC(103)-TA(5)-NH$_2$;

(N→C) Ac-CA(5)G-AA(5)C-TTA(5)-TCC(102)-TA(5)-NH$_2$;

(N→C) Piv-CA(5)G-AA(5)C-TTA(5)-TCC(102)-TA(5)-NH$_2$;

(N→C) Benzoyl-CA(5)G(203)-AA(5)C-TTA(4)-TCC(102)-TA(5)-NH$_2$;

(N→C) n-Propyl-CA(5)G-AA(5)C-TTA(5)-TCC(202)-TA(5)-NH$_2$;

(N→C) Benzyl-CA(5)G-AA(5)C-TTA(5)-TCC(102)-TA(5)-NH$_2$;

(N→C) p-Toluenesulfonyl-CA(5)G-AA(5)C-TTA(202)-TCC(102)-TA(5)-NH$_2$;

(N→C) N-(2-Phenylethyl)aminolcarbonyl-CA(5)G(3)-AA(5)C-TTA(3)-TCC(102)-TA(5)-NH$_2$;

(N→C) Fethoc-Lys-Leu-CA(5)G(202)-AA(5)C-TTA(8)-TCC(102)-TA(5)-Lys-NH$_2$;

(N→C) N-Ph-N-Me-CA(5)G-AA(5)C-TTA(5)-TCC(102)-TA(5)-Lys-NH$_2$;

(N→C) Piv-HEX-CA(5)G-AA(5)C-TTA(5)-TCC(102)-TA(5)-Lys-NH$_2$;

-continued (N→C) FAM-HEX-CA(5)G-AA(5)C-TTA(5)-TCC(102)-TA(5)-Lys-NH₂;

(N→C) Fethoc-GA(5)A-C(102)TT-A(5)TC-CTA(5)-C(102)T-NH₂;

(N→C) Fethoc-G(5)AA(5)-CTT-A(5)TC-CTA(5)-C(102)T-NH₂;

(N→C) Fethoc-GA(5)A-C(102)TT-A(5)TC-CTA(5)-CT-NH₂;

(N→C) Fethoc-G(5)AA(6)-CTT-A(6)TC-CTA(6)-C(102)T-NH₂;

(N→C) Fethoc-GA(202)A-C(105)TT-A(3)TC-CTA(5)-C(103)T-NH₂;

(N→C) Benzoyl-Gly-GA(5)A-C(102)TT-A(5)TC-CTA(5)-C(102)T-NH₂;

(N→C) Fethoc-Arg-GA(5)A-C(102)TT-A(5)TC-CTA(5)-C(102)T-Gly-NH₂;

(N→C) Fethoc-Val-GA(5)A-CTT-A(6)TC-CTA(5)-C(202)T-Gly-Lys-NH₂;

(N→C) Fethoc-A(6)GA-A(6)CT-TA(6)T-CC(102)T-A(6)CT-TA(6)-NH₂;

(N→C) Fethoc-A(5)GA-AC(102)T-TG(6)T-CC(102)T-A(6)CT-TA(6)-NH₂;

(N→C) Fethoc-A(6)GA-A(6)CT-TA(6)T-CC(102)T-A(6)CT-CA-NH₂;

(N→C) Fethoc-A(6)GA-A(6)CT-TA(6)T-CC(102)T-A(6)CT-AT-NH₂;

(N→C) Piv-Lys-AA(6)C-TTA(6)-TCC(102)-TA(6)C-TTA(5)-Val-NH₂;

(N→C) Fethoc-A(6)GA-A(6)CT-CA(6)T-CC(102)T-A(6)CT-TA(6)-NH₂;

(N→C) Fethoc-C(105)TT-A(6)TC-CTA(6)-C(102)TT-AA(6)C-NH₂;

(N→C) Fethoc-CTC(102)-A(6)TC-CTA(6)-C(102)TT-AA(6)C-NH₂;

(N→C) Fmoc-Val-CTC(102)-A(5)TC-CTA(6)-C(103)TT-AA(202)C-NH₂;

(N→C) Piv-A(6)TC-CTA(6)-C(102)TT-A(5)AC-NH₂;

(N→C) Fethoc-TTC(105)-AG(5)A-A(4)CT-TA(5)T-CC(202)T-A(6)CT-TA(6)A-C-NH₂;

(N→C) Fethoc-G-TTC(105)-AG(5)A-A(4)CT-TA(5)T-CC(102)T-AC(105)T-TA(6)A-C-NH₂;
and (N→C) Fethoc-TTC(105)-AG(5)A-A(4)CT-TA(5)T-CCT-AC(105)T-TAA-CA(202)A-NH₂:

wherein,
A, G, T, and C are PNA monomers with a natural nucleobase of adenine, guanine, thymine, and cytosine, respectively;

C(pOq), A(p), A(pOq), G(p), and G(pOq) are PNA monomers with an unnatural nucleobase represented by Formula VI, Formula VII, Formula VIII, Formula IX, and Formula X, respectively;

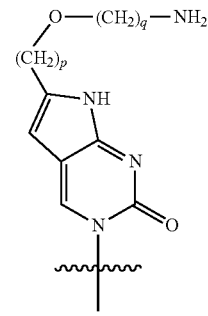

Formula VI

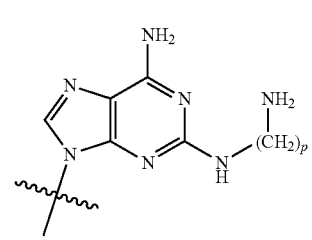

Formula VII

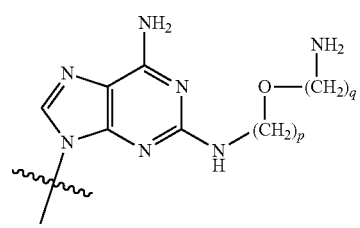

Formula VIII

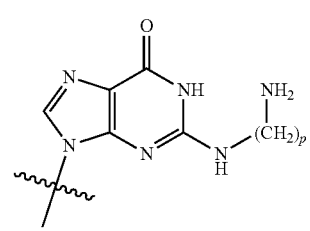

Formula IX

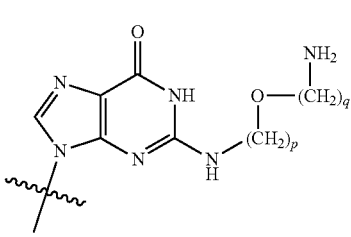

Formula X wherein
p and q are integers; and
the abbreviations for the N- and C-terminus substituents are as specifically described as follows: "Fmoc-" is the abbreviation for "[(9-fluorenyl)methyloxy]carbonyl-"; "Fethoc-" for "[2-(9-fluorenyl)ethyl-1-oxy]carbonyl"; "Ac-" for "acetyl-"; "Benzoyl-" for "benzenecabonyl-"; "Piv-" for "Pivaloyl-"; "n-Propyl-" for "1-(n-propyl)-"; "H-" for "hydrido-" group; "p-Toluenesulfonyl" for "(4-methylbenzene)-1-sulfonyl-"; "-Lys-" for amino acid residue "lysine"; "—Val-" for amino acid residue "valine"; "-Leu-" for amino acid residue "leucine"; "-Arg-" for amino acid residue "arginine"; "-Gly-" for amino acid residue "glycine"; "[N-(2-Phenylethyl)amino]carbonyl-" for "[N-1-(2-phenylethyl)amino]carbonyl-"; "Benzyl-" for "1-(phenyl)methyl-";

"Phenyl-" for "phenyl-"; "Me-" for "methyl-"; "—HEX-" for "6-amino-1-hexanoyl-", "FAM-" for "5, or 6-fluorescein-carbonyl-(isomeric mixture)", and "—NH$_2$" for non-substituted "-amino" group.

10. The peptide nucleic acid derivative according to claim 1, which is selected from the group of compounds provided below, or a pharmaceutically acceptable salt thereof:

(N→C) Fethoc-CA(5)G-AA(5)C-TTA(5)-TCC(102)-TA(5)-NH$_2$;

(N→C) Fethoc-GA(5)A-C(102)TT-A(5)TC-CTA(5)-C(102)T-NH$_2$;

(N→C) Fethoc-G(5)AA(5)-CTT-A(5)TC-CTA(5)-C(102)T-NH$_2$;

(N→C) Fethoc-GA(5)A-C(102)TT-A(5)TC-CTA(5)-CT-NH$_2$;

(N→C) Fethoc-G(5)AA(6)-CTT-A(6)TC-CTA(6)-C(102)T-NH$_2$;

(N→C) Fethoc-A(6)GA-A(6)CT-TA(6)T-CC(102)T-A(6)CT-TA(6)-NH$_2$;

(N→C) Fethoc-C(105)TT-A(6)TC-CTA(6)-C(102)TT-AA(6)C-NH$_2$;

(N→C) Fethoc-CTC(102)-A(6)TC-CTA(6)-C(102)TT-AA(6)C-NH$_2$;

(N→C) Piv-Lys-AA(6)C-TTA(6)-TCC(102)-TA(6)C-TTA(5)-Val-NH$_2$;

(N→C) Benzoyl-CA(5)G(203)-AA(5)C-TTA(4)-TCC(102)-TA(5)-NH$_2$; and (N→C) p-Toluenesulfonyl-CA(5)G-AA(5)C-TTA(202)-TCC(102)-TA(5)-NH$_2$.

11. A peptide nucleic acid derivative represented by Formula I, or a pharmaceutically acceptable salt thereof:
wherein,
the compound of Formula I possesses at least a 10-mer complementary overlap with a 20-mer RNA sequence [(5'→3') UGUUAAGUAGGAUAAGUUCU (SEQ ID NO: 1)], a part of the human HIF-1α pre-mRNA;
n is an integer between 10 and 26;
$S_1, S_2, \ldots, S_{n-1}, S_n, T_1, T_2, \ldots, T_{n-1}$, and $T_n$ independently represent hydrido, substituted or non-substituted alkyl, or substituted or non-substituted aryl radical;
X and Y independently represent hydrido, substituted or non-substituted alkyl, substituted or non-substituted acyl, substituted or non-substituted sulfonyl, or substituted or non-substituted aryl radical;
Z represents hydrido, hydroxy, substituted or non-substituted alkyloxy, substituted or non-substituted aryloxy, substituted or non-substituted amino radical;
$B_1, B_2, \ldots, B_{n-1}$, and $B_n$ are independently selected from natural nucleobases including adenine, thymine, guanine, cytosine and uracil, and unnatural nucleobases; and,
at least three of $B_1, B_2, \ldots, B_{n-1}$, and $B_n$ are independently selected from unnatural nucleobases with a substituted or non-substituted amino radical covalently linked to the moiety responsible for its due nucleobase pairing properties.

12. The peptide nucleic acid derivative according to claim 11, or a pharmaceutical salt thereof:
wherein,
n is an integer between 10 and 26;
$S_1, S_2, \ldots, S_{n-1}, S_n, T_1, T_2, \ldots, T_{n-1}$, and $T_n$ independently represent hydrido radical;
X and Y independently represent hydrido, substituted or non-substituted alkyl, substituted or non-substituted acyl, substituted or non-substituted sulfonyl, or substituted or non-substituted aryl radical;
Z represents hydrido, hydroxy, substituted or non-substituted alkyloxy, substituted or non-substituted aryloxy, substituted or non-substituted amino radical;
$B_1, B_2, \ldots, B_{n-1}$, and $B_n$ are independently selected from natural nucleobases including adenine, thymine, guanine, cytosine and uracil, and unnatural nucleobases;
at least three of $B_1, B_2, \ldots, B_{n-1}$, and $B_n$ are independently selected from unnatural nucleobases represented by Formula II, Formula III, or Formula IV:
wherein,
$R_1, R_2, R_3, R_4, R_5$ and $R_6$ are independently selected from substituted or non-substituted alkyl, hydrido, hydroxy, and substituted or non-substituted alkyloxy radical; and,
$L_1, L_2$ and $L_3$ are a covalent linker represented by Formula V connecting a basic amino group to the moiety responsible for nucleobase pairing properties:
wherein,
$Q_1$ and $Q_m$ are substituted or non-substituted methylene (—CH$_2$—) radical, and $Q_m$ is directly linked to the basic amino group;
$Q_2, Q_3, \ldots$, and $Q_{m-1}$ are independently selected from substituted or non-substituted methylene, oxygen (—O—), sulfur (—S—), and substituted or non-substituted amino radical [—N(H)—, or —N(substituent)-]; and,
m is an integer between 1 and 16.

13. The peptide nucleic acid derivative according to claim 11, or a pharmaceutical salt thereof:
wherein,
n is an integer between 11 and 21;
$S_1, S_2, \ldots, S_{n-1}, S_n, T_1, T_2, \ldots, T_{n-1}$, and $T_n$ are hydrido radical;
X and Y are independently selected from hydrido, substituted or non-substituted alkyl, and substituted or non-substituted acyl radical;
Z represents hydroxy, or substituted or non-substituted amino radical;
$B_1, B_2, \ldots, B_{n-1}$, and $B_n$ are independently selected from natural nucleobases including adenine, thymine, guanine, cytosine and uracil, and unnatural nucleobases;
at least four of $B_1, B_2, \ldots, B_{n-1}$, and $B_n$ are independently selected from unnatural nucleobases represented by Formula II, Formula III, or Formula IV;
$R_1, R_2, R_3, R_4, R_5$ and $R_6$ are independently selected from substituted or non-substituted alkyl, and hydrido radical;
$Q_1$ and $Q_m$ are substituted or non-substituted methylene radical, and $Q_m$ is directly linked to the basic amino group;
$Q_2, Q_3, \ldots$, and $Q_{m-1}$ are independently selected from substituted or non-substituted methylene, oxygen, and amino radical; and,
m is an integer between 1 and 11.

14. The peptide nucleic acid derivative according to claim 11, or a pharmaceutical salt thereof:
wherein,
n is an integer between 11 and 19;
$S_1, S_2, \ldots, S_{n-1}, S_n, T_1, T_2, \ldots, T_{n-1}$, and $T_n$ are hydrido radical;
X and Y are independently selected from hydrido, and substituted or non-substituted acyl radical;
Z represents substituted or non-substituted amino radical; and,
$B_1, B_2, \ldots, B_{n-1}$, and $B_n$ are independently selected from natural nucleobases including adenine, thymine, guanine, cytosine and uracil, and unnatural nucleobases;
at least four of $B_1, B_2, \ldots, B_{n-1}$, and $B_n$ are independently selected from unnatural nucleobases represented by Formula II, Formula III, or Formula IV;
$R_1, R_2, R_3, R_4, R_5$ and $R_6$ are independently selected from substituted or non-substituted alkyl, and hydrido radical;
$Q_1$ and $Q_m$ are methylene radical, and $Q_m$ is directly linked to the basic amino group;
$Q_2, Q_3, \ldots$, and $Q_{m-1}$ are independently selected from methylene, oxygen, and amino radical; and,
m is an integer between 1 and 9.

15. The peptide nucleic acid derivative according to claim 11, or a pharmaceutical salt thereof:
wherein,
n is an integer between 11 and 19;
$S_1, S_2, \ldots, S_{n-1}, S_n, T_1, T_2, \ldots, T_{n-1}$, and $T_n$ are hydrido radical;
X and Y are independently selected from hydrido, and substituted or non-substituted acyl radical;
Z represents substituted or non-substituted amino radical;
$B_1, B_2, \ldots, B_{n-1}$, and $B_n$ are independently selected from natural nucleobases including adenine, thymine, guanine, cytosine and uracil, and unnatural nucleobases;
at least four of $B_1, B_2, \ldots, B_{n-1}$, and $B_n$ are independently selected from unnatural nucleobases represented by Formula II, Formula III, or Formula IV;
$R_1, R_3$, and $R_5$ are hydrido radical, and $R_2, R_4$, and $R_6$ independently represent hydrido, or substituted or non-substituted alkyl radical;
$Q_1$ and $Q_m$ are methylene radical, and $Q_m$ is directly linked to the basic amino group;
$Q_2, Q_3, \ldots$, and $Q_{m-1}$ are independently selected from methylene, oxygen radical; and,
m is an integer between 1 and 9.

16. The peptide nucleic acid derivative according to claim 11, or a pharmaceutical salt thereof:
wherein,
n is an integer between 11 and 19;
$S_1, S_2, \ldots, S_{n-1}, S_n, T_1, T_2, \ldots, T_{n-1}$, and $T_n$ are hydrido radical;
X and Y are independently selected from hydrido, and substituted or non-substituted acyl radical;
Z represents substituted or non-substituted amino radical;
$B_1, B_2, \ldots, B_{n-1}$, and $B_n$ are independently selected from adenine, thymine, guanine, cytosine, and unnatural nucleobases;
at least four of $B_1, B_2, \ldots, B_{n-1}$, and $B_n$ are independently selected from unnatural nucleobases represented by Formula II, Formula III, or Formula IV;
$R_1, R_2, R_3, R_4, R_5$, and $R_6$ are hydrido radical;
$Q_1$ and $Q_m$ are methylene radical, and $Q_m$ is directly linked to the basic amino group;
$Q_2, Q_3, \ldots$, and $Q_{m-1}$ are independently selected from methylene, and oxygen radical; and,
m is an integer between 1 and 8.

17. The peptide nucleic acid derivative according to claim 11, or a pharmaceutical salt thereof:
wherein,
n is an integer between 11 and 17;
$S_1, S_2, \ldots, S_{n-1}, S_n, T_1, T_2, \ldots, T_{n-1}$, and $T_n$ are hydrido radical;
X is hydrido radical;
Y represents substituted or non-substituted acyl radical;
Z represents substituted or non-substituted amino radical;
$B_1, B_2, \ldots, B_{n-1}$, and $B_n$ are independently selected from adenine, thymine, guanine, cytosine, and unnatural nucleobases;
at least four of $B_1, B_2, \ldots, B_{n-1}$, and $B_n$ are independently selected from unnatural nucleobases represented by Formula II, Formula III, or Formula IV;
$R_1, R_2, R_3, R_4, R_5$, and $R_6$ are hydrido radical;
$L_1$ represents —$(CH_2)_2$—O—$(CH_2)_2$—, —$CH_2$—O—$(CH_2)_2$—, or —$CH_2$—O—$(CH_2)_3$— with the right end is directly linked to the basic amino group; and,
$L_2$ and $L_3$ are independently selected from —$(CH_2)_2$—O—$(CH_2)_2$—, —$(CH_2)_3$—O—$(CH_2)_2$—, —$(CH_2)_2$—O—$(CH_2)_3$—, —$(CH_2)_2$—, —$(CH_2)_3$—, —$(CH_2)_4$—, —$(CH_2)_5$—, —$(CH_2)_6$—, —$(CH_2)_7$—, and —$(CH_2)_8$— with the right end is directly linked to the basic amino group.

18. The peptide nucleic acid derivative according to claim 11, which is selected from the group of peptide nucleic acid derivatives provided below, or a pharmaceutically acceptable salt thereof:

(N→C) Fethoc-CTT-A(6)TC(105)-CTA(6)-C(102)TT-A(5)AC-NH₂;

(N→C) Fethoc-C(105)TT-A(6)TC-CTA(6)-C(102)TT-A(5)AC(105)-A-NH₂;

(N→C) Fethoc-CA(5)T-A(6)TC-CTA(6)-C(102)TT-A(5)AC(105)-A-NH₂;

(N→C) Fethoc-CG(6)T-A(6)TC-CTA(6)-C(102)TT-A(5)AC(105)-A-NH₂;

(N→C) Fethoc-AC(102)T-TA(5)T-CC(102)T-A(6)C(102)T-TA(5)A-C-NH₂;

(N→C) Fethoc-CTT-A(6)TC-CTA(6)-C(102)TT-A(5)AC-NH₂;

(N→C) Piv-AC(102)T-TA(5)T-CC(102)T-A(6)C(102)T-TA(5)A-C-NH₂;

(N→C) Benzoyl-AC(102)T-TA(5)T-CC(102)T-A(6)C(102)T-TA(5)A-C-NH₂;

(N→C) Fethoc-Lys-AC(102)T-TA(5)T-CC(102)T-A(6)C(102)T-TA(5)A-C-NH₂;

(N→C) Fethoc-CTC(102)-A(6)TC-CTA(6)-C(102)TT-AA(6)C-NH₂;

(N→C) Fmoc-Val-CTC(102)-A(5)TC-CTA(6)-C(103)TT-AA(202)C-NH₂;

(N→C) Fethoc-A(6)GA-A(6)CT-TA(6)T-CC(102)T-A(6)CT-TA(6)-NH₂;

(N→C) Fethoc-AG(5)A-A(202)CT-TA(5)T-CC(102)T-A(6)CT-TA-NH₂;

(N→C) Piv-AG(5)A-A(202)CT-TA(5)T-CC(102)T-A(6)CT-TA-NH₂;

-continued (N→C) Ac-AG(5)A-A(2O3)CT-TA(5)T-CC(1O2)T-A(6)CT-TA- (N→C) Fethoc-A(5)GA(5)-AC(1O3)T-TA(5)T-CC(1O2)T-A(6)CT-TA(4)-NH$_2$;

(N→C) Fethoc-GA(5)A-C(1O2)TT-A(5)TC-CTA(5)-C(1O2)T-NH$_2$;

(N→C) Fethoc-G(5)AA(5)-C(1O2)TT-A(5)TC-CTA(5)-C(1O2)T-NH$_2$;

(N→C) Fethoc-GA(5)A-C(1O2)TT-A(5)TC-CTA(5)-C(1O2)T-Lys-NH$_2$;

(N→C) Benzoyl-GA(5)A-C(1O2)TT-A(5)TC-CTA(5)-C(1O2)T-NH$_2$;

(N→C) Ac-HEX-GA(5)A-C(1O2)TT-A(5)TC-CTA(5)-C(1O2)T-NH$_2$;

(N→C) Fmoc-Gly-GA(5)A-C(1O2)TT-A(5)TC-CTA(5)-C(1O2)T-NH$_2$;

(N→C) Me-GA(5)A-C(1O2)TT-A(5)TC-CTA(5)-C(1O2)T-NH$_2$;

(N→C) Benzyl-GA(5)A-C(1O2)TT-A(5)TC-CTA(5)-C(1O2)T-NH$_2$;

(N→C) Fethoc-G(5)AA(5)-CTT-A(5)TC-CTA(5)-C(1O2)T-NH$_2$;

(N→C) Fethoc-GA(5)A-C(1O2)TT-A(5)TC-CTA(5)-CT-NH$_2$;

(N→C) Fethoc-G(5)AA(6)-CTT-A(6)TC-CTA(6)-C(1O2)T-NH$_2$;
and (N→C) Fethoc-CA(5)G-AA(5)C-TTA(5)-TCC(1O2)-TA(5)-NH$_2$:

wherein,
A, G, T, and C are PNA monomers with a natural nucleobase of adenine, guanine, thymine, and cytosine, respectively;
C(pOq), A(p), A(pOq), G(p), and G(pOq) are PNA monomers with an unnatural nucleobase represented by Formula VI, Formula VII, Formula VIII, Formula IX, and Formula X, respectively;

wherein,
p and q are integers; and
the abbreviations for the N- and C-terminus substituents are as specifically described as follows: "Fmoc-" is the abbreviation for "[(9-fluorenyl)methyloxy]carbonyl-"; "Fethoc-" for "[2-(9-fluorenyl)ethyl-1-oxy]carbonyl"; "Ac-" for "acetyl-"; "Benzoyl-" for "benzenecabonyl-"; "Piv-" for "pivaloyl-"; "n-Propyl-" for "1-(n-propyl)-"; "-Lys-" for amino acid residue "lysine"; "—Val-" for amino acid residue "valine"; "-Leu-" for amino acid residue "leucine"; "-Arg-" for amino acid residue "arginine"; "-Gly-" for amino acid residue "glycine"; "Benzyl-" for "1-(phenyl)methyl-"; "Phenyl-" for "phenyl-"; "Me-" for "methyl-".

19. A method to treat an indication or condition involving increased expression of HIF-1α in as subject, comprising administering to the subject the peptide nucleic acid derivative according to claim 1, wherein the peptide nucleic acid derivative down-regulates HIF-1α.

20. A method to treat a solid tumor involving increased expression of HIF-1α in a subject, comprising administering to the subject the peptide nucleic acid derivative according to claim 1, wherein the peptide nucleic acid derivative down-regulates HIF-1α.

21. A method of inducing skipping of exon 2 in the HIF-1α pre-mRNA in cells to yield a HIF-1α mRNA splice variant lacking SCN9A exon 2, comprising contacting the cells with the peptide nucleic acid derivative of claim 1.

22. The method of claim 21, wherein the level of the full length HIF-1α mRNA and the HIF-1α functional activity in the cells are lowered after contacting the cells with the peptide nucleic acid derivative.

23. A method of decreasing HIF-1α levels in a subject, comprising administering to the subject the peptide nucleic acid derivative according to claim 1, wherein the peptide nucleic acid derivative down-regulates HIF-1α.

* * * * *

UNITED STATES PATENT AND TRADEMARK OFFICE
CERTIFICATE OF CORRECTION

PATENT NO. : 11,319,540 B2
APPLICATION NO. : 16/341272
DATED : May 3, 2022
INVENTOR(S) : Shin Chung et al.

Page 1 of 1

It is certified that error appears in the above-identified patent and that said Letters Patent is hereby corrected as shown below:

In the Claims

At Column 82, Lines 23-32, Claim 9, please delete:
Formula VII
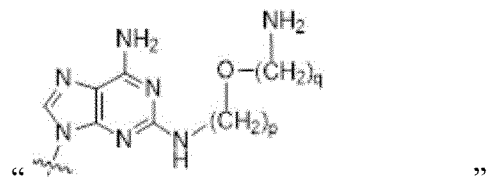
"       "

And replace with:
Formula VIII
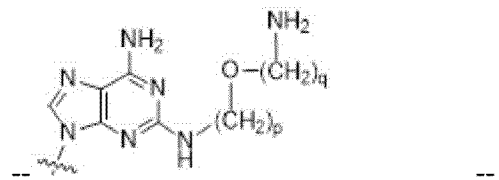
--       --

Signed and Sealed this
Ninth Day of August, 2022

Katherine Kelly Vidal
*Director of the United States Patent and Trademark Office*